(12) United States Patent
Cabiri et al.

(10) Patent No.: US 10,010,675 B2
(45) Date of Patent: Jul. 3, 2018

(54) STABILIZED PEN INJECTOR

(71) Applicant: MEDIMOP Medical Projects Ltd., Ra'anana (IL)

(72) Inventors: Oz Cabiri, Macabim-Reut (IL); Ran Hezkiahu, Herzliya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 15/023,038

(22) PCT Filed: Sep. 30, 2014

(86) PCT No.: PCT/US2014/058456
§ 371 (c)(1),
(2) Date: Mar. 18, 2016

(87) PCT Pub. No.: WO2015/048803
PCT Pub. Date: Apr. 2, 2015

(65) Prior Publication Data
US 2016/0235915 A1    Aug. 18, 2016

Related U.S. Application Data

(63) Continuation of application No. 14/186,403, filed on Feb. 21, 2014, now Pat. No. 9,427,529, which is a
(Continued)

(51) Int. Cl.
*A61M 5/20*    (2006.01)
*A61M 5/32*    (2006.01)
*A61M 5/42*    (2006.01)

(52) U.S. Cl.
CPC ............ *A61M 5/20* (2013.01); *A61M 5/3202* (2013.01); *A61M 5/3287* (2013.01);
(Continued)

(58) Field of Classification Search
CPC .. A61M 2005/2006; A61M 2005/2013; A61M 5/3202; A61M 5/3204; A61M 5/3287; A61M 5/425
See application file for complete search history.

(56) References Cited

U.S. PATENT DOCUMENTS 4,195,636 A    4/1980 Behnke
4,222,380 A    9/1980 Terayama
(Continued)

FOREIGN PATENT DOCUMENTS

EP    0 526 986 A1    2/1993
EP    1930038 A2    6/2008
(Continued)

OTHER PUBLICATIONS

U.S. Appl. No. 61/192,198, filed Sep. 15, 2008.
(Continued)

*Primary Examiner* — Rebecca E Eisenberg
(74) *Attorney, Agent, or Firm* — Panitch Schwarze Belisario & Nadel LLP

(57) ABSTRACT

The application concerns an autoinjector comprising a syringe, a driver for driving the plunger of the syringe and a stabilizing adaptor for holding the injector on the skin of a patient. The stabilizing adaptor has an adhesive base with a long axis to short axis ratio of at least 1.5 to 1. The syringe is orientated with its axis at an angle of between 60 and 120 degrees to the base during operation of the autoinjector.

20 Claims, 58 Drawing Sheets

Related U.S. Application Data continuation-in-part of application No. 14/096,977, filed on Dec. 4, 2013, now Pat. No. 9,393,369, and a continuation-in-part of application No. 13/063,236, filed as application No. PCT/US2009/056778 on Sep. 14, 2009, now Pat. No. 8,617,126.

(60) Provisional application No. 62/019,066, filed on Jun. 30, 2014, provisional application No. 61/884,597, filed on Sep. 30, 2013, provisional application No. 61/192,198, filed on Sep. 15, 2008.

(52) U.S. Cl.
CPC ........... *A61M 5/425* (2013.01); *A61M 5/3204* (2013.01); *A61M 5/326* (2013.01); *A61M 2005/2006* (2013.01); *A61M 2005/2013* (2013.01); *A61M 2207/00* (2013.01); *Y10T 29/49826* (2015.01)

(56) References Cited

U.S. PATENT DOCUMENTS

| | | | |
|---|---|---|---|
| 4,270,537 | A | 6/1981 | Romaine |
| 4,403,987 | A | 9/1983 | Gottinger |
| 4,781,688 | A | 11/1988 | Thoma et al. |
| 5,190,521 | A | 3/1993 | Hubbard et al. |
| 5,478,315 | A | 12/1995 | Brothers et al. |
| 5,662,678 | A | 9/1997 | Macklin |
| 5,766,186 | A | 6/1998 | Faraz et al. |
| 6,200,296 | B1 | 3/2001 | Dibiasi et al. |
| 6,743,211 | B1 | 6/2004 | Prausnitz et al. |
| 7,060,054 | B2 | 6/2006 | Nissels |
| 7,291,159 | B2 | 11/2007 | Schmelzeisen-Redeker et al. |
| 7,740,600 | B2 | 6/2010 | Slatkine et al. |
| 2002/0022798 | A1 | 2/2002 | Connelly et al. |
| 2003/0229308 | A1 | 12/2003 | Tsals et al. |
| 2004/0030353 | A1 | 2/2004 | Schmelzeisen-Redeker et al. |
| 2005/0033234 | A1 | 2/2005 | Sadowski et al. |
| 2005/0101912 | A1 | 5/2005 | Faust et al. |
| 2006/0293722 | A1 | 12/2006 | Slatkine et al. |
| 2007/0270745 | A1 | 11/2007 | Nezhat et al. |
| 2009/0043245 | A1 | 2/2009 | Nguyen |
| 2009/0093792 | A1 | 4/2009 | Gross et al. |
| 2009/0118662 | A1 | 5/2009 | Schnall |
| 2010/0185148 | A1 | 7/2010 | Gillespie, III et al. |
| 2010/0286714 | A1 | 11/2010 | Gyrn et al. |
| 2011/0040280 | A1 | 2/2011 | Ijitsu et al. |
| 2011/0166509 | A1 | 7/2011 | Gross et al. |
| 2014/0088509 | A1 | 3/2014 | Sonderegger et al. |
| 2014/0249502 | A1 | 9/2014 | Nie |

FOREIGN PATENT DOCUMENTS

| | | |
|---|---|---|
| EP | 2316510 A2 | 5/2011 |
| EP | 2468340 A1 | 6/2012 |
| EP | 2468342 A1 | 6/2012 |
| EP | 2578188 A1 | 4/2013 |
| EP | 2714155 A2 | 4/2014 |
| WO | 03103750 A1 | 12/2003 |
| WO | 2004032989 A2 | 4/2004 |
| WO | 2006/016364 A2 | 2/2006 |
| WO | 2006/069380 A1 | 6/2006 |
| WO | 2008034743 A1 | 3/2008 |
| WO | 2012000836 A1 | 1/2012 |
| WO | 2012134588 A1 | 10/2012 |
| WO | 2012145685 A1 | 10/2012 |
| WO | 2012164397 A1 | 12/2012 |

OTHER PUBLICATIONS

Int'l Search Report dated Aug. 11, 2010 in Int'l Application No. PCT/US2009/056778.
Int'l Preliminary Report on Patentability dated Mar. 15, 2011 in Int'l Application No. PCT/US2009/056778.
Office Action dated Oct. 17, 2012 in U.S. Appl. No. 13/063,236.
Office Action dated May 23, 2013 in U.S. Appl. No. 13/063,236.
U.S. Appl. No. 14/096,977 by Cabiri, filed Dec. 4, 2013.
U.S. Appl. No. 14/186,403 by Cabiri, filed Feb. 21, 2014.
Int'l Search Report and Written Opinion dated Dec. 12, 2014 in Int'l Application No. PCT/US2014/058433.
Int'l Search Report and Written Opinion dated Mar. 2, 2015 in Int'l Application No. PCT/US2014/058446.
Int'l Search Report and Written Opinion dated May 27, 2015 in Int'l Application No. PCT/US2014/058456.
Office Action dated Jul. 2, 2015 in U.S. Appl. No. 14/096,977 by Cabiri.
Office Action dated Oct. 7, 2015 in U.S. Appl. No. 14/186,403 for Cabiri.
Office Action dated Jan. 4, 2016 in U.S. Appl. No. 14/096,977 by Cabiri.
Int'l Preliminary Examination Report dated Apr. 14, 2016 in Int'l Application No. PCT/US2014/058446.
Int'l Preliminary Examination Report dated Apr. 14, 2016 in Int'l Application No. PCT/US2014/058433.
Int'l Preliminary Examination Report dated Apr. 14, 2016 in Int'l Application No. PCT/US2014/058456.
Office Action dated Mar. 22, 2017 in CN Application No. 201480054191.8.
Office Action dated May 29, 2017 in EP Application No. 14789667.4.
Extended Search Report dated Jul. 3, 2017 in EP Application No. 16200040.0.
Office Action dated Jan. 12, 2018 in EP Application No. 14789667.4.
Office Action dated Feb. 19, 2018 in EP Application No. 14789668.2.
Office Action dated Nov. 16, 2017 in CN Application No. 201480054191.8.

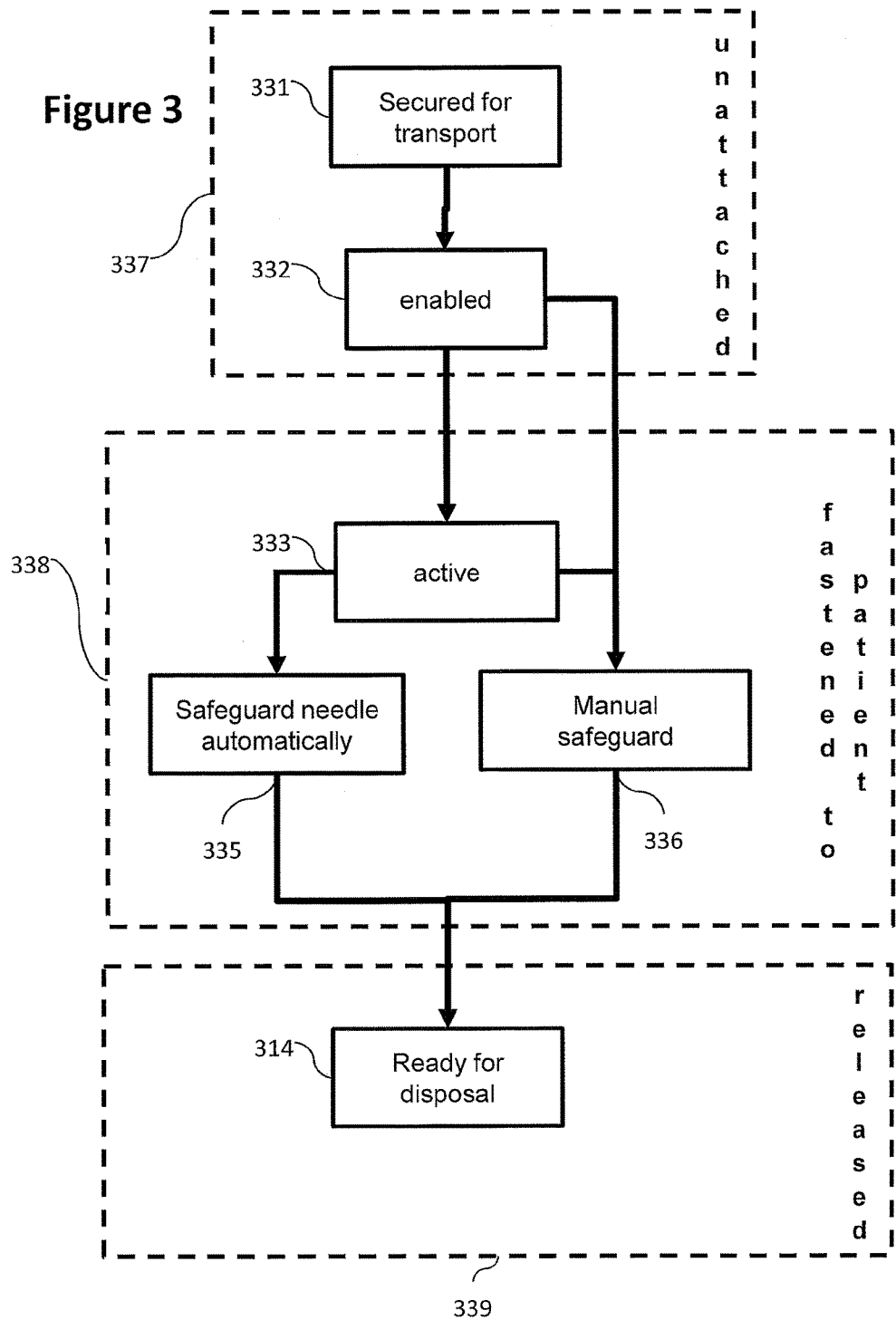

Figure 19A
Figure 19B
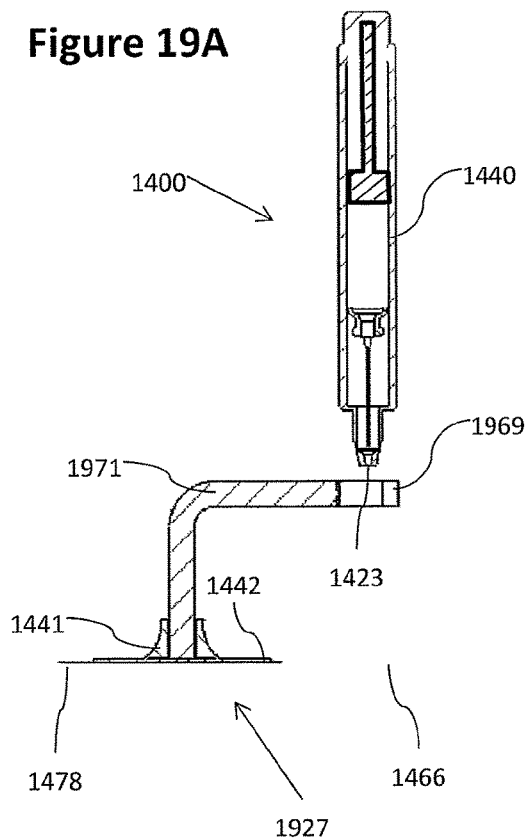
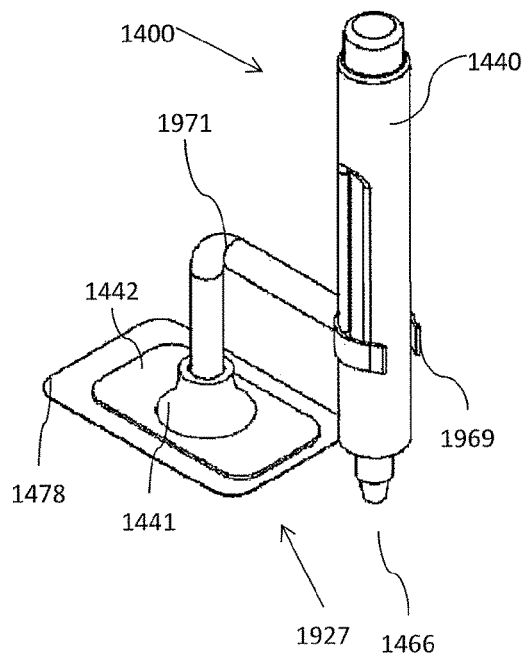

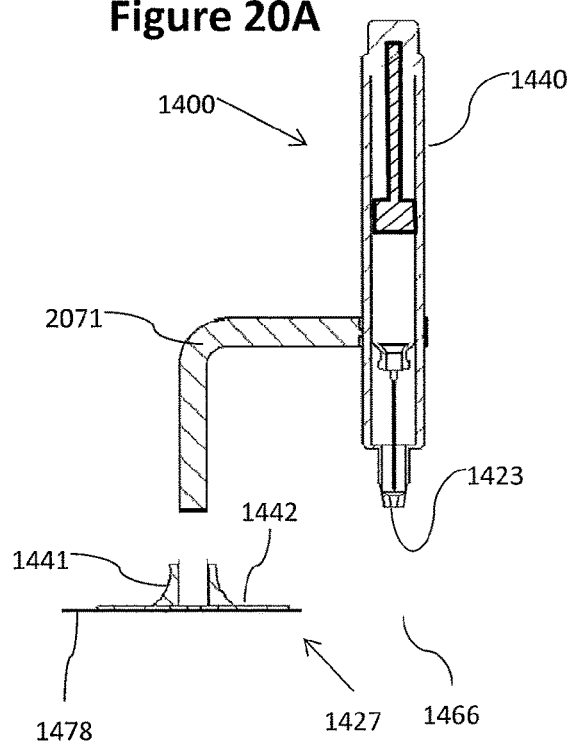
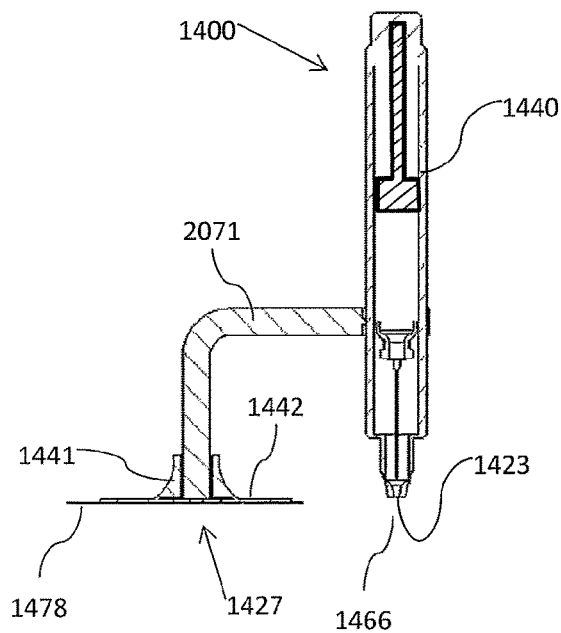

STABILIZED PEN INJECTOR

CROSS-REFERENCE TO RELATED APPLICATION

This application is a section 371 of International Application No. PCT/US2014/058456, filed Sep. 30, 2014, which was published in the English language on Apr. 2, 2015 under International Publication No. WO 2015/048803 which claims the benefit of U.S. Provisional Application No. 62/019,066, filed Jun. 30, 2014, U.S. application Ser. No. 14/186,403, filed Feb. 21, 2014, which is a continuation-in-part of U.S. application Ser. No. 14/096,977, filed Dec. 4, 2013, which claims the benefit of U.S. Provisional Application No. 61/884,597, filed Sep. 30, 2013, the disclosures of which are incorporated herein by reference.

BACKGROUND OF THE INVENTION

The present invention, in some embodiments thereof, relates to a medical injector and, more particularly, but not exclusively, to an injector stabilized for an extended bolus delivery.

International Patent Application Publication No. WO/2013/104414 to SANOFI-AVENTIS DEUTSCHLAND GMBH Describes a guiding assembly for an injection device comprising a mount adapted to receive an injection device, a first gripping member rotatably coupled to the mount, a first lateral stop member coupled to the first gripping member, and a spring biasing the first gripping member in a first angular position.

U.S. Patent Application Publication No. 2011/0166509 to Gross and Cabiri discloses an apparatus for use with tissue of a subject, including a substance configured to be injected into the tissue, and first and second tissue-squeezing surfaces configured to be placed on first and second sides of the tissue, to exert pressure on the tissue by being moved toward each other in response to a squeezing force (F), and to facilitate injection of the substance into the tissue by releasing the substance in response to application of the squeezing force.

U.S. Patent Application Publication No. 2012/0130344 to Ebbett discloses a skin gripping means for use with an injector. In one embodiment the skin gripping means is a needle guard. An exterior surface of the skin gripping means is provided with a plurality of fingers adapted to engage a subject's skin when in use. A method of performing a subcutaneous injection is also disclosed with includes the steps of bringing a skin gripping means of an injector into contact with the skin of a subject, moving the skin gripping means substantially parallel to the skin to thereby form a fold in the skin, moving a needle of the injector into the fold to a suitable position for a subcutaneous injection and injecting a substance through the needle.

U.S. Pat. No. 8,267,890 to Alchas discloses a medication delivery device, particularly an intradermal delivery device, having a needle cannula, with a sharpened distal end having a forward tip, and a limiter disposed about the needle cannula. The limiter has a distal end defining a skin engaging surface which is disposed transversely to, and at least partially about, the needle cannula. The skin engaging surface is generally non-flat with generally coplanar portions, and a recess being defined in the skin engaging surface which defines a void in or adjacent to the coplanar portions into which portions of a patient's skin can be deformed into when the skin engaging surface is pressed against the patient's skin. The forward tip of the needle cannula is spaced apart from a plane defined by the coplanar portions a distance ranging from about 0.5 mm to 3.0 mm such that the skin engaging surface limits penetration of the forward tip of the needle cannula to the dermis layer of the patient's skin.

Additional background art includes U.S. Patent Application Publication No. 2009/093,792 to Gross and Cabiri, U.S. Pat. No. 8,348,898 to Cabiri, U.S. Pat. No. 7,530,964 to Cabiri and U.S. Patent Application Publication No. 2009/0012494 to Yeshurun.

SUMMARY OF THE INVENTION

According to an aspect of some embodiments of the present invention there is provided an autoinjector comprising: a syringe including: a drug container, a hollow needle rigidly connected to a distal end of the drug container, the hollow needle in fluid communication with an interior of the drug container and a plunger sealing a proximal opening of the drug container; a driver for driving the plunger distally along an axis of the drug container thereby discharging a contents of the drug container through the needle into a patient; and an adhesive base having an aspect ratio of a long axis to a short axis of at least 1.5 to 1; the adhesive base being attached movably to the hollow needle for moving hollow needle axially through a needle hole of the adhesive base and orienting an axis of the drug container at an angle between 60 to 120 to the base during operation of the autoinjector.

According to some embodiments of the invention, a height of the autoinjector is at least the length of the short axis of the base.

According to some embodiments of the invention, an adhesive strength the adhesive base is small enough to be pivoted off a skin of a patient with ripping the skin when the autoinjector is pivoted around a pivoting axis perpendicular to a short axis of the base.

According to some embodiments of the invention, the hollow needle has a principle longitudinal axis substantially parallel to the axis of the drug container.

According to some embodiments of the invention, the autoinjector further comprises a flexible adhesive skirt extending beyond at least one edge of the adhesive base and where the flexible adhesive skirt extends in a direction of a short axis of the adhesive base further from the at least one edge of the adhesive base than from a second edge of the adhesive base.

According to some embodiments of the invention, the autoinjector further comprises a needle aperture in the adhesive base offset from the at least one edge toward the second edge.

According to some embodiments of the invention, the at least one edge and the second edge are substantially perpendicular to the short axis.

According to some embodiments of the invention, the hollow needle is oriented toward the at least one edge at an angle between 85 and 99 degrees of the base.

According to some embodiments of the invention, the autoinjector further comprises a needle cover for the hollow needle; and a handle connected the needle cover such that a linear movement of the handle pulls the needle over out a needle aperture of the base.

According to some embodiments of the invention, the autoinjector further comprises an adhesive cover for the adhesive base connected to the handle by an extender for peeling the adhesive cover from the base upon the linear movement of the handle.

According to some embodiments of the invention, the adhesive base is located distal to all of the needle cover.

According to some embodiments of the invention, the autoinjector further comprises a needle protection sheath configured to protrude distally from the autoinjector surrounding the hollow needle.

According to an aspect of some embodiments of the present invention there is provided a method of injecting a substance into a patient comprising: fastening a base of the injector to a skin of the patient; moving a syringe axially with respect to the base to insert a needle of the syringe through a needle aperture in the base into the patient; discharging the substance from the syringe through the needle into the patient while the injector remains fastened to the patient; pivoting the injector around an axis along the skin to unfasten the base from the patient.

According to some embodiments of the invention, base has an aspect ratio of a long axis to a short axis of at least 1.5 to 1 and wherein the pivoting is around the axis substantially perpendicular to a short axis of the base.

According to some embodiments of the invention, the pivoting is around the axis is along an edge of the base.

According to some embodiments of the invention, the base includes a flexible adhesive skirt extending beyond at least one edge of the base and wherein the pivoting is around the axis opposite an opposite edge of the base and wherein the skirt extends less beyond the opposite edge than and extent of the base beyond the at least one edge.

According to an aspect of some embodiments of the present invention there is provided a method of manufacture of a stabilized autoinjector comprising: installing a syringe rigidly attached to a sterile needle and needle cover into a pen injector having an adhesive base; and attaching a cover remover to the needle cover through an aperture in the adhesive base.

According to some embodiments of the invention, the method further comprises packaging the stabilized autoinjector for shipping to a patient after the installing and attaching.

According to some embodiments of the invention, the needle cover is located entirely on one side of the adhesive base.

According to some embodiments of the invention, the syringe includes a plunger sealing a proximal opening thereof and wherein the installing includes inserting the syringe into a channel in a distal assembly of the autoinjector, the distal assembly including the adhesive base on a distal end thereof and further comprising: joining the plunger to a transmission and motor for discharging medicine from the syringe by driving the plunger distally into the syringe, the joining by attaching a proximal assembly to the distal assembly.

According to some embodiments of the invention, the attaching includes uniting the distal assembly and the proximal assembly by an axial motion.

According to an aspect of some embodiments of the present invention there is provided a stabilizer for an autoinjector including housing including a distal surface and a side surface, the autoinjector also including a protective needle sleeve extending distally from the autoinjector, the stabilizer comprising: a connector for attaching to the side surface of the autoinjector; and a fastener for attaching a base of the stabilizer to a skin of a patient the connector configured for holding the housing of the autoinjector in a fixed spatial relation to the fastener; a needle aperture in the base, the needle aperture being large enough for the sleeve to extend through the aperture.

According to some embodiments of the invention, the base has an aspect ratio of a long axis to a short axis of at least 1.5 to 1.

According to some embodiments of the invention, the stabilizer further comprises a flexible adhesive skirt extending beyond at least one edge of the base and wherein the flexible adhesive skirt extends in a direction of a short axis of the base further from the at least one edge of the base than from a second edge of the base.

According to some embodiments of the invention, the stabilizer further comprises a needle aperture in the base offset from the at least one edge toward the second edge.

According to some embodiments of the invention, the at least one edge and the second edge are substantially perpendicular to the short axis.

According to some embodiments of the invention, the stabilizer further comprises a needle cover for preserving a sterility of a hollow needle of the autoinjector; and a handle connected the needle cover such that a linear movement of the handle pulls the needle cover out the needle aperture.

According to some embodiments of the invention, the stabilizer further comprises a cover for the base connected to the handle by an extender for peeling the cover from the base upon the linear movement of the handle.

According to some embodiments of the invention, the base is located distal to all of the needle cover.

According to an aspect of some embodiments of the present invention there is provided an article of manufacture for stabilizing an autoinjector comprising: a fastener for attachment to an injection site of a patient; and a connector for axially reversible attaching to a housing of the autoinjector, the connector configured for contacting an area of less than 4 $cm^2$ of the housing and wherein the connector is configured to reversibly hold the housing in a fixed orientation to the fastener.

According to some embodiments of the invention, the area of the house includes at least one location at least 1 mm distant from a distal surface of the autoinjector.

According to some embodiments of the invention, the connector includes a cavity for enclosing a portion of the autoinjector.

According to some embodiments of the invention, the fastener includes an adhesive surface.

According to some embodiments of the invention, the adhesive surface has a surface area on at least 2 $cm^2$.

According to some embodiments of the invention, the contacting area is on a side of the autoinjector.

According to an aspect of some embodiments of the present invention there is provided a method of retrofitting for stabilized operation an autoinjector configured for discharging of medicine to a skin of a patient contacting a distal surface of the autoinjector comprising: connecting a surface of an external housing of the autoinjector to a stabilizing adapter, the surface including at least one location not on a side surface of the housing; and supplying the autoinjector to a patient after the connecting before fastening the stabilizing adapter to patient.

According to some embodiments of the invention, the method further comprises packaging the autoinjector for shipment after the connecting.

According to some embodiments of the invention, the method further comprises enclosing a portion of the autoinjector in the adaptor.

According to some embodiments of the invention, the autoinjector includes a syringe rigidly attached to a sterile needle and needle cover and wherein the adaptor includes an adhesive base the method further comprising: attaching a cover remover to the needle cover through an aperture in the adhesive base.

According to some embodiments of the invention, the needle cover is located entirely on one side of the adhesive base.

According to an aspect of some embodiments of the present invention there is provided a drug delivery device comprising: a preloaded syringe; including a sterile hollow needle, a barrel in fluid communication with the sterile hollow needle, a distal end of the barrel rigidly attached to the sterile hollow needle, a plunger glidingly sealing a proximal end of the barrel, the plunger sliding distally thereby discharging a contents of the barrel out the hollow needle and a flange at a proximal end of the barrel; a proximal housing portion including a motor assembly and a transmission converting a rotation motion of the motor assembly to a linear motion; a distal housing portion including a channel fitting the preloaded syringe, the channel including a distal opening large enough for inserting the syringe into the channel a proximal opening large enough to allow the hollow needle to protrude from a proximal end of the proximal housing portion; and an adhesive base for fastening the distal portion to a skin of a patient, and wherein when the syringe is inserted into the channel, joining a distal end of the proximal housing to a proximal end of the distal housing operationally connects the transmission to the plunger such that activating the motor brings about discharging of the contents of the barrel.

According to some embodiments of the invention, the drug delivery device further comprises a mechanical connector for fastening the distal housing portion to the proximal housing portion.

According to some embodiments of the invention, the motor assembly includes: a support structure connectable to the proximal housing portion, a motor rigidly attached to the support structure, a power source rigidly attached to the support structure and a syringe position sensor rigidly attached to the support structure; the syringe position sensor controlling an electrical connection between the power source and the motor.

According to some embodiments of the invention, the preloaded syringe includes a needle cover preserving sterility of the sterile needle and the distal housing portion includes an activation device including a handle accessible from outside the channel an attachment mechanism, exposed to the channel such that when the preloading syringe is fully inserted into the channel, the attachment mechanism attaches to the needle cover a coupler passing through a needle aperture in the adhesive base, the coupler connecting the handle to the attachment mechanism.

According to some embodiments of the invention, an adhesive cover for the adhesive base connected to the handle by an extender for peeling the adhesive cover from the base.

According to some embodiments of the invention, the adhesive base is located distal to all of the needle cover.

According to some embodiments of the invention, the distal housing portion further includes a biasing mechanism pushing the syringe distally to a disengaged position.

According to some embodiments of the invention, the adhesive base has an aspect ratio of a long axis to a short axis of at least 1.5 to 1.

According to some embodiments of the invention, the needle has a principle longitudinal axis substantially parallel to an axis of the barrel.

According to some embodiments of the invention, the drug delivery device further comprises a flexible adhesive skirt extending beyond at least one edge of the adhesive base and where the flexible adhesive skirt extends in a direction of a short axis of the adhesive base further from the at least one edge of the adhesive base than from a second edge of the adhesive base.

According to some embodiments of the invention, the drug delivery device further comprises a needle aperture in the adhesive base offset from the at least one edge toward the second edge.

According to some embodiments of the invention, the at least one edge and the second edge are substantially perpendicular to the short axis.

According to some embodiments of the invention, the needle is oriented toward the at least one edge at an angle between 85 and 99 degrees of the base.

According to an aspect of some embodiments of the present invention there is provided a method of manufacture of an autoinjector comprising; supplying a preloaded syringe, a preassembled distal housing portion including a channel for insertion of the preloaded syringe and a proximal housing member including a motor and a transmission; sliding the preloaded syringe longitudinally through an opening in a proximal end of the distal housing member into the channel; joining by an axial motion a distal end the proximal housing portion to a proximal end of the distal housing portion thereby connecting the transmission to a plunger of the preloaded syringe.

According to some embodiments of the invention, the preloaded syringe includes a sterile needle and needle cover and the distal housing member includes an adhesive base on a distal end thereof, and the method further comprises attaching a cover remover to the needle cover through an aperture in the adhesive base.

According to some embodiments of the invention, the needle cover is located entirely on one side of the adhesive base.

According to some embodiments of the invention, the adhesive base includes an adhesive cover, and the method further includes connecting the cover remover to the adhesive cover such that removing the needle cover also peels the adhesive cover from the adhesive base.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3 is a state diagram of an injector in accordance with an embodiment of the present invention;

FIGS. 19A,B are a schematic cross sectional illustrations and a perspective illustration of a stabilizing adapter in accordance with some embodiments of the current invention;

FIGS. 20A,B are schematic cross sectional illustrations of a stabilizing adapter in accordance with some embodiments of the current invention;

DESCRIPTION OF SPECIFIC EMBODIMENTS OF THE INVENTION

Figure 1:
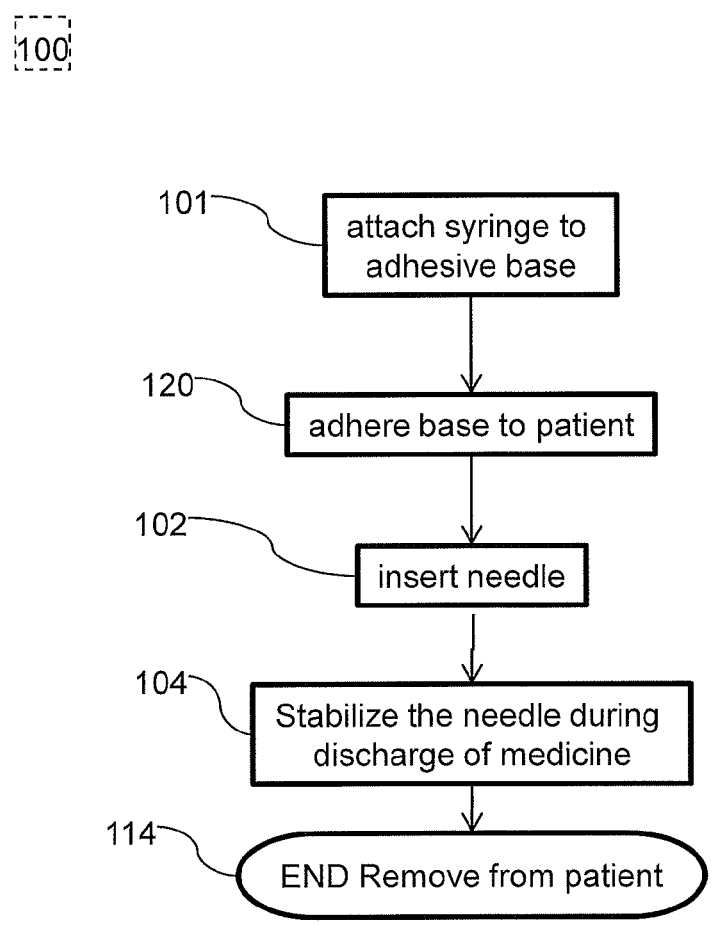
FIG. 1 is a flowchart illustrating a method of stabilizing a needle in a patient in accordance with an embodiment of the present invention.

The present invention, in some embodiments thereof, relates to a medical injector and, more particularly, but not exclusively, to an injector for an extended bolus delivery.
Overview
1 Pen Injector with Stabilizer An aspect of some embodiments of the present invention relates to an autoinjector and/or pen injector with stabilization. Stabilization may include for example fastening and/or adhering the injector to the skin of a patient. In some embodiments, a stabilized injector may perform injections of larger volumes and/or larger time lengths than a conventional pen injector.

In some embodiments, a pen injector may include a pre-sterilized fluid path. Optionally the fluid path may be inserted into the injector in a sterile and/or protected condition. Optionally a protective cover for the fluid path may be removed by an end user. Optionally the fluid path may be very simple. For example, the fluid path may include a straight needle directly and/or rigidly connected to a drug container. In some embodiments, the needle may be in fluid communication with the drug container, for example as in a standard hypodermic syringe. In some embodiments the needle may have a sterile cover. The needle cover may for example include a standard needle cover. Optionally, the needle may be coaxial to the drug container. Alternatively or additionally the needle may be mounted of center of the drug container. Some embodiments of the invention may include a standard straight needle. Alternatively or additionally, the needle may be bent and/or curved. Optionally the needle cover may not protect the sterility of the needle. For example the entire injector or a portion thereof may be sterilized.

In some cases, it may be difficult for a user to manually hold an autoinjector stable. For example the user may find it difficult to hole the injector immobile enough and/or for long enough to complete injection. A stabilized auto injector may include a skin fastener, for example an adhesive, to increase stability of the injector. The fastener may hold and/or assist the user to hold the activation zone of the injector and/or the injection zone and/or a needle aperture and/or a needle stable with respect to the skin of the patient. The pen injector may include and/or perform some or all of the functions of a syringe stabilizer and/or a needle positioner, for example as mentioned herein below.

In accordance with some embodiments of the current invention the payload of the syringe may include, for example between 0.5 and 2 ml and/or between 2 and 4 ml and/or between 4 and 5 ml of a drug and/or more. In some embodiments, the injector may discharge the entire payload as a single dose. For example, a pen injector may include an internally powered driver to drive the plunger and/or discharge the payload. For the sake of this application an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example the driver may be designed to discharge the payload over a time period ranging between 20 and 120 seconds and/or between 120 and 600 seconds and/or longer. In some embodiments, discharge may be driven by a driver. An internally powered driver may be powered by various mechanisms including for example a motor (including for example a DC motor, an actuator, a brushless motor) and/or a transmission including for example a telescoping assembly and/or a threaded element and/or a gear and/or a coupling and/or an elastic mechanism (for example a spring and/or a rubber band) and/or an expanding gas and/or a hydraulic actuator).

A pen injector in accordance with some embodiments of the current invention may include a medicine container. For example a medicine container may be a standard type syringe. Optionally a standard type syringe may be preloaded with medicine using standard equipment and/or in an aseptic room. A preloaded standard type syringe may optionally include a proximal opening. A plunger may optionally seal the proximal opening and/or protect the sterility of the contents of the syringe. A sterile needle (for example a hollow needle) may optionally be connected to the syringe barrel. For example, the hollow of the needle may be in fluid communication with the interior of the barrel. The needle may optionally be rigidly attached to the distal end of the barrel. The sterility of all and/or part of the needle may for example be protected by a sterile cover. The sterile cover may remain on the needle when the syringe is supplied and/or installed into an injector. For example, the medicine container may optionally include a cylindrical barrel rigidly attached to a needle. Optionally, the long axes of the needle and barrel of the syringe may be parallel and/or coaxial. Optionally, the needle may be mounted on the distal end of the barrel. Optionally the needle point may be pointing in the distal direction. In some embodiments a plunger may slide axially along the inside of the barrel to discharge a medicine payload. For example, the medicine may be discharged through the hollow needle.

An aspect ratio of the base may be defined as the ratio of the length of the longest axis of the base to the shortest axis. Optionally the axis ratio may range between 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

2 Syringe Stabilizer

An aspect of some embodiments of the present invention relates to a stabilization device for a hypodermic syringe. In some cases, it may be difficult for a user to manually hold a conventional syringe in a proper location and/or immobile enough and/or for long enough to complete injection. This problem may be particularly acute in home treatments where the caretaker may not be highly skilled. This problem may be particularly acute when injecting large volumes of liquid and/or for long periods of time, for example longer than 20 sec.

In some embodiments a syringe may be held stable with respect a fastener, fastened to the skin of a patient. The fastener may stabilize the syringe with respect to the skin of a patient. For example, with stabilization, a non-skilled person may be able to hold a syringe in its proper place for a time ranging between 20 to 600 seconds and/or the syringe may be held substantially immobile with respect to the skin of a patient for a time ranging for example between 60 to 180 seconds. For example the injector may inject of volume of drug ranging between 0.5 to 5 ml. Optionally, the injection may be a bolus delivery and/or extended bolus delivery and/or continuous delivery.

For example, holding the injector immobile may include preventing straining the needle and/or bending the needle and/or occluding the needle and/or injury the patient in the injection site and/or moving the needle from the intended injection site for example due to shearing forces along the patient's skin and/or forces perpendicular to the patient's skin. In some embodiments, the fastener may be strong enough to prevent lateral movement of the injector (sliding along the skin of the patient) under designated design stresses. In some embodiments, the fastener may be strong enough to hold the injector to the body of the patient without additional support (for example preventing lateral movement and/or longitudinal movement (perpendicular to the skin of the patient) and/or rotational movement with respect to the patient's skin under designated design stresses. Alternatively or additionally, the fastener may assist a user to manually hold the injector to the patients body.

3 Needle Positioner

An aspect of some embodiments of the present invention relates to a device for positioning a needle in an intended tissue for medical injection. For example, it is sometimes desired to inject a drug into subcutaneous tissue. In some cases locating a conventional needle in the proper tissue can be difficult. For example skin can fold, wrinkle, stretch and/or deform in such a way that it is difficult to locate the correct tissue. In some embodiments of the current invention, an adhesive base is used to hold the skin of a patient in a fixed position. A syringe may be held in a predetermined position with respect to the base such that a needle connected to the syringe pierces the skin and enters a desired tissue.

In some embodiments, a syringe may be held substantially perpendicular to a surface contacting the user's skin. For example, the syringe may be held at an angle ranging between 60° to 120° to the user's skin during injection. In some embodiments an injection may be into subcutaneous tissue. For example the needle length and/or needle insertion depth may range for between 3 to 12 mm. In some embodiments an injection may be into muscle. For example the needle length and/or needle insertion depth may range for between 16 to 25 mm.

4 Modular Autoinjector

An aspect of some embodiments of the present invention relates to a modular autoinjector and/or methods of construction and assembly of a parenteral drug delivery system. Optionally, final assembly of the autoinjector is by bringing together an Upper (proximal) Sub-assembly and/or a Lower (distal) Subassembly, and/or a pre-loaded syringe including for example a sterile needle and/or a sterile needle cover. The syringe optionally contains an aseptic medicament solution. For example the final assembly may consist of the pre-filled syringe being first installed in the Lower Subassembly in a motion along single axis. The Upper Subassembly and Lower Sub-assembly are optionally coupled together, e.g. by mechanical snap fit assembly, in a single axial motion with the pre-filled syringe captured within. The Upper Sub-assembly optionally comprises a housing, a transmission including for example coupling (for example a gear) and/or a telescoping screw assembly. Optionally a motor drive and/or some and/or all associated electrical components, e.g. switch, batteries and allied components, accessories, etc. are installed on an integral support structure (for example printed circuit board PCB). The electrical components and/or the support structure may constitute for example a pre-fabricated Motor Drive Sub-assembly. The prefabricated Motor Drive Sub-assembly can optionally be tested independently from the drug delivery system. The Motor Drive Sub-assembly is optionally configured to be installed into the Upper and Lower Subassemblies co-axially, for example by means of mechanical snap fit relationships.

5 Flexible Cover to Peel Adhesive Protector

An aspect of some embodiments of the present invention relates to a mechanism to peel an adhesive protector when a safety cover is pulled off of an autoinjector. For example the safety cover may be flexible and/or a hinged and/or may be anchored to an edge of the adhesive cover. For example the safety cover may include a needle cover remover connected to a folded adhesive protector. As the safety cover is pulled away the pulling force may be transferred to a peeling force, peeling back the adhesive at one or more edges of the adhesive protector.

6 Rotary Needle Retraction Mechanism

An aspect of some embodiments of the present invention relates to a needle safety mechanism for an autoinjector. Optionally, an unshielded needle may be safeguarded in response to resistance and/or a change of resistance to discharging of the injector payload.

In some embodiments a change in resistance to discharging may activate a rotary needle protector. For example, a resistance to discharging may engage a pair of threaded elements. Optionally, a drive may power discharging of a drug. The drive may drive a relative rotation between the pair of threaded elements. Relative rotation of the threaded elements may, in some embodiments, activate needle protection. For example, relative rotation of the pair of threaded elements may cause retraction of the needle.

In some embodiments, a lock may hold a needle in an unshielded position. The lock may optionally act as a support for a discharge driver. Increasing resistance to discharge may increase the stress on the driver. When the stress on the driver increases beyond a threshold and/or decreases beyond a threshold the lock may be released and/or the needle retracted to a safe location. For the sake of the current disclosure retraction of a needle may include pulling a needle point back into a shielded location without changing the length and/or shape of the shielding; and/or retracting may include extending the housing of the injector and/or a shield ahead of a needle point such that the needle is left in a shielded location.

In some embodiments, a support for a needle assembly may include a telescoping assembly. Optionally, the telescoping assembly may retract the needle (for example by contracting) in response to a stress from a driver.

In some embodiments, the safeguarding mechanism may include a sensor sensitive to a linear force from the driver. For example, a pushing force passes a threshold; a lock may be released moving the needle to the retracted configuration.

In some embodiments, the force to insert the needle to the skin of a patient may range for example between 0.02 to 0.2 N and/or between 0.2 and 0.5 N. Optionally, the force required to inject the drug (for example the force on a syringe plunger) may range for example between 5 to 60 N. For example the force required to inject the drug may depend on the injection rate and/or the viscosity of the drug and/or the syringe geometry and/or the needle dimensions.

In some embodiments a needle protection mechanism may be triggered by a linear force greater than, for example, between 10 to 60 N.

For example, an autoinjector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism may include a sensor that is sensitive to the force. For example the sensor may include a snap that gives way at 40 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 3 and 15 mm. The torque to power injection may range for example between 0.2 and 1.0 N*cm. The trigger torque (the torque at which the needle safeguarding is triggered) may range for example between to 0.5 to 2 and/or from 2 to 4 and/or from 4 to 10 N*cm.

In some embodiments a safety mechanism may include linear movement of the ranging between 5 to 15 mm. For example movement of the safety mechanism may include extension of a needle during insertion and/or retraction of the needle and/or extensions of a safety shield and/or retraction of a safety shield. Optionally a needle insertion length (for example the length of needle inserted into a patient) may range for example between 3 to 12 mm.

During injection, the linear movement of a plunger may range for example between 10-50 mm. The length of movement of the plunger may vary for example with the volume of medicine to be injected that may range for example between 0.5 to 3 ml.

In some embodiments, a sensor of a safeguarding mechanism may be sensitive to a torque. For example, the needle may be retracted when the mechanism is exposed to a twisting moment. Optionally, discharge may be driven by a torque. For example the driver may apply torque to threaded element pushing a plunger. When the torque on the driver reaches a threshold value, the needle may be released and/or retracted and/or a needle shield may be deployed. Alternatively or additionally the trigger mechanism may require both a torque and a linear force. For example, requiring both a torque and a linear stress may prevent premature activation due to momentary friction.

In some embodiments an interference element (for example a snap) may provide resistance to retraction. For example, an annular ring may impede contraction of a telescoping assembly. Alternatively or additionally a rib may impede twisting of a support structure. When stress from the driver passes a threshold, the stress may optionally overcome the interference element. Overcoming the interference element may for example reverts the support to a retracted configuration.

In some embodiments, a stress resulting from resistance to discharge may trigger deployment of a needle shield. The needle shield may optionally move to shield the needle in reaction to the increased stress.

In some embodiments, the retraction mechanism may include a rotary drive. For example, threaded element may raise the needle. For example a motor may drive a plunger injecting a drug (for example by means of a threaded plunger driving assembly). Upon triggering of the release mechanism the same motor may optionally rotate a second threaded assembly retracting the needle.

7 Stabilizing Adapter for an Autoinjector

An aspect of some embodiments of the present invention relates to an adaptor for extending the use of a drug delivery device, for example a single use autoinjector. Optionally an adapter may stabilize an existing injector. For example an adaptor may be configured to fasten an existing pen injector to an injection site of a patient and/or at a fixed orientation to the injection site. In some embodiments, stabilization may extend the use of an existing subcutaneous pen injector. For example stabilizing a pen injector may extend use of the injector to longer injection times and/or to larger injection volumes and/or to more viscous medicines and/or to lower temperatures and/or to use by movement limited patients and/or to patients for whom it is difficult to stabilize the injector and/or hold the injector to the skin (for example extremely fat and/or flabby patients). For example, a non-stabilized pen injector may be licensed for autonomous use (without a stabilizing adapter) with a certain medicament. Under certain conditions (for example when the medicament is highly viscous for example because it cold or highly concentrated) the injection time may extend beyond the licensed maximum injection time for the unstabilized injector. Optionally, in some embodiments adding a stabilizing adaptor will extend the permissible injection time of the injector. Extending the permissible injection time may, for example, allow use of the injector under the new conditions. Alternatively or additional, stabilization may extend use of a stabilized injector to a patient population that is limited in its ability to hold the non-stabilized injector in place.

In some embodiments, stabilization will have minimal or no affect on the workings of the injector. For example, a stabilizing adaptor may be designed to allow unchanged functioning and/or operation of an existing injector Minimizing changes in the function and/or operation of the injector may reduce the amount of testing necessary for licensing and/or marking of the stabilized injector and/or adaptor.

Optionally the injector may be held offset from the base of the stabilizer and/or the needle of the injector may be at an angle to the base of the stabilizer. For example, the needle location and/or the injector may be located away from an axis of pivoting for removing the stabilizer. For example the injector and/or the needle may be pointed inward with respect to the axis of pivoting. Alternatively or additionally the adhesive may be peeled from the skin manually, for example like a band aid. For example, the adhesive may have a tab and/or an area of reduced tackiness for easy peeling.

In some embodiments, an adaptor (for example a stabilizer) may extend use of an injector to new conditions. For example a stabilized injector may be used for adapting the injector to longer injection times, higher viscosity medicine and/or larger volumes of medicine. For example, the time of injection with the adaptor may range between 15 to 20 seconds (for example for between 0.8 and 1.2 ml of fluid having a viscosity ranging between 7 to 9 cp) and/or between 20 to 30 seconds (for example for between 1.2 and 1.7 ml of fluid having a viscosity ranging between 7 to 9 cp) and/or between 30 to 60 seconds (for example for between 1.7 and 2.3 ml of fluid having a viscosity between 8 to 12 cp) and/or between 60 to 120 seconds (for example for 2.0 to 2.5 ml of fluid having a viscosity of between 16 and 40 cp) and/or between 120 seconds and 3 minutes for larger volumes and/or viscosities In some embodiments, an adaptor may include an adjustable element. For example an adjustable element may include an elastic element and/or a spring and/or a threaded element and/or a clamp. In some embodiments an adaptor may include a friction fitting and/or an adhesive and/or a tightenable fitting. For example, a friction fitting may include one way teeth. For example it may require less force to insert an injector into an adapter then to remove the injector from the adapter. For example the force for removal may range between 1.5 and 3 times the force for insertion and/or the force for removal may range between 3 and 6 times the force for insertion and/or the force for removal may be more than 6 times the force for insertion. Alternatively or additionally a friction fitting may have substantially the same resistance to insertion and/or removal of the injector.

In some embodiments, an adaptor may be configured to attach to any one of a group of multiple injectors. Alternatively or additionally, an adaptor may be configured to be attached to a specific injector, for example, HUMIRA® pen autoinjection device for subcutaneous injection of the fully human monoclonal antibody adalimumab from Abbot lab and/or Enbrel® of Amgen—injected with auto injector for treatment of moderate to severe rheumatoid arthritis, adult chronic moderate to severe plaque psoriasis and/or other pen injectors like Ember™ and/or Molly™ and/or DAI™ and/or PSDI™ or other models from SHL and other producers In some embodiments, an extending adaptor and/or a portion thereof may be supplied with an injector. For example, an adaptor may be supplied with the injector in a kit. Alternatively or additionally an adaptor may be attached to an injector and supplied as a single unit. For example the adaptor will be attached to the injector by a supplier. Alternatively or additionally the adaptor may be attached to an injector by a doctor, a nurse, a pharmacist and/or another medical professional before being supplied to a patient. In some embodiments, the adaptor may be permanently attached to the injector. Alternatively or additionally, the adaptor may be removed from the injector, for example after use. For example, the injector may be removed from the patient while the adaptor remains fastened to the patient. Alternatively or additionally, the adaptor and/or the injector may be removed together from the patient. In some embodiments, a connector may be supplied with and/or come attached to the injector. A fastener for fastening to a patient may mate with a coupling. Optionally, a single fastener may be configured for use with different couplers (for example to connect to different injectors).

In some embodiments an adapter may be used to stabilize a subcutaneous injector. For example a subcutaneous injector may include a patch injector and/or a pen injector. For example, a pen injector may have a skin contact area on a base of the device, for example on a distal surface of the device. Optionally a pen injector has a long axis substantially perpendicular to the surface of an injection site on the patient. Alternatively or additionally a pen injector has a long axis that is substantially parallel to the long axis of the injection needle. A pen injector is optionally operated and/or configured to be operated with a long axis of the injector at an angle ranging between 80 to 100 degrees and/or between 60 and 120 degrees and/or between 30 and 150 degrees and/or ranging between 10 to 170 degrees to the surface of an injection site on the patient. The distal surface of a pen injector may have an area ranging between 1 mm$^2$ to 25 mm$^2$ and/or between 25 mm$^2$ to 1 cm$^2$ and/or between 1 cm$^2$ to 2 cm$^2$ and/or between 2 cm$^2$ to 4 cm$^2$ and/or between 4 cm$^2$ to 9 cm$^2$. For example the skin contact area may surround a needle aperture on the distal surface of the device. For example a patch injector may have a long axis parallel to the distal surface of the injector and/or parallel to an injection zone on the patient. The long axis of a patch injector may for example be at an angle ranging between 80 to 100 degrees and/or between 60 and 120 degrees and/or between 30 and 150 degrees and/or ranging between 10 to 170 degrees to the long axis of an injection needle. The distal surface of a patch injector may include the base of the device and/or a skin contact zone. The distal surface may, for example, have an area ranging between 4 cm$^2$ to 50 cm$^2$ or more. Subcutaneous injection sites may include for example an outer area of the upper arm and/or Just above and/or below the waist and/or an upper area of the buttock and/or a front of the thigh. In some embodiments a stabilizing adaptor may surround and/or increase the skin contact area of an injector and/or a distal surface of the injector. Alternatively or additionally an adaptor and/or a connector may be attached to a housing of an injector at a location distanced from the distal surface of the injector. For example the attachment location may range between 1 to 5 mm from the distal surface and/or between 5 mm and 2 cm from the distal surface and/or between 2 cm and 5 cm from the distal surface and/or more than 5 cm from the distal surface. For example the adapter may be attached to the side walls of the injector. The adaptor may fasten to the skin at the injection site and/or in an area ranging between 1 mm and 1 cm from the injection site and/or in an area ranging between 1 cm and 5 cm from the injection site and/or in an area ranging between 5 cm to 10 cm from the injection site.

In some embodiments, the connector may include a cavity for enclosing a portion of the injector. For example, a distal portion of the injector may be held in the cavity. In some embodiments the injector may be held inside the cavity by an adhesive and/or a friction element and/or an interference element and/or a magnet. For example the cavity may be cylindrical and/or conical and/or elliptical. Optionally the cavity may be fit for the shape of the outer housing of the autoinjector. For example the cross section of the opening of the cavity may range for example between 1 mm$^2$ to 25 mm$^2$ and/or between 25 mm$^2$ to 1 cm$^2$ and/or between 1 cm$^2$ to 2 cm$^2$ and/or between 2 cm$^2$ to 4 cm$^2$ and/or between 4 cm$^2$ to 9 cm$^2$. The length of the cavity may range for example between 1 mm to 5 mm and/or between 5 mm to 20 mm and/or between 20 mm to 50 mm and/or between 50 mm to 100 mm. The surface of contact between the injector and the connector may be less than 1 mm$^2$ (for example for a pressure fit screw or pin) and/or may range between 1 mm$^2$ to 4 mm$^2$ and/or may range between 4 mm$^2$ to 10 mm$^2$ and/or may range between 10 mm$^2$ to 1 cm$^2$ and/or may range between 1 cm$^2$ to 10 cm$^2$ and/or may be greater than 10 cm$^2$.

In some embodiments an adapter may be used to stabilize an intramuscular injector. For example an intramuscular injection site may include an area over a Deltoid Muscle and/or an area over a Vastus Lateralis Muscle and/or an area over a Ventrogluteal Muscle and/or an area over a Dorsogluteal Muscle.

In some embodiments, an extending adaptor may be supplied separately from the injector. For example, in some embodiments, the adaptor may be fastened to the patient without the injector. Optionally the injector is attached to the adaptor while the adapter is still on the patient. Alternatively or additionally, the patient and/or a medical aid may attach the adapter to the injector before fastening the adaptor to the patient.

In some embodiments, an adaptor extending use of an injector may make minimal changes in the injector. For example, the adaptor may be attached to the injector in a manner that permits access to the controls of the injector. Optionally, the adaptor is attached to the outer housing of the injector without changing the internal operation of the injector. For example, an autoinjector that is activated by the skin contact trigger in the autonomous mode may also be activated by a skin contract trigger in the extended mode. For example, an autoinjector that is activated by push button trigger in the autonomous mode may also be activated by the push button trigger in the extended mode.

In some embodiments, an adaptor may be configured to permit operation of a stabilized injector with minimal change from unstabilized autonomous operation. For example an adaptor may permit user access to the controls of the injector in the same manner as for autonomous operation. For example, the positioning and/or operation of the injector may be within the prescribed operation and/or positioning of the injector for unstabilized operation. For example, when stabilized the injector may be orientated to the patient as in autonomous operation. For example, the distal surface of the injector and/or a contact surface of the injector in autonomous operation may also contact the patient in stabilized operation. Alternatively or additionally, distal surface and/or the contact surface may contact the adaptor in stabilized operation and/or the adaptor may contact the skin of the patient. In some embodiments, in stabilized operation the distance between the injection site of the patient and a distal surface of the adaptor may range between 1 mm and 0.5 mm and/or between 0.5 mm and 0.1 mm and/or less than 0.1 mm. An angle between the injector and the injection site of the patient in stabilized operation may within the recommended range of angles during unstabilized operation.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Embodiments

1 Method of Positioning and/or Stabilizing a Needle

Referring now to the drawings, FIG. 1 illustrates a method of positioning and/or stabilizing a hypodermic needle in accordance with an embodiment 100 of the present invention. In the method an adhesive base is used to retain the skin and/or hypodermic tissue of a patient in a predicable geometry. A syringe retainer holds a syringe in a predetermined position with respect to the base such that a needle mounted to the syringe penetrates the skin to reach a desired tissue. A medicament may optionally be discharged to the desired tissue. The syringe and/or needle may optionally be held in place for an extended period, for example, for a long injection ranging between 30 seconds and 500 seconds. Optionally, an injection could include a large dose for example between 0.5 and 5 ml.

In some embodiments a syringe may be attached 101 to an adhesive base. The attachment may have fixed position and/or the syringe may be movable attached to the base. For example, the attached syringe may move longitudinally between a storage position wherein a needle is shielded by the base and an exposed position wherein a portion of the needle protrudes past the base.

In some embodiments, the base may be adhered 120 to the skin of a patient. Optionally the needle may be attached to the base either before or after adhesion 120 to the skin.

In some embodiments, a needle may be inserted 102 into the skin of the patient. For example, the needle may be inserted 102 by means of a longitudinal movement pushing a portion of the needle into a deployed position point past the base (for example through a hole in the base) into the patent. Optionally, the syringe may be fixedly attached to the base with the needle protruding beyond the adhesive such that placing the adhesive onto the patient also inserts the needle into the patient.

Optionally the device may stabilize 104 in a desired position during discharge of a medicine. When discharge of the medicine finishes, the needle may be removed 114 from the patient and/or the adhesive base may be peeled and/or pivoted from the skin. For example, the entire device may be twisted such that one side of the adhesive is lifted and/or pivoted and/or peeled from the skin while the far edge of the base of the injector remains in contact with the skin and serves as a fulcrum.

2 Method of Injecting a Drug

Figure 2:
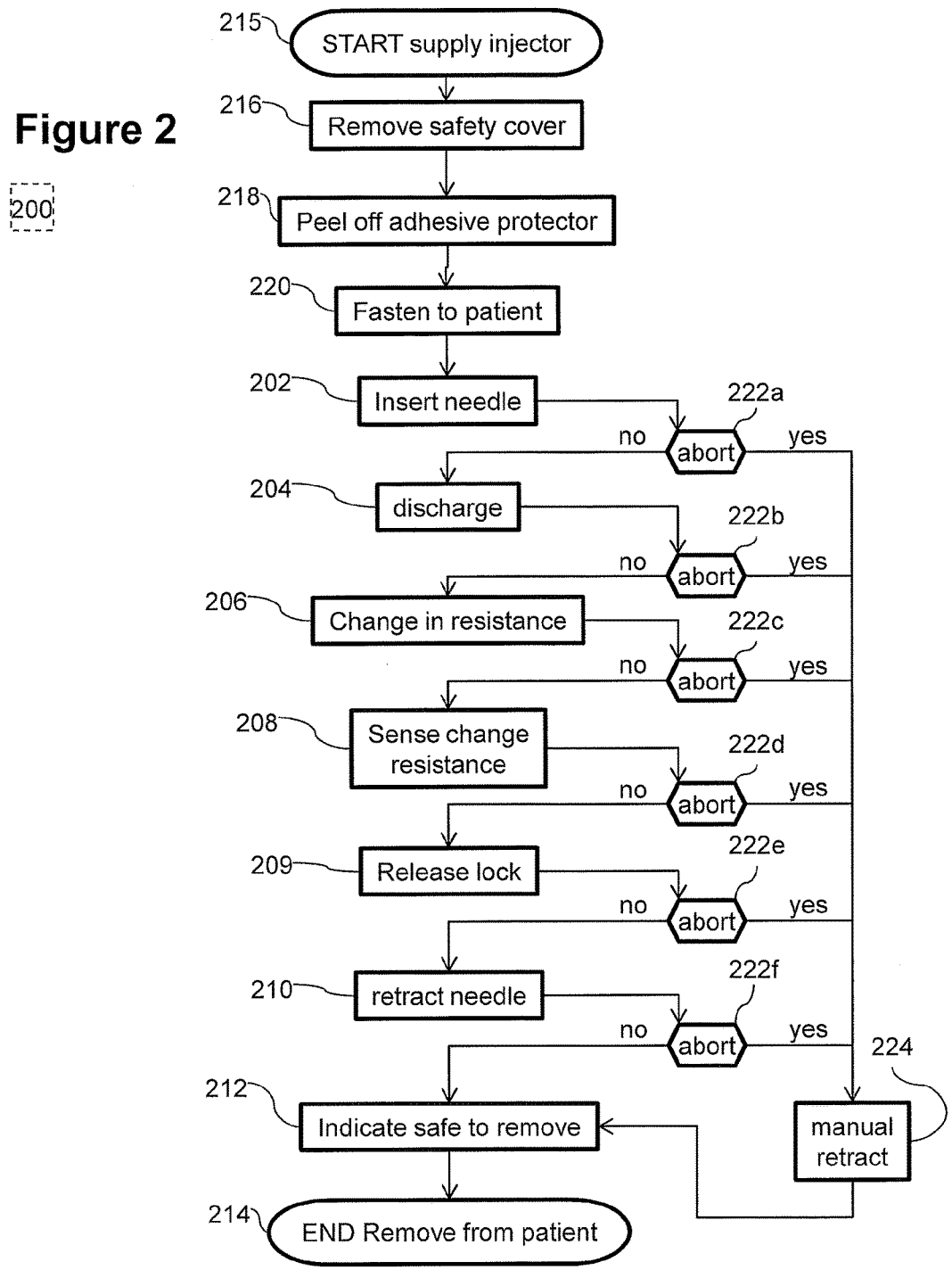
FIG. 2 is a flowchart illustrating a method of injecting a substance in accordance with an embodiment of the present invention.

Referring now to the drawings, FIG. 2 illustrates a method of injecting a drug in accordance with an embodiment 200 of the present invention. In the exemplary method, a needle is optionally held stable while a drug is dispensed to a patient (dispensing a drug may include discharging a drug from the injector).

In exemplary embodiment 200 a user (for example a patient and/or a medical aid in home care) may be supplied 215 with an autoinjector ready to administer a medicine.

The user may optionally remove 216 a safety cover from the injector. Removing 216 the cover may optionally include removing a sterile cover from a needle. Removing 216 the cover may optionally automatically peel 218 an adhesive protector from an adhesive. For example, the adhesive may be supplied to stabilize the injector on the skin of a patient during injection. The injector may optionally be fastened 220 to a patient (who may be the user). In some embodiments a user may hold the injector to the skin of a patient; the fastening 220 may stabilize the injector for example from shifts and/or movements of the patient and/or the user.

In some embodiments, the user may set off an activation mechanism. The activation mechanism may for example insert 202 the needle into the patient, for example by extending the needle outward. For example, a syringe may be moveably attached to the base. A syringe may optionally be rigidly attached to the syringe. For example the syringe may slide linearly along its axis. Sliding the syringe towards the base may cause the needle rigidly to protrude beyond the base. For example, part of the needle may pass through a hole in the base and pierce the skin of a patient. The adhesive of the base may hold the skin of the patient steady while the needle pierces the skin. The combination of an adhesive holding the skin and moving the needle to a predetermined position past the base may facilitate the inserting 202 of the needle into the skin to the desired depth.

The needle may optionally be locked in the extended position. Optionally, the needle may be biased to a protected position (for example to retract into a housing of the injector). Alternatively or additionally, the needle may be biased to the unshielded position. Alternatively or additionally, the autoinjector may be supplied with the needle in an extended mode and/or protected by a cover.

At a point during the injection process, an optional manual retraction 224 mechanism may be used to place the injector in a safeguarded mode. For example, when the user decides to abort 222a-f at a point in the process (for example when he detects some sort of malfunction and/or feels a negative reaction to the medicine) the user may manually retract 224 the needle. Optionally there may be an indicator to indicate 212 whether the needle was automatically retracted 210 and/or whether needle was manually retracted 224. Alternatively or additionally there may be an indicator whether a full dose was administered and/or how much medicine was administered.

Once the needle is inserted into the patient, the injector may optionally begin discharging 204 medicine. For example the medicine may be injected through the needle into the patient. Optionally, discharge may continue until a full dose of the medicine is administered.

In some embodiments, after administration of a full dose of the medicine, there may be a change 206 in resistance to further discharging. For example in a syringe based injector, a plunger may reach the end of the syringe and cease to move increasing resistance. Alternatively or additionally, after discharging the entire dose a transmission may be disconnected (for example a threaded element may pass the end of its threading) reducing resistance. Alternatively or additionally, the change 206 in resistance may result from another cause for example increased resistance due to a full or partial occlusion of a fluid pathway and/or jamming of a mechanical component (for example cross threading of a screw). The change of resistance may optionally be sensed 208 triggering retracting 210 of the needle.

In some embodiments, the needle may be locked in an unshielded state by a force sensitive lock. When the lock senses 208 the change 206 in resistance, it may release 209 the needle which may be retracted 210 to a shielded position.

In some embodiments, a flag may be supplied (for example a LED and/or a changing color indicator) to indicate 212 to the user that the needle has been retracted 210 and/or that the injector can safely be removed 214 from the patient and/or that a fastener has been released. For example, if the injector is adhered to the patient, it may be peeled off and/or a fastener may be released.

3 States of an Autoinjector

FIG. 3 is a state diagram of an autoinjector in accordance with an embodiment of the present invention. In general, may be supplied in an unattached 337 state. An unattached 337 autoinjector may have a secured 331 state. For example in the secured 331 state the injector may be safe to handle and/or transport. Optionally the injector may have an enabled 332 state. For example, in the enabled 332 state, the injector may be unstable and/or easily activated. For example, an injector may be switched from the secured 331 state to the enabled 332 state by removing a needle protector and/or an adhesive cover.

Once activated the injector may optionally be fastened to a patient. In the fastened 338 state the injected may optionally be activated. For example, while the injector is in the active 333 state, a needle may project from the injector. In some embodiments the injector may be hazardous to handle in the enabled 332 and/or active 333 state.

In some embodiments, after use (optionally whether or not administration of the full dose was successful) the user may want to remove and/or dispose of the autoinjector. In some embodiments, it may be difficult and/or dangerous to remove an injector in the enabled and/or active state. For example, when an injector is fastened to a patient by an adhesive, it may be difficult to remove the needle by pulling the injector away from the skin. Optionally, first a needle may be retracted from the skin into the injector. Subsequently the adhesive may be removal by pivoting and/or pulling and/or peeling from the skin. In some embodiments, the injector may automatically be safeguarded 335 for example by retraction of a needle upon completion of injection. Alternatively or additionally, the user may have the option to manually secure the injector into a safeguarded 336 state. For example, the optionally of manually needle retraction may avoid the situation where a patient may not be able to properly remove the injector due to a malfunction that leaves the injector fastened to the skin with the needle inserted into the patient. During and/or after safeguarding 335, 336 the injector may be removed from the patient.

Optionally, the injector may have a final released state 339, for example wherein the needle is retracted back into the injector and/or the needle tip is shielded and/or the injector has been unfastened from the patient. Optionally one or more indicators may be supplied to indicate the state of the injector and/or the quantity of medicine discharged. Once released, the injector may be in final 314 state (protected from hazards and/or ready for disposal, for example in a municipal waste).

4 Fastening Via Clasping

Figure 4A:
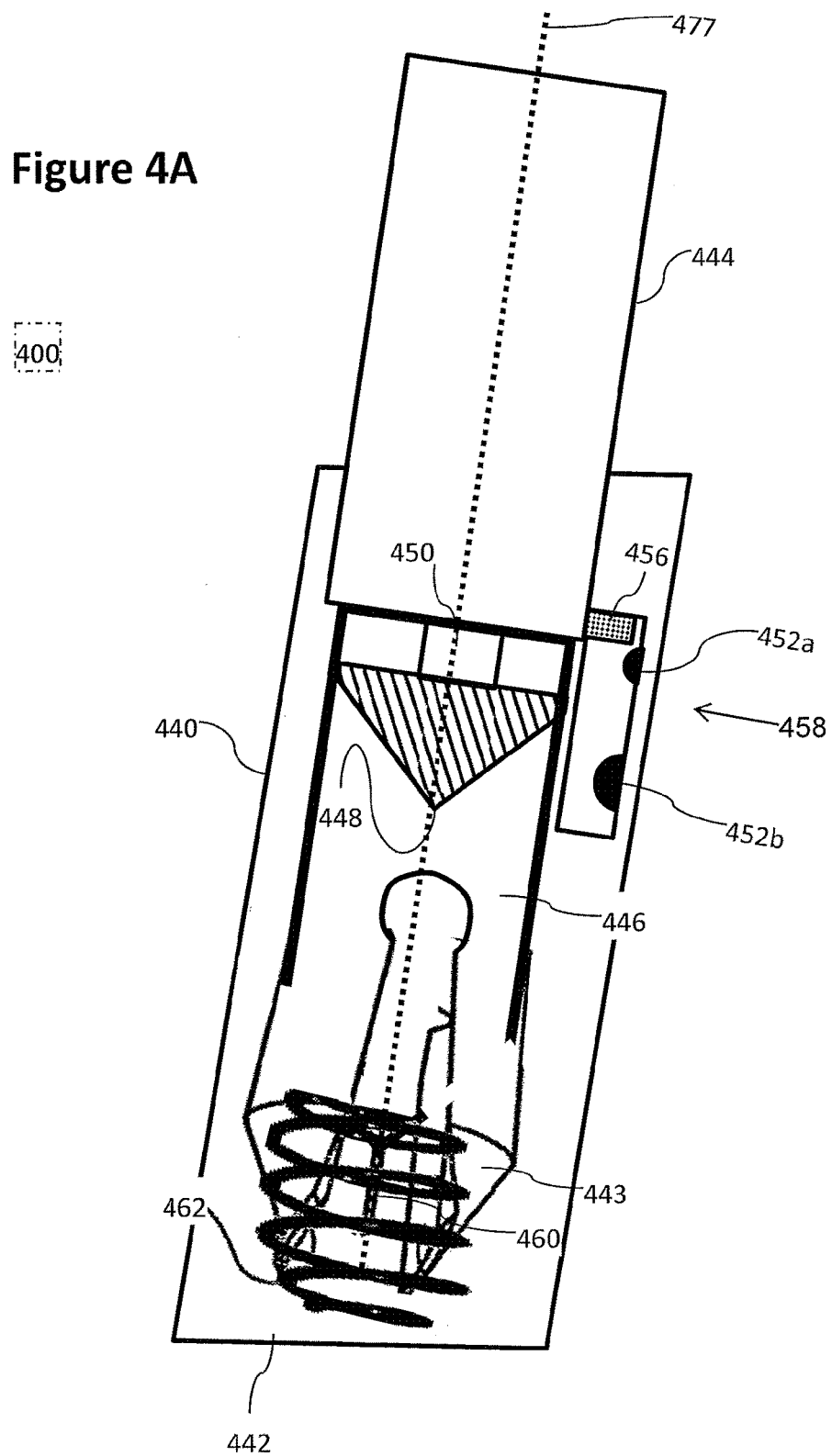
FIGS. 4A-C are schematic illustrations of a stabilized injector in accordance with an embodiment of the present invention.
Figure 4B:
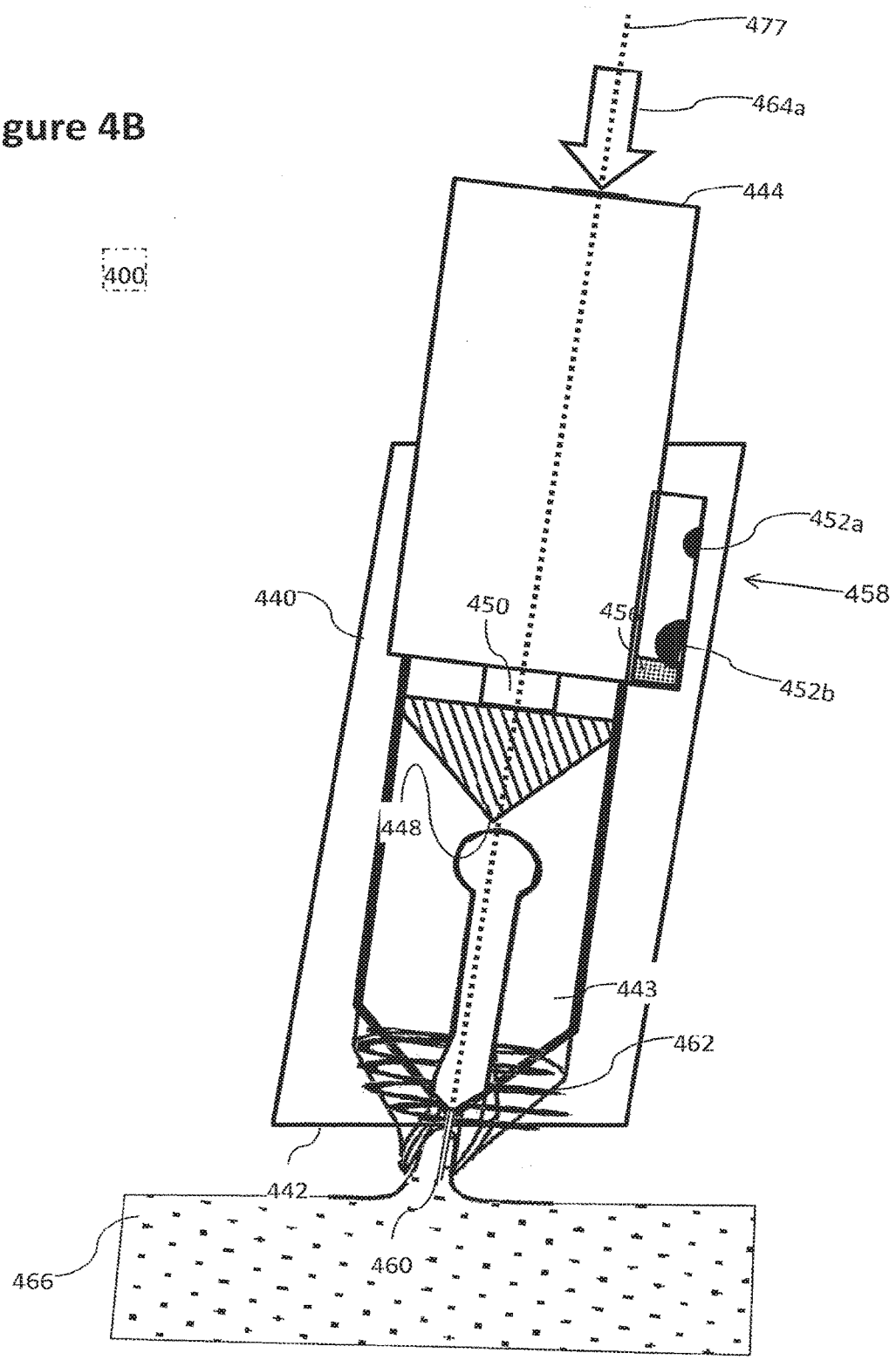
Figure 4C:
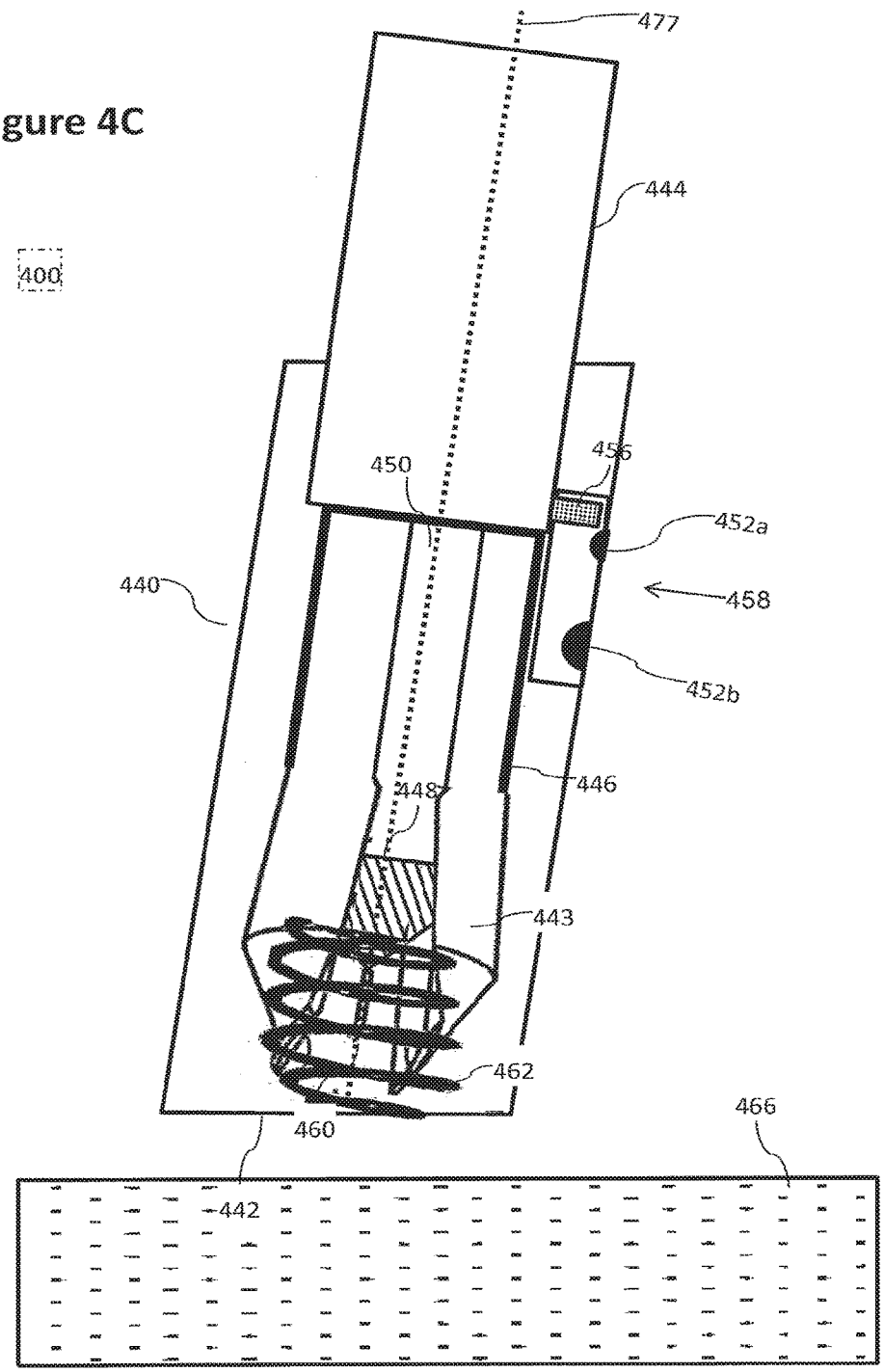

FIGS. 4A-C are schematic illustrations of a drug delivery device including a needle stabilizing mechanism that clasps the skin of a patient in accordance with an exemplary embodiment 400 of the present invention. In exemplary embodiment 400, a needle 460 is biased to a retracted state for example by a spring 462 (see for example FIG. 4A). In the retracted state, an optional clamp 443 may be biased in an open state.

During injection (for example as illustrated in FIG. 4B) needle 460 is optionally held in an extended state by a driver 444 and/or a medicine container 446. In the extended state, clamp 443 may close onto the skin of a patient holding the injector steady. For example needle 460 may be in fluid communication with medicine container 446.

In some embodiments, at the end of injection driver 444 may retract and/or release medicine container 446 and/or the needle 460. For example driver 444 may be unlocked. Once unlocked, driver 444 may optionally revert to a retracted state and/or clamp 443 may optionally be released and/or needle 460 may optionally retract back into the housing (for example as illustrated in FIG. 4D).

In some embodiments locking mechanism may include for example interference elements 452a,b and/or a locking pin 456 to retain driver 444 in a retracted and/or extended position until a force is applied. For example pin 456 may be rigidly connected to driver 444. In order to move driver 444 from the retracted position (for example as illustrated in FIGS. 4A and 4C) to the extended position (for example as illustrated in FIG. 4B) or back, a force may be applied to push pin 456 past interference elements 452a,b.

FIG. 4A illustrates exemplary embodiment 400 in an enabled state prior to activation. For example, in the enabled state an optional safety cover and/or a sterile cover may and/or an adhesive protector may have been removed from the injector. In the enabled state a needle 460 is shielded by an activation zone on a base 442 of a housing 440. Needle 460 is safeguarded by a retraction assembly including for example a spring 462 biasing the needle into housing 440 and a needle locking mechanism 458 and a driver 444 which hold needle 460 and its supporting medicine container 446 inside housing 440.

FIG. 4B illustrates exemplary embodiment 400 in an activated state, for example right before and/or at the beginning of discharge of a medication. For example, embodiment 400 is activated by pushing driver 444 with a sufficient force 464a. Pushing driver 444 optionally pushes needle 460, medicine container 446, and/or clamp 443 from the retracted position (illustrated in FIG. 4A) to the extended position (illustrated in FIG. 4B). Movement may, for example, be along the primary longitudinal axis 477 of medicine container 446. Optionally, needle 460 is shown coaxial to medicine container 446. Alternatively or additional a needle may be mounted off center of a syringe. As clamp 443 moves from the retracted to the extended position, it closes, grasping a skin 466 of the patient.

In some embodiment, once activated, driver 444 may apply a force on plunger rod 450 and/or plunger 448 to discharge medicine. Optionally driver 444 may be configured to drive discharge of the medicine over a relatively long period of time, for example between 30 to 120 seconds and/or between 120 to 600 seconds.

FIG. 4C illustrates exemplary embodiment 400 at the end of discharge of a medicament. Plunger 448 has optionally reached the end of its path. For example, a locking mechanism 458 has been released. Unlocking locking mechanism 458 may optionally trigger releasing clamp 443 and/or safeguarding needle 460.

5 Adhesive Syringe Stabilizer

Figure 5:
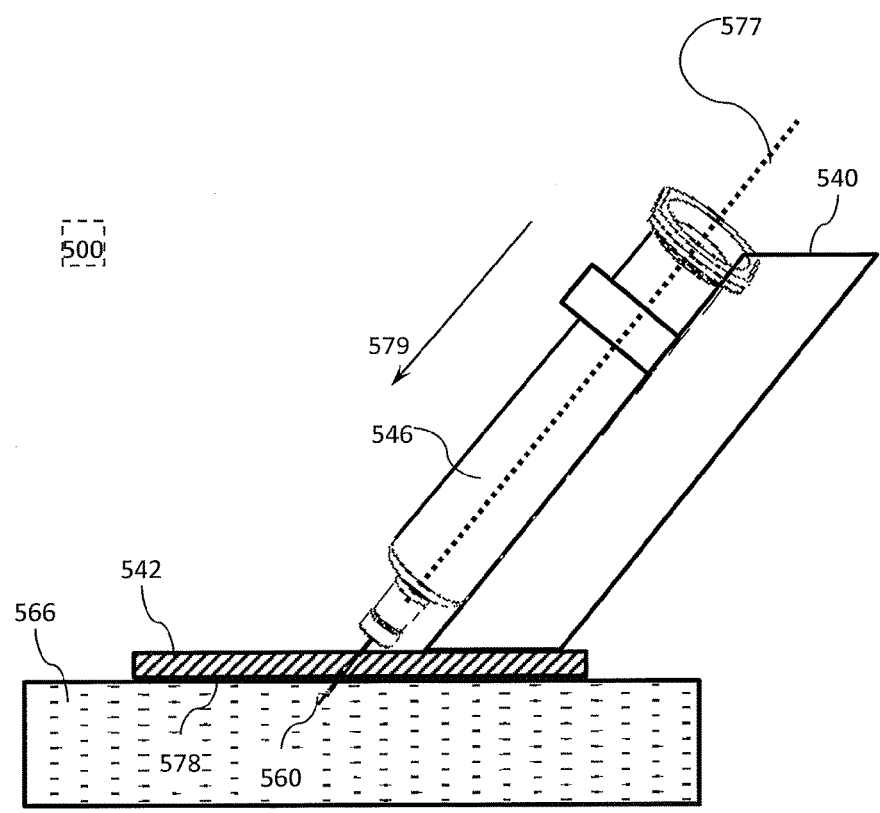
FIG. 5 is a schematic illustration of a needle stabilizer in accordance with an embodiment of the present invention.

FIG. 5 illustrates a drug delivery device including an adhesive syringe stabilizer 500 in accordance with an embodiment of the current invention. Syringe stabilizer 500 includes a base 542 adhering to a skin of a patient. A syringe 546 is attached to base 542 by means of a housing 540. Syringe 546 is rigidly connected to a needle 560 which protrudes from syringe 546 past base 542 into a skin 566 of a patient. In operation, needle 560 may be in fluid communication with syringe 546 and/or the patient. Needle 560 is shown in embodiment 500 mounted coaxially to syringe 546 (along the principal longitudinal axis 577 of syringe 546). Optionally, needle 560 may be mounted to the syringe off center. In the present application, the term principle longitudinal axis of a drug container may be used to refer to the longest axis of symmetry of the drug container.

In some embodiments, an adhesive 578 may be attached to a distal surface of a base 542. A housing 540 attached to a proximal side of base 542 may optionally hold syringe 546 with a needle 560 protruding from syringe 546 across base 542 (for example through a hole in base 542).

In some embodiments, syringe 546 may be attached to base 542 prior to adhering base 542 to a patient. The entire assembly may be attached to the patient (piercing the skin 566 with needle 560 and inserting needle 560 into the skin until adhesive 578 contacts skin 566).

In some embodiments, syringe 546 may be movably attached to housing 540. For example, syringe 540 may slide longitudinally along housing 540. Optionally, syringe 546 may be attached to housing 540 with needle 560 held proximal to base 542. Then the distal surface of base 542 may be adhered to skin 566. Subsequently, syringe 546 and needle 560 may be slide longitudinally in the distal direction 579 until needle 560 protrudes through base 542 into skin 566. Once needle 560 has been inserted into skin 566 adhesive 578 may assist a user to steady syringe 546 as he discharges medicine into the patient (for example by pushing on a plunger).

In some embodiments, base 542 may first be attached to the patient. Then a user may hold syringe 546 in his hand and insert needle 560 through a hole in base 542 into the skin of the patient. A possible advantage of inserting needle 560 into skin 566 after attaching base 542 to skin 566 is that adhesive 578 may inhibit deformation of skin 566 during needle insertion. This may make it easier to control the precise depth of insertion. After needle 560 has been inserted syringe 546 may be attached to housing 540. Adhesive 578 may assist a user to steady syringe 546 as he discharges medicine into the patient (for example by pushing on a plunger).

6 Detailed Illustration of States of an Injector

FIGS. 6A-D include detailed cross sectional side views illustrating four states of an autoinjector drug delivery device in accordance with an embodiment of the present invention. In some embodiments, an injector 600 is an automated self injection device. For example the self injecting device may in some ways be similar to a pen injector. Optionally injector 600 may be loaded with a standard type syringe 646 and/or hypodermic needle 660. For example, needle 660 may be rigidly connected and/or project from a distal end of syringe 646. Needle 660 may be coaxial with syringe 646. Alternatively or additionally the axis of needle 660 may be parallel to the primary longitudinal axis 677 of syringe 646 but offset therefrom. Syringe may be loaded into injector 600 with needle 660 in a sterile state and/or covered by a sterile cover.

In some embodiments, an injector may include for example an adhesive 678 base 642. For example, adhesive 678 base 642 may assist a user to hold injector 600 steady on the skin of a patient for an extended period. For example, injector 600 may be used to give injections of volume ranging between 0.5 and 3.0 ml over a time period ranging between 30 sec to 180 sec.

In some embodiments Injector 600 may include a transmission. For example, the transmission may include a rotary screw converting rotational motion of a motor 676 to linear motion for sliding a plunger to discharge a drug and/or for retracting a needle. Alternatively or additionally, in some embodiments, linear motion of the transmission may also be used to insert a needle. For example, in injector 600, the transmission includes for example an annular snap resistance element 652 paired to an annular driver support 656. When a linear stress increases past a threshold, the annular snap gives way and a needle 660 may optionally be retracted to a protected location.

Figure 6A:
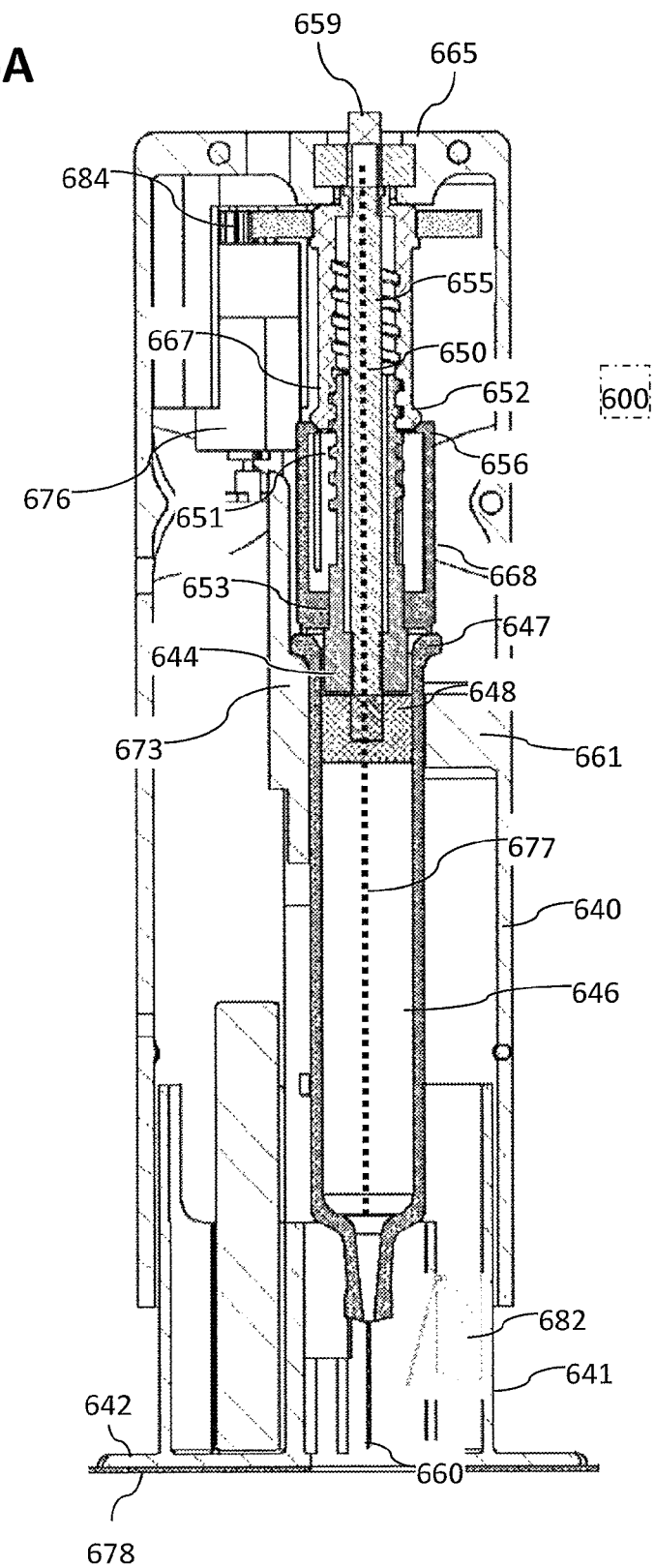
FIGS. 6A-F are detailed illustrations of a stabilized injector in accordance with an embodiment of the present invention.

FIG. 6A is a schematic cross sectional side view illustrating injector 600 in an enabled state (ready for activation). For example, in the enabled state an optional safety cover and/or a sterile cover may and/or an adhesive protector may have been removed from the injector. In the enabled state needle 660 is in a protected location, created by a shield 641 which extends the distal end of a housing 640 of the injector. Needle 660 and/or shield 641 may optionally be retained in position, for example by a snap and/or held in position by a biasing device, for example a spring.

In some embodiments, needle 660 may optionally be supported by a syringe 646; which is in turn supported for example by a cylindrical outer sleeve 668. Outer sleeve 668 may optionally be supported by an annular support 656 resting on an annular snap resistance element 652. For example annular snap resistance element 652 may extend radially outward from a cylindrical inner sleeve 667. Optionally, inner sleeve 667 and/or outer sleeve 668 and/or a driver 644 may be operationally linked to a coupling 684 (for example including a gear) such that rotating coupling 684 rotates one or more of inner sleeve 667 and/or outer sleeve 668 and/or a driver 644.

In some embodiments, syringe 646 position sensor, for example a motor switch 682 may be located in shield 641. In the enabled state (before activation), switch 682 is optionally switched off.

In injector 600, syringe 646 is held to outer housing 640 by a socket 661. Socket 661 allows syringe 646 to slide axially with respect to housing 640 but not to move laterally. In injector 600, coupling 684 is held rotatably fixed to housing 640 by bearing 659 in a hub 665.

Figure 6B:
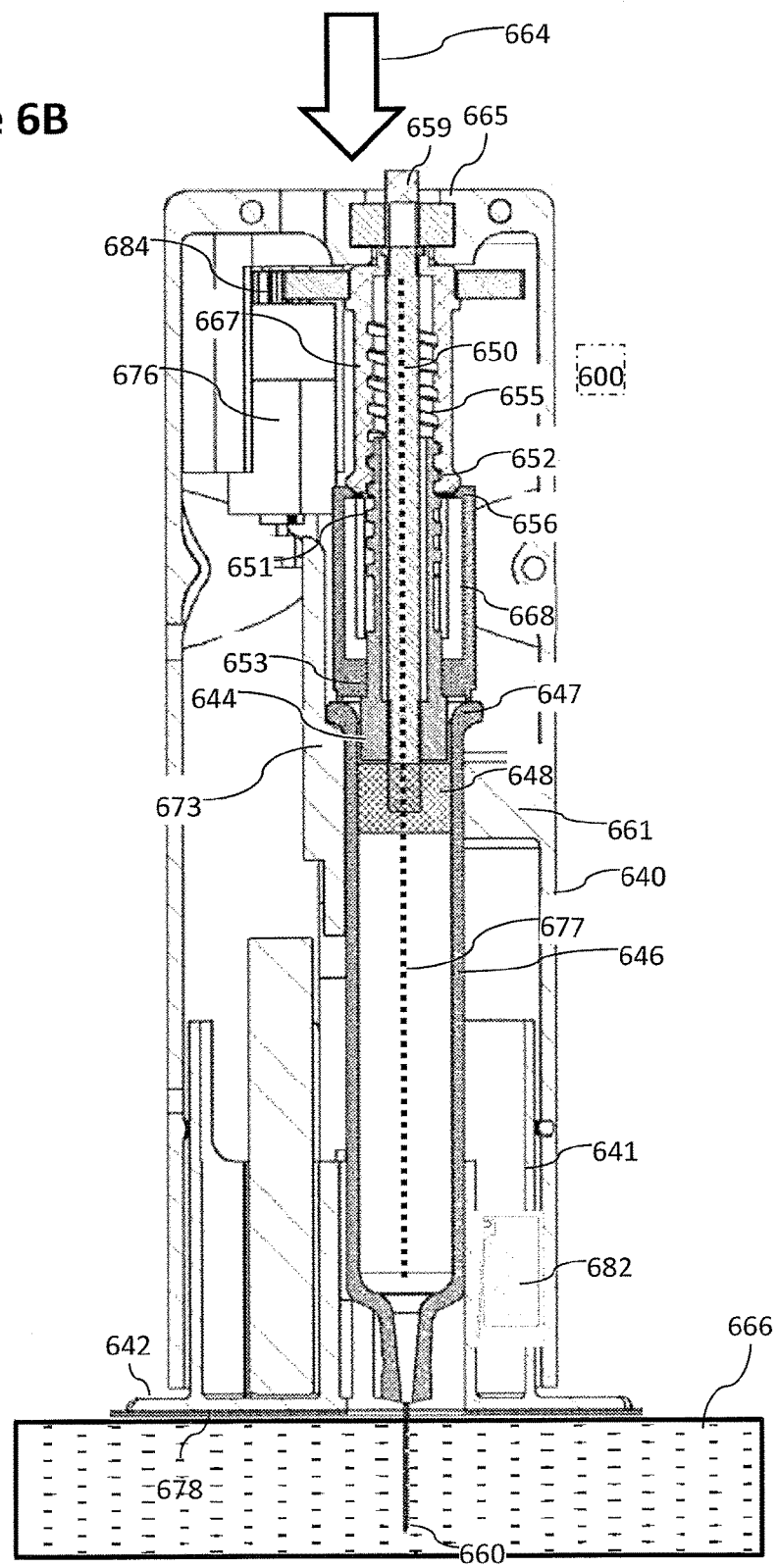

FIG. 6B is a schematic cross sectional side view illustrating injector 600 immediately after activation. For example, to activate the injector, a user may place the distal end of the injector (including for example an adhesive 678 and/or an activation zone on base 642) against the skin 666 of a patient and/or push 664 on the proximal end of the injector until shield 641 collapses into housing 640 in a direction parallel to the longitudinal axis of needle 660. Collapse of shield 641 may optionally unshield needle 660 tip which may for example be pushed into the skin 666 of the patient. For example, in operation, needle 660 may protrude from injector 600 into a patient. Optionally, in operation, needle 660 may be in fluid communication with syringe 646 and/or the patient. For example needle 660 may supply a fluid pathway for discharging medicine directly from syringe 646 through needle 660 into the patient.

In some embodiments, upon collapse of shield 641 switch 682 senses movement of syringe 646 to the active position and/or activates motor 676. For example in injector 600 switch 682 is depressed by being pushed against syringe 646. Depressing switch 682 may activate motor 676 to power a transmission and/or linear movement of a plunger 648 for discharging a drug. For example, in injector 600 motor 676 turns a coupling 684. Coupling 684 may include for example a gear. Coupling 684 may optionally rotate inner sleeve 667 and/or driver 644. In exemplary injector 600, driver 644 includes teeth and/or threads which engage a screw thread 653 on a plunger rod 650. Rotating driver 644 may optionally drive plunger rod 650 and/or plunger 648 in the distal direction, discharging the medicine. Optionally, plunger 648 continues to move distally until it is stopped by for example a blockage in the fluid path (preventing further discharge) and/or until plunger 648 reaches the distal end of syringe 646. Optionally, when needle 660 is in the extended position, a flange 647 of syringe 646 seats against a bracket 673, which holds syringe 646 and/or prevents further longitudinal movement.

Figure 6C:
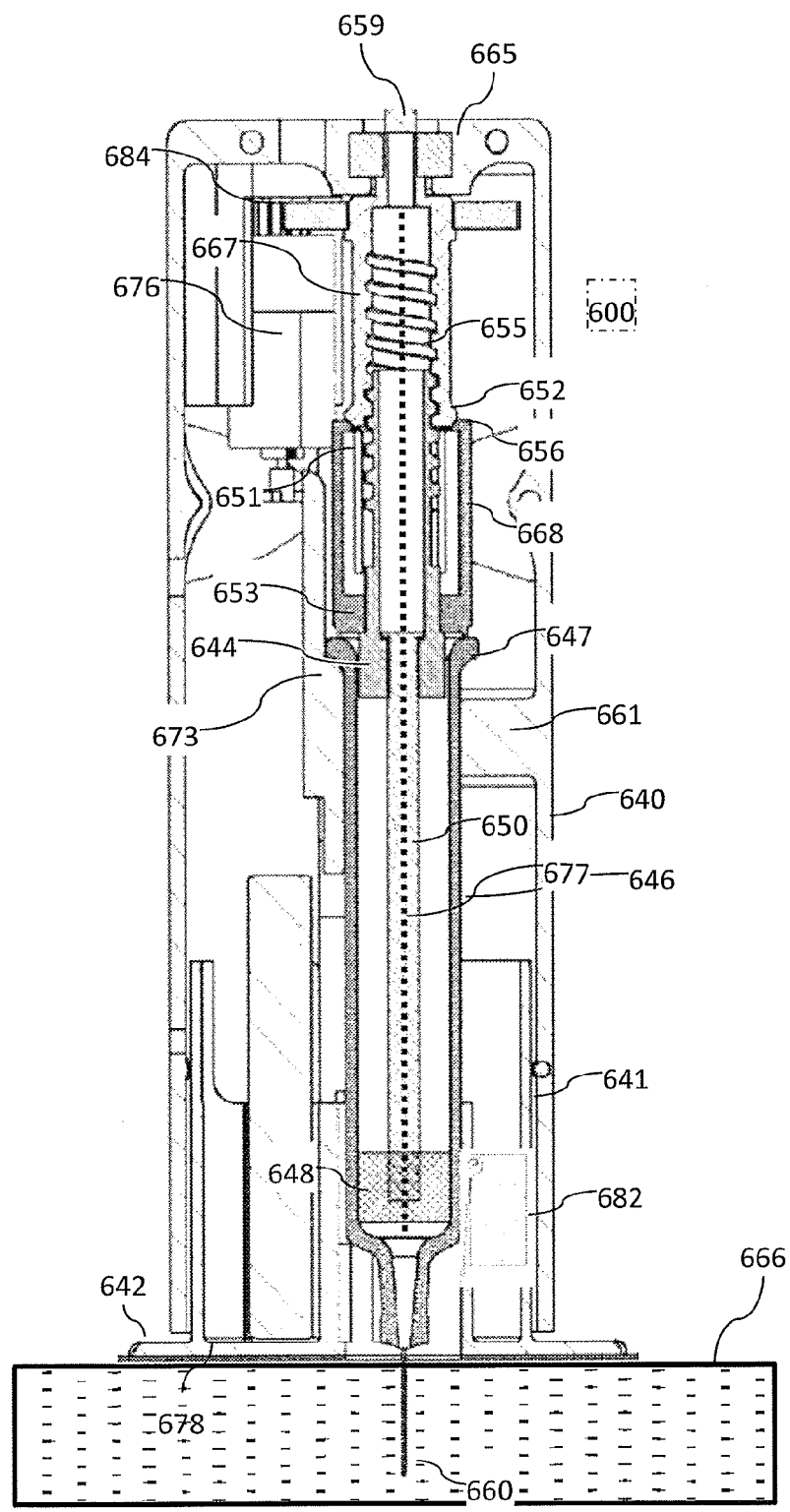

FIG. 6C is a schematic cross sectional side view illustrating injector 600 at the end of discharge of the payload. For example plunger 648 has discharged all of the medicine out of syringe 646 and/or has reached the distal end of syringe 646. Optionally, further rotation of driver 644 increases the stress pushing driver 644 proximally. Interference element 652 may serve as stress sensor. For example, motor 676 may supply enough torque to create a force which overcomes interference element 652.

Figure 6D:
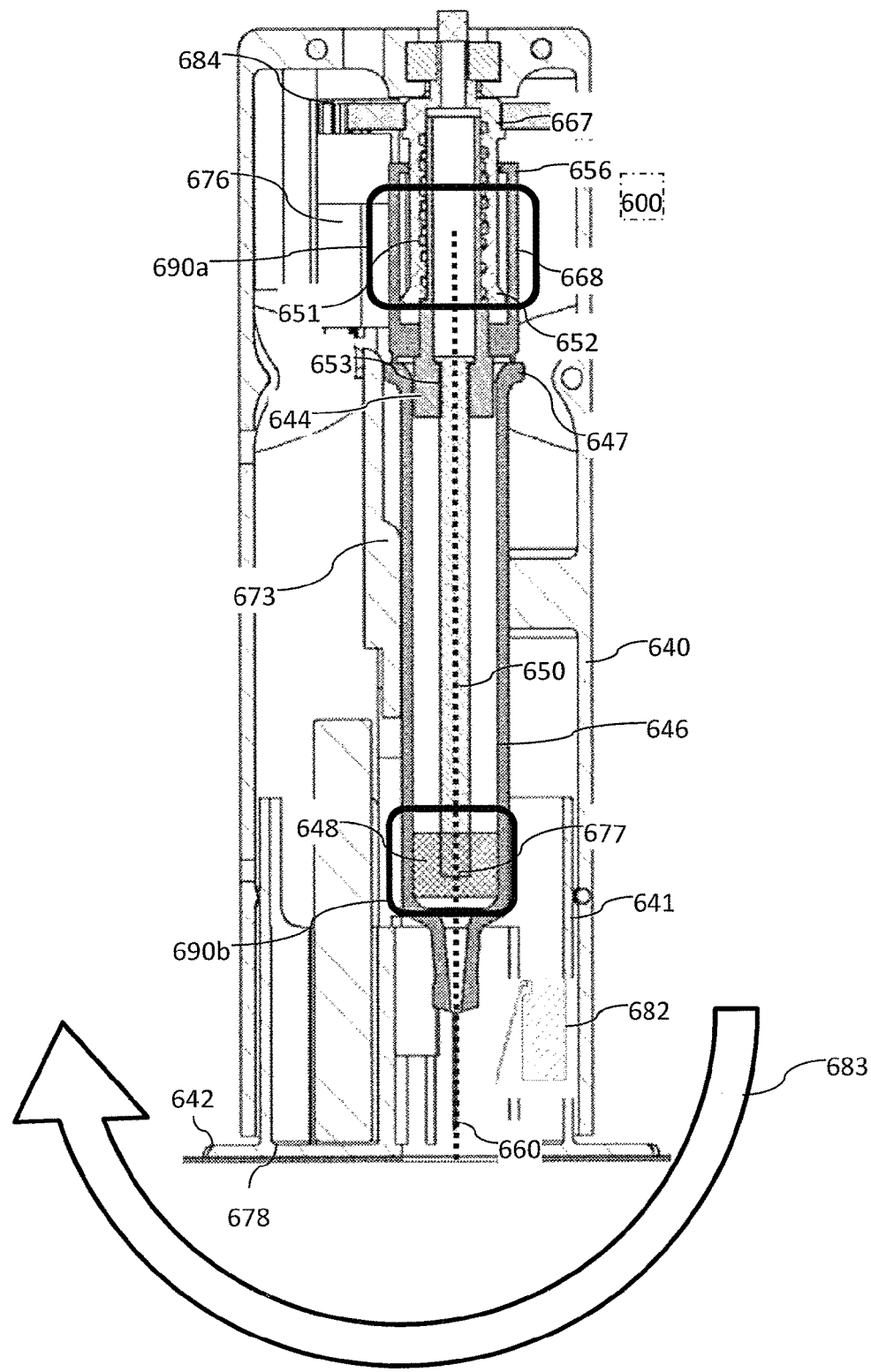

In some embodiments, once interference element 652 is overcome a course inner threading 655 in sleeve 667 rotates with respect to a course outer thread 651 of driver 644 drawing driver 644 and/or plunger 648 and/or syringe 646 and/or needle 660 proximally into a retracted state. For example, the course thread 651 has an opposite threading from the threading 653 between driver 644 and plunger rod 650. The same direction of rotation that drives plunger 648 distally before overcoming interference element 652 also draws back plunger 648 and/or syringe 646 and/or needle 660 proximally after overcoming interference element 652. Optionally needle 660 is retracted into a protected location inside housing 640 for example as illustrated in FIG. 6D. Alternatively or additionally, course thread 651 may have an the same direction of threading as threading 653 between driver 644 and plunger rod 650 and optionally rotation may be reversed to retract needle 660.

FIG. 6D is a schematic cross sectional side view illustrating injector 600 in a safe state after finishing injection. Needle 660 point has optionally been retracted into a protected location within housing 640. Syringe 646 has optionally been retracted. In exemplary injector 600, switch 682 senses that syringe 646 is retracted, as syringe 646 no longer depresses switch 682. Switch 682 may be biased off and/or raising syringe 646 may shut off motor 676.

In some embodiments one or more windows may be supplied. A user may be able to determine a status of the device by viewing for the windows. For example in FIG. 6D, injector 600 has been supplied with two windows 690a,b. For example window 690a is located such that during injection, the user views inner sleeve 667 through window 690a. When outer sleeve 668 has been retracted, it may optionally slide over inner sleeve 667. After outer sleeve 668 has been retracted, the user views outer sleeve 668 through window 690a. Optionally window 690a may serve as an indicator whether it is safe to remove the injector. For example, outer sleeve 668 may be colored green and/or driver 644 and/or inner sleeve 667 may be colored red. For example, as long as the user sees red in window 690a needle 660 tip has not been retracted and/or it is unsafe to remove the injector from the patient's skin; and/or when the user views green through window 690a needle 660 has been retracted and/or discharge has ceased and/or it is safe to remove the injector from the skin of the patient. Optionally, window 690b may be used to indicate whether an entire payload of medicine has been administered. For example, syringe 646 may be made of a transparent material. For example, during injection, the user can see the medicine through window 690b; after syringe 646 is retracted if the payload has been fully discharged then the user will view plunger 648 through window 690b. Optionally, if the user sees plunger 648 through both window 690b and outer sleeve 668 through window 690a then the user can ascertain that it is safe to remove the injector and/or that the drug was fully discharged.

In injector 600, for example, after retraction of the needle the device may be twisted such that one side of the adhesive is lifted and/or pivoted and/or peeled (as illustrated by arrow 683 in FIG. 6D) from the skin while the far edge of the base of the injector remains in contact with the skin and serves as a fulcrum.

Figure 6E:
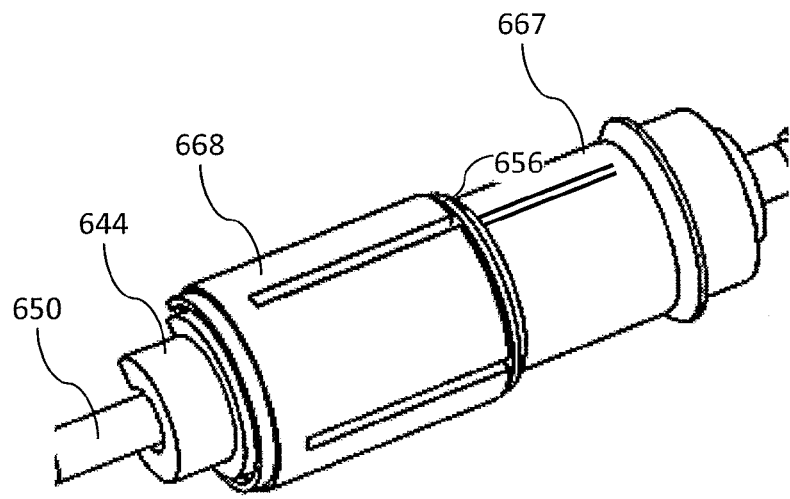
Figure 6F:
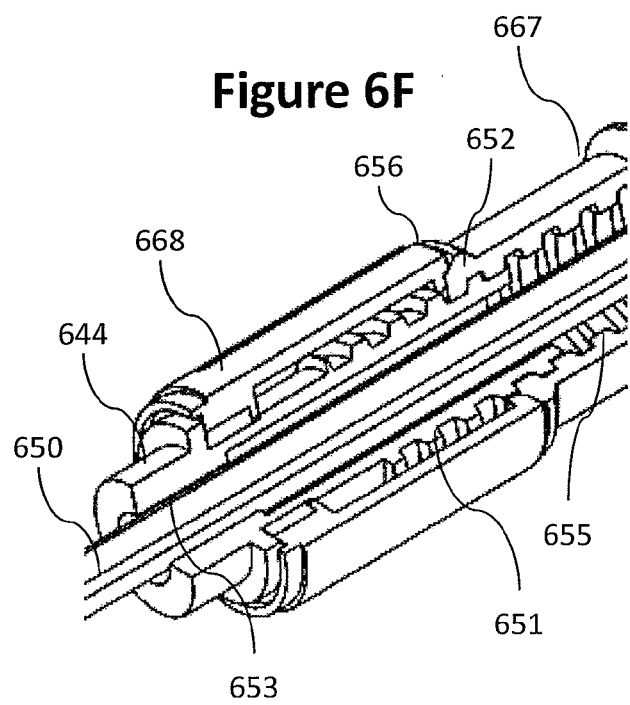

FIGS. 6E and 6F illustrate an external view and cut away view respectively of a transmission for driving discharge and retracting a needle in accordance with exemplary embodiment (for example injector 600) of the current invention. Injector 600 may optionally be designed such that, under sufficient linear stress, support 656 of external sleeve 668 deforms and/or opens to pass over resistance element 652. Optionally, coupling 684 and/or inner sleeve 667 may be formed of one or more pieces of molded plastic. Optionally outer sleeve 668 and/or driver 644 may be formed of one or more pieces of molded plastic.

FIG. 6F, illustrates details of a rotary needle retractor in accordance with an embodiment of the current invention. FIG. 6F illustrates driver 644 before needle retraction (for example in a secured state, an enabled state and/or an active state). In the exemplary embodiment, driver 644 is engaged by a set of fine screw threads 653 to rod 650. In the exemplary embodiment, driver 644 is engaged by a set of course screw threads 651, 655 to inner sleeve 667. Optionally, course screw threads 651, 655 are threaded in an opposite sense from fine screw threads 653.

In the exemplary embodiment, prior to needle retraction, sleeve 667, 668 and driver 644 are prevented from sliding longitudinally with respect one another. While sleeves 667, 668 and driver 644 are prevented from relative longitudinal movement, threads 651 and 655 prevent inner sleeve 667 and driver 644 from rotating with respect to one another.

In some embodiments, motor 676 drives coupling 684 to rotate inner sleeve 667. Optionally, before needle retraction, rotating inner sleeve 667 rotates driver 644. The sense of screw threads 653 and the rotating direction of motor 676 are optionally chosen such that rotating driver 644 relative to rod 650 pushes rod 650 and/or plunger 648 distally, optionally discharging a drug.

When plunger 648 has reached the distal end of syringe 646, rod 650 is prevent from further distal movement. Torque applied to driver 644 produces a strong proximal stress on driver 644 and/or outer sleeve 668. The strong proximal stress overcomes and/or releases interference element 652. Once interference element 652, is released outer sleeve 668 and/or driver 644 can move longitudinally with respect to inner sleeve 667. Further rotation of inner sleeve 667 rotates sleeve 667 with respect to driver 644. The sense of screw threads 655 and 651 and the rotating direction of motor 676 are optionally chosen such rotating driver 644 relative to sleeve 667 draws driver 644 and/or rod 650 and/or plunger 648 and/or syringe 646 and/or needle 660 proximally, optionally retracting needle 660. Optionally the pitch of screw threads 651, 653 and/or 655 can be tuned to achieve a desired rate of medicine discharge and/or needle retraction for a given rotation rate of the motor. In some embodiments, as rod 650 and/or plunger 648 are drawn proximally, friction between plunger 648 and syringe 646 draws syringe 646 and/or needle 660 proximally. Alternatively or additionally, outer sleeve 668 may be attached to syringe 646. Drawing back on driver 644 may draw outer sleeve 668 and syringe 646 back with it. In some embodiments additional threaded elements may be added to produce a multi-part telescoping assembly for extending plunger 648 to discharge medicine and/or for retracting needle 660. In some embodiments some or all of rod 650, inner sleeve 667, and/or outer sleeve 668 and/or coupling 684 may be formed of molded plastic and or other materials.

7 Stabilized Pen Injector

FIGS. 7A-H illustrate a drug delivery device including a stabilized injector 700 in accordance with some embodiments of the present invention. Exemplary injector 700 is an automated injection device in some ways similar to a pen injector. Optionally injector 700 may be loaded with a standard type syringe 646 and/or hypodermic needle 660. Optionally syringe 646 may be supplied loaded with medicine and/or covered with a sterile needle cover 791. Syringe 646 may be loaded into injector 700 with in a sterile state with needle cover 791 in place. Injector 700 may include for example an adhesive 678 base 642. In some embodiments, adhesive 678 base 642 may assist a user to hold injector 700 steady on the skin of a patient for an extended period. For example, injector 700 may be used to give injections of volume ranging between 0.5 and 3.0 ml over a time period ranging between 30 sec to 180 sec.

Figure 7A:
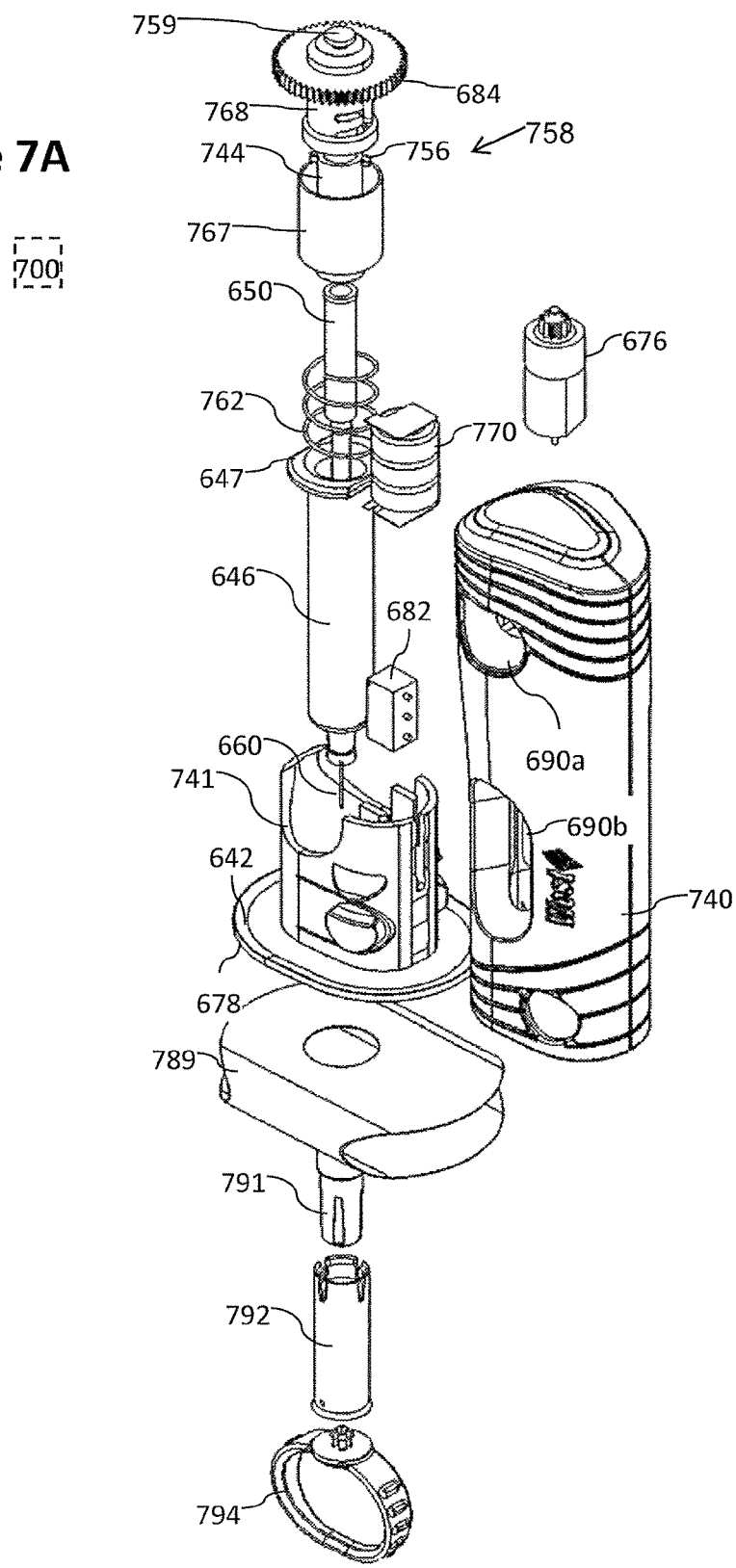
FIGS. 7A-K are detailed illustrations of an alternative stabilized injector in accordance with an embodiment of the present invention.

FIG. 7A illustrates an exploded view of injector 700. Some components of the exemplary embodiment of injector 700 which are similar to corresponding parts of the exemplary embodiment of injector 600 are marked with the same number as the corresponding parts of the exemplary embodiment of injector 600.

In the exemplary embodiment of injector 700 a power supply (for example batteries 770) may optionally supply power to gear motor 676. FIGS. 7A,B illustrate flange 647 of syringe 646. Optionally flange 647 has at least one non-rounded edge which may be held inside an autoinjector (for example autoinjectors 400, 600 and/or 700) preventing rotation of syringe 646. Outer housing 740 and/or shield 741 of injector 700 are similar to outer shell 640 and/or shield 641 of injector 600.

Some embodiments of a stabilized autoinjector (for example as illustrated in injector 700 but optionally included in injectors 600 and/or embodiments 400 and/or 200 and/or 100) may include a safety cover and/or an adhesive protector and/or a handle. Details of an exemplary embodiment of an adhesive protector 789 and/or a handle 794 and/or a needle cover remover, for example a safety cover 792 are illustrated in FIGS. 7C-H.

Figure 7B:
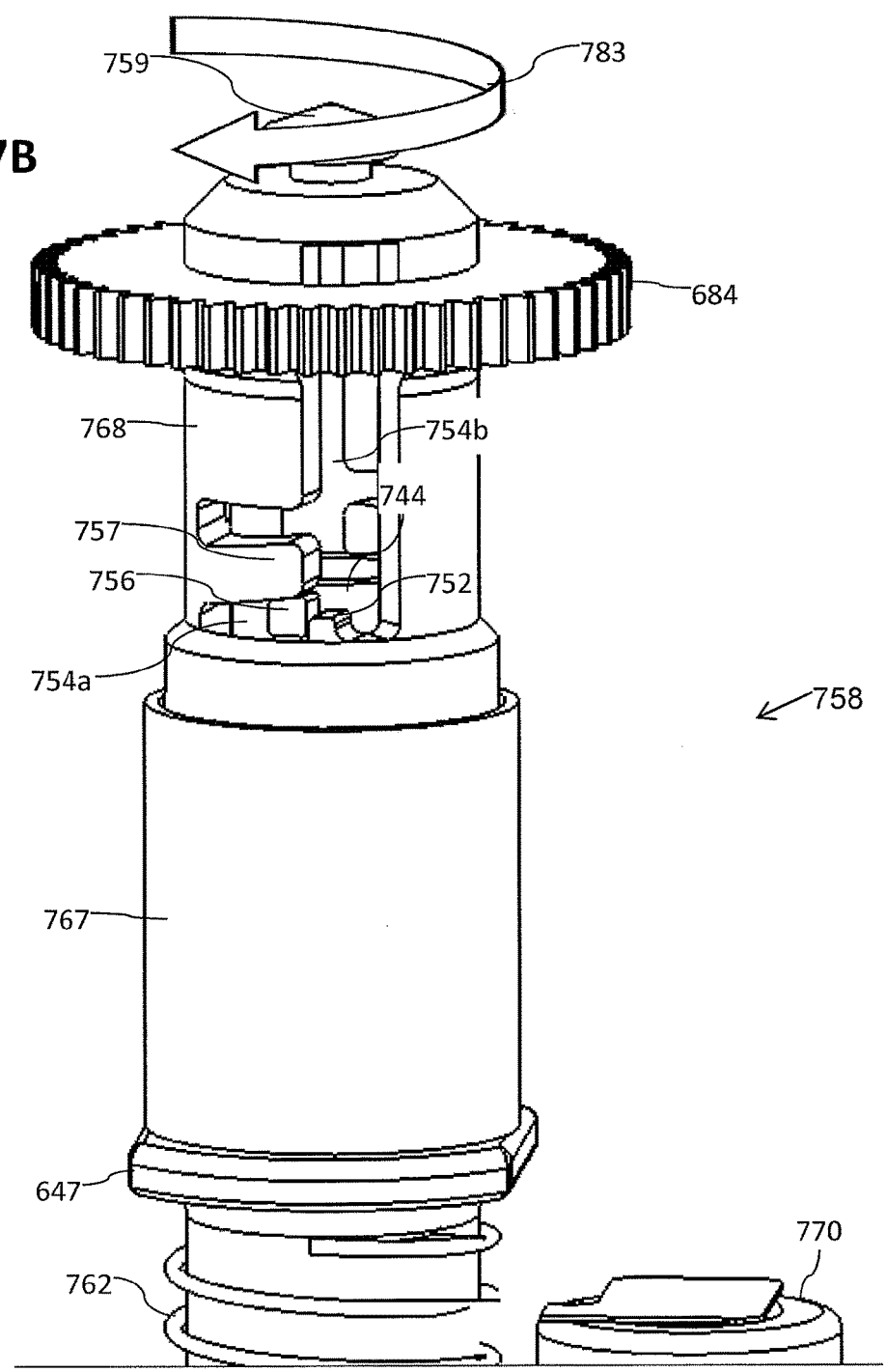

FIG. 7B illustrates an exemplary transmission including a retraction mechanism 758. Retraction mechanism 758 is optionally activated by a combination of torque and linear stress. For example retraction mechanism 758 is optionally activated may when plunger 648 is blocked for example when it reaches the end of injection (for example as described in regards to FIGS. 6A-D and/or due to an occlusion of needle 660).

In some embodiments, during drug discharge a motor (for example motor 676) rotates coupling 684 in the direction of arrow 783. Coupling 684 may optionally be rigidly connected to and/or integrally molded with inner sleeve 768. Rotating coupling 684 may also rotate inner sleeve 768. A pin 756 protrudes from driver 744 into a nearly lateral slot 754a in sleeve 768. While pin 756 is in slot 754a, driver 744 is prevented from moving longitudinally with respect to inner sleeve 768. In some embodiments syringe 646 is supported (from moving proximally) by driver 744.

In some embodiments, when there is a strong linear force on driver 744 in the proximal direction and/or there is a strong torque on sleeve 768 in the direction of arrow 783, arm 757 is deflected upward and pin 756 slides past an interference element 752 into a longitudinal slot 754b. In slot 754b pin 756 may slide longitudinally (in the proximal direction). A geometry of pin 756 and/or interference element 752 may be chosen to achieve a desired resistance to movement. For example, pin 756 and/or interference element 752 may have a squared side, a flat side, a rounded side etc.

In some embodiments, a spring (for example spring 762) biases syringe 646 in the proximal direction. For example spring 762 may apply a proximal force to flange 647. Optionally another biasing element may be used in place of spring 762. For example, a biasing element may include a stretched element (for example a rubber band and/or a twisted elements and/or a deflected plastic element).

Optionally when pin 756 enters longitudinal slot 754b, spring 762 pushes syringe 646 and/or outer sleeve 767 and/or needle 660 and/or driver 744 and/or pin 756 proximally, retracting needle 660. Optionally, needle 660 may be held in the retracted position by spring 762. Alternatively or additionally a locking mechanism may be included to lock needle 660 in the retracted position, for example, a one way catch and/or an interference element may lock against syringe 646 as it is retracted and/or against pin 756 in slot 754b. Optionally, in injector 700 driver 744 includes two molded plastic telescoping pieces. One piece is optionally integrally molded with outer sleeve 767. Optionally, sleeve 767 and/or driver 744 may be made as a single piece and/or multiple parts. They may be formed of plastic and/or another material and/or they may be molded and/or formed by another process.

Figure 7C:
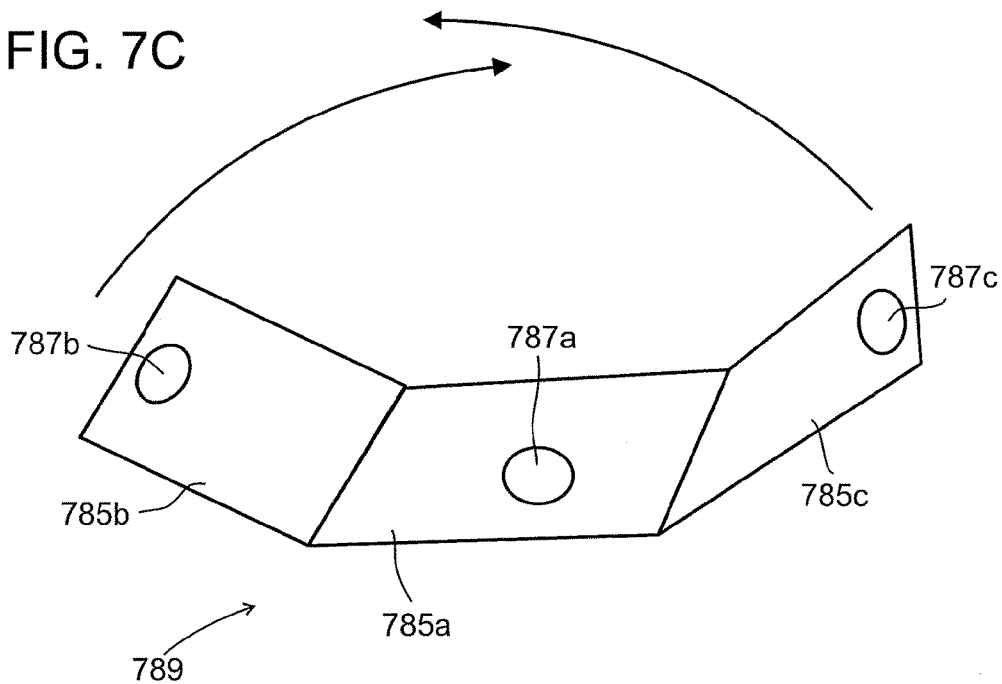
Figure 7D:
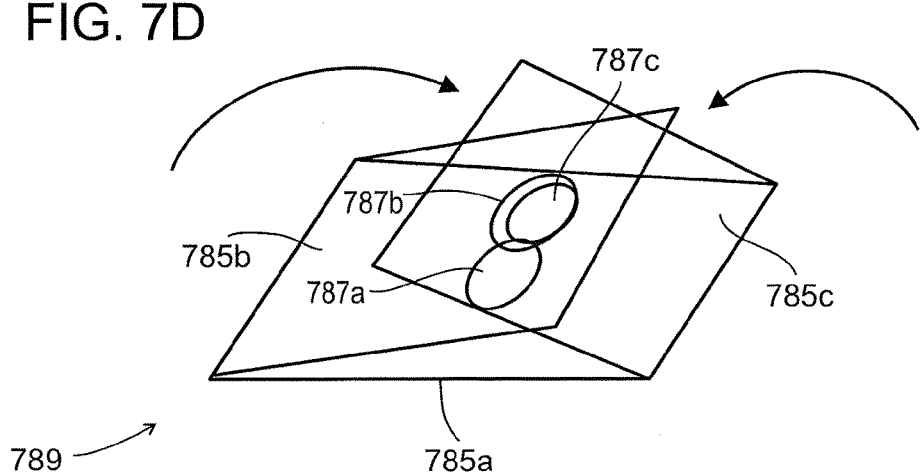

FIGS. 7C and 7D illustrate an exemplary method of folding adhesive protector 789. For example, adhesive protector may include three folded portions 785a, 785b, and 785c. For example, adhesive protector may include three holes 787a, 787b, and 787c. When folded, the side portions 785b,c may fold over the center portion 785a. Side holes 787c,b may line up with center hole 787a. Alternatively or additionally, an adhesive protector may have only one fold and/or one side portion and/or peeling may be from one side only.

In some embodiments, portion 785a will be adhered to base 642 with the needle opening accessible through holes 787a-c. A safety cover (for example cover 792) may protrude through holes 787a-c. The safety cover may optionally be connected to portions 785b,c. The safety cover may pass freely through hole 787a and/or not be connected to portion 785a of adhesive protector 789.

FIGS. 7E-H illustrate removal of an exemplary safety cover 792, needle cover 791 and/or adhesive protector 789. For example, while safety cover 792 is mounted to needle cover 791, safety cover may prevent deployment and/or activation of the injector. For example, safety cover 792 and handle 794 may supply a convenient means of removing needle cover 791 and/or adhesive protector 789.

Figure 7E:
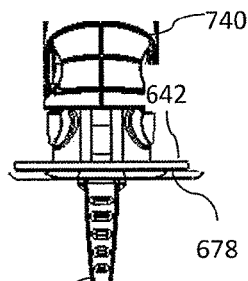

FIG. 7E illustrates injector 700 in a safe state for storage and/or transport. Needle cover 791, safety cover 792 and adhesive protector 789 are in place. Adhesive protector 789 is folded for example as illustrated in FIGS. 7C,D. Needle cover 791 (not seen in the drawing) may optionally preserve the sterility of needle 660. Safety cover 792 surrounds and grasps needle cover 791. Safety cover 792 may prevent inadvertent activation of the injector and/or protect users from a needle stick hazard.

Figure 7F:
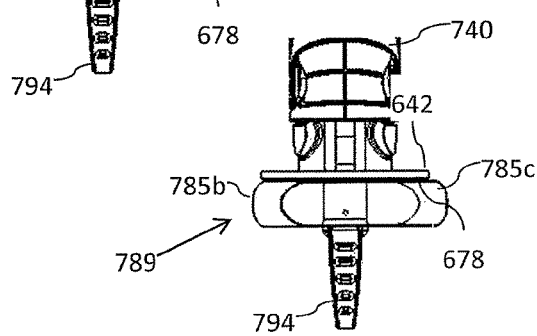

FIG. 7F illustrates the beginning of removal of safety cover 792. A user pulls handle 794 away from needle 660. Handle 794 pulls needle cover 791 out the needle hole and/or needle aperture of injector 700 and through hole 787a. As cover 792 is pulled away from base 642, portions 785b,c of adhesive protector unfold while portion 785a remains adhered to base 642.

Figure 7G:
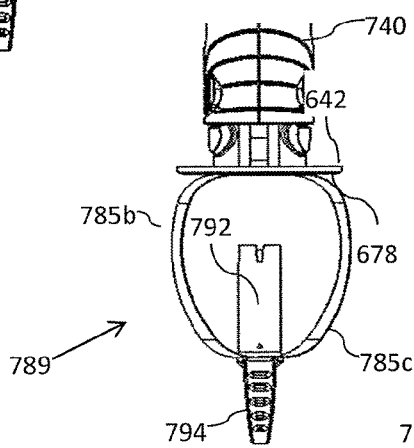

FIG. 7G illustrates that as safety cover is pulled further away from base 742 portions 785b,c of adhesive protector 789 pull and/or pivot and/or peel portion 785a away from base 742.

Figure 7H:
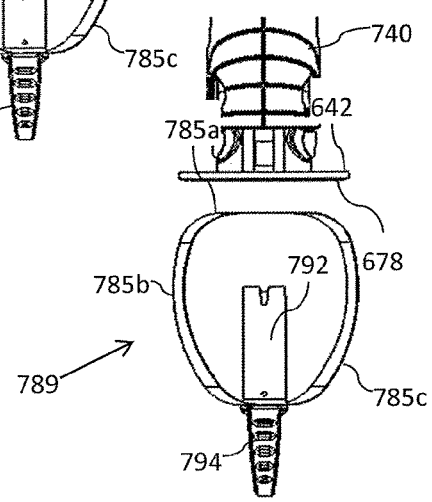

FIG. 7H illustrates cover 792 and protector 789 fully removed from injector 700, such that injector 700 is enabled and/or ready to adhere to a patient and/or ready for activation.

Figure 7I:
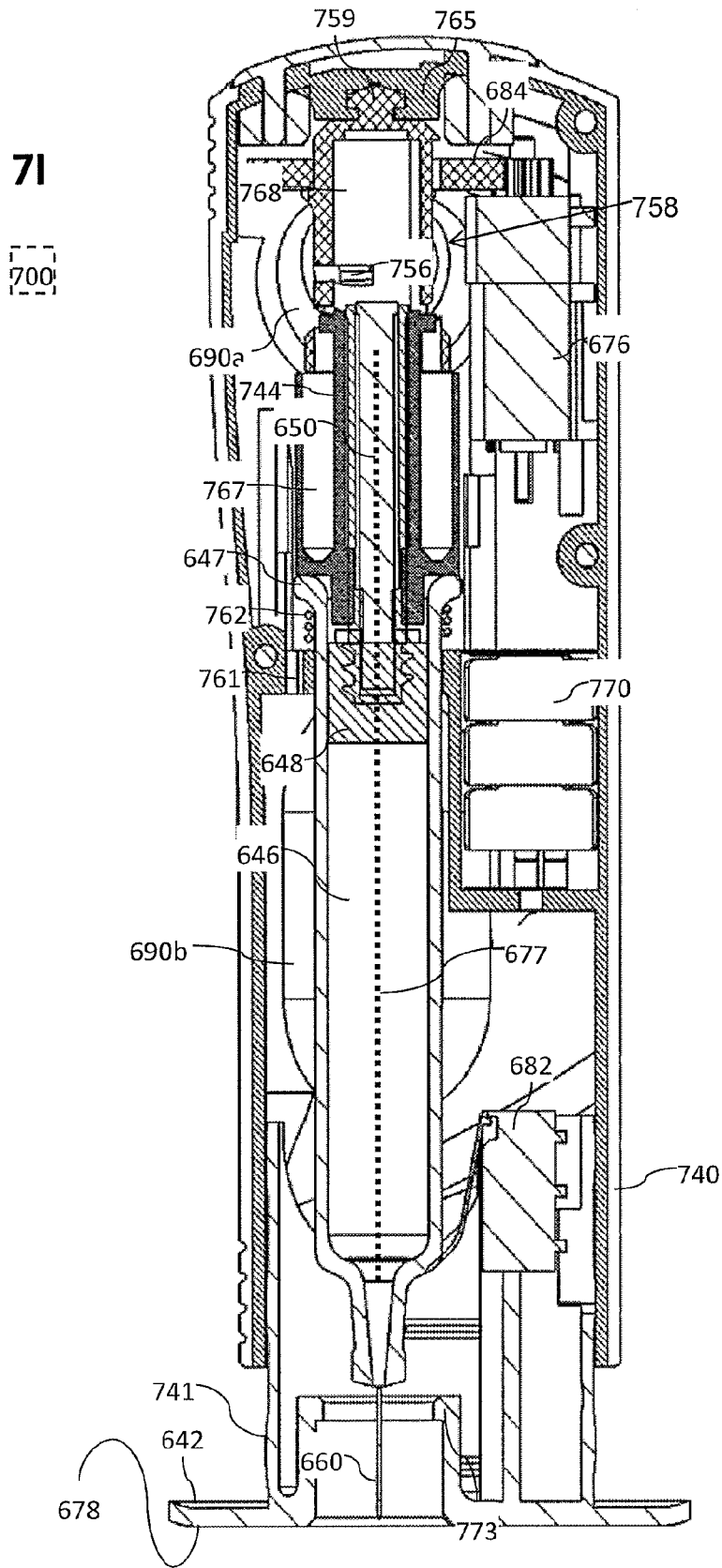

FIG. 7I illustrates exemplary embodiment 7I assembled and/or in an enabled state before insertion of needle 660 into a patient. FIG. 7I illustrates various optional details and/or supporting structures for syringe 646 and/or plunger.

In injector 700, syringe 646 is held to outer housing 740 by a socket 761. Socket 761 allows syringe 646 to slide axially with respect to housing 740 but not to move laterally. In injector 700, coupling 684 is held rotatably fixed to housing 740 by bearing 759 in a hub 765.

Figure 7J:
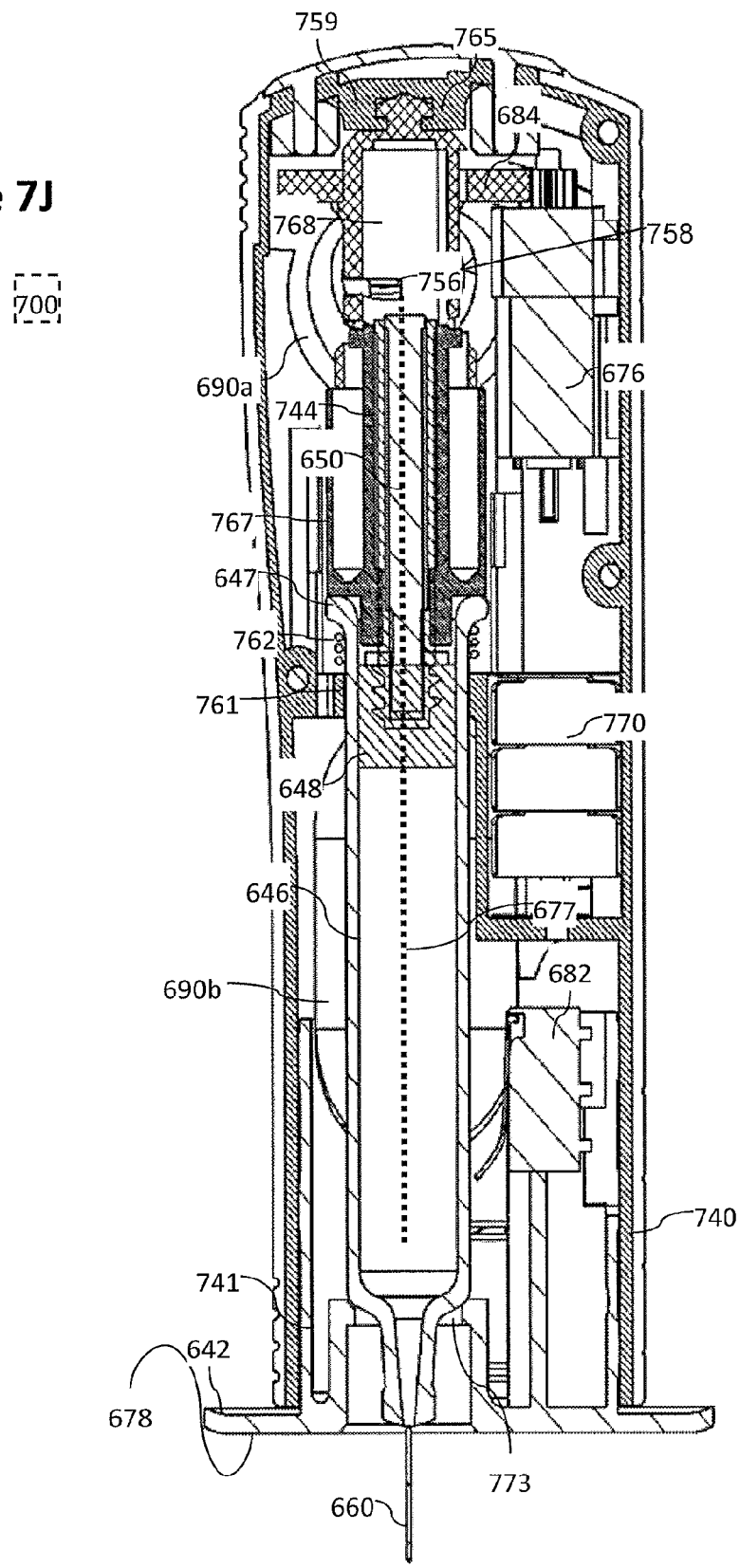

FIG. 7J illustrates exemplary injector 700 in an active state. For example when the injector is in the enabled state, a user may place adhesive against the skin of a patient and push downward (distally) on housing 740. Housing 740 and its contents (for example syringe 646, coupling 684, locking assembly 758 etc.) along with needle 660 are all pushed distally along the axis of needle 660. As needle 660 moves distally, the needle tip passes through a hole in shield 741. For example, in operation, needle 660 may protrude from injector 600 into a patient. Optionally, in operation, needle 660 may be in fluid communication with syringe 646 and/or the patient. For example needle 660 may supply a fluid pathway for discharging medicine directly from syringe 646 through needle 660 into the patient.

In some embodiments, when needle 660 is in the extended position, the front end of syringe 646 seats into a bracket 773. Bracket 773 may optionally hold syringe 646 steady and/or prevents further longitudinal movement and/or prevent lateral movement with respect to housing 740.

Figure 7K:
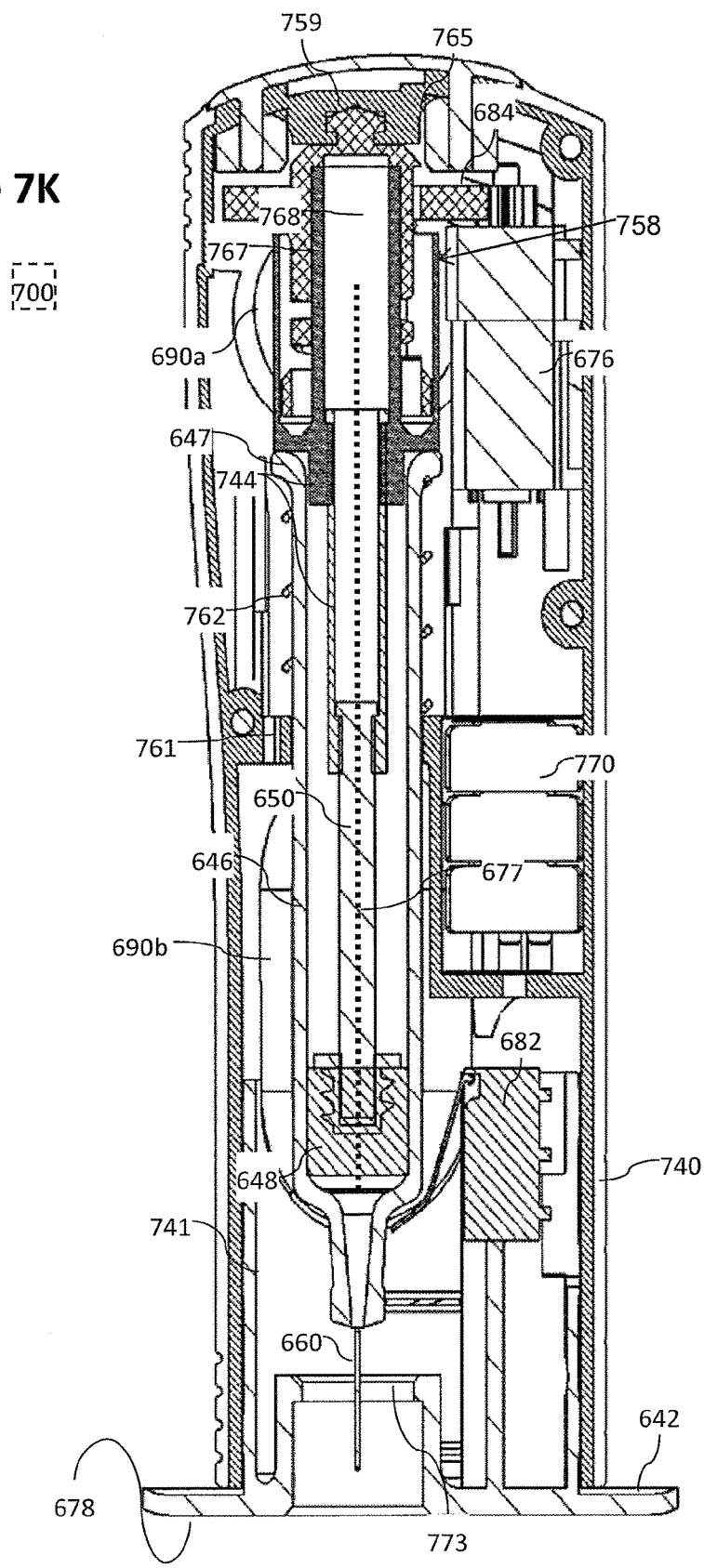

FIG. 7K illustrates injector 700 after needle retraction. Optionally driver 644 includes a telescopic assembly, which is shown in an extended state in FIG. 7K. Optionally, after retraction of needle 660, the entire device may be twisted to pivot and/or peel adhesive 678 from the skin.

Various aspects or features illustrated herein with respect to a particular embodiment may be combined with other embodiments. For example, needle 460 and 560 of embodiment 400 and 500 are shown mounted at an angle to base 442 or 542. Alternatively or additionally they may be perpendicular to the base. For example, needles 660 of embodiments 600 and 700 are shown perpendicular to base 642. Alternatively or additionally they may be at an angle to the base. Needle covers and/or protective covers illustrated in one embodiment may be used with another embodiment. Retraction mechanisms illustrated in one embodiment may be used with another embodiment. A clip, an interference element, a catch and/or another locking mechanism may hold an injector in one or another state. For example an interference element may hold a needle in a retracted position and/or in the extended position.

8 Method of Manufacture of a Stabilized Pen Injector

Figure 8:
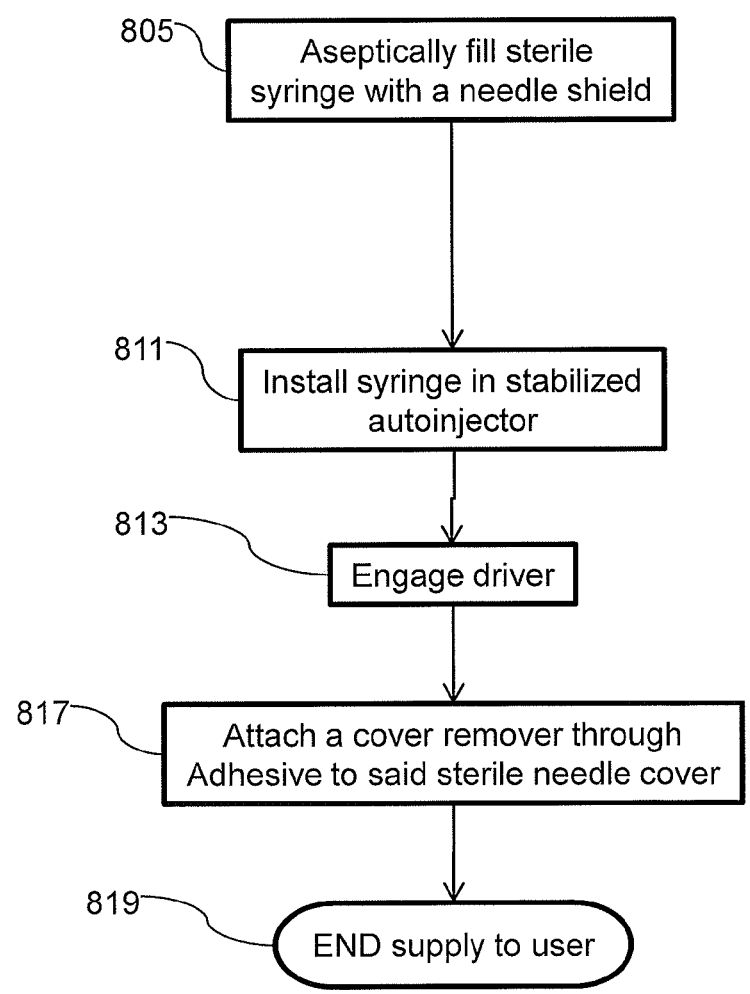
FIG. 8 is a flow chart illustration of a method of manufacture of a stabilized pen injector in accordance with an embodiment of the present invention.

FIG. 8 is a flow chart illustration of a method of manufacture of a stabilized pen injector in accordance with an embodiment of the present invention. In the method a preloaded sterile syringe and needle may optionally be installed into an autoinjector for direct injection into a patient. For example the method of manufacture illustrated in FIG. 8 may optionally be used in manufacturing one, some and/or any of the embodiments of an injector illustrated herein above and/or below.

In some embodiments a syringe is preloaded 805 with a medicine. For example the volume of preloading medicine may range between 0.5 and 1 ml and/or between 1 and 5 ml and/or greater than 5 ml of medicine. Preloading 805 may optionally be performed on standard syringe equipment and using standard filling procedures. Optionally the syringe may be a standard type syringe. For example preloading may be done in an aseptic environment. Optionally, a sterile needle and/or needle cover may be attached before filling the syringe. For example, the syringe may be filled while attached to a sterile needle and/or a sterile needle cover. Alternatively or additionally, the syringe may be attached to a sterile needle and/or a sterile needle cover while being filled and/or after being filled. Sterility of the needle may optionally be protected by a needle cover (for example cover 791).

In some embodiments, the preloaded syringe with the sterile, protected needle may be installed 811 in an autoinjector including an adhesive stabilizer (for example one of the autoinjectors described herein above). Optionally, installing 811 the syringe may include engaging 813 a driver to a power source, for example a battery (for example directly and/or via a motor and/or coupling and/or a transmission) and/or a mechanical power source for example a spring.

In some embodiments, the fluid path of the injector may include the medicine container and/or the needle. For example, in operation, medicine stored in the container may pass directly from the container to the needle and/or from the needle directly to the patient. Optionally, the entire fluid path may be in a complete and/or sterile and/or assembled and/or protected state prior to and/or during filling of the container. For example, a syringe medicine container and/or needle may be filled and sealed under aseptic and/or sterile conditions, for example in an aseptic room. For example the syringe may be sealed by a needle cover and/or a plunger. Optionally, the syringe, with the fluid path in a sealed and/or protected state may be taken from the aseptic filling room and installed into an injector. Optionally, the fluid path may not require sterilization after being removed from the filling room and/or after installation into the injector.

In some embodiments, a cover remover (for example safety cover 792) may be attached 817 to the needle cover through a hole in the adhesive. In some embodiments, the hole in the adhesive may be surrounded by the adhesive. Alternatively or additionally, the hole may be surrounded by the adhesive on two sides and/or on three sides. For example, the adhesive may be made of two pieces, one piece on one side of the hole and another piece on another side of the hole. The autoinjector may then be ready to be supplied 819 to a user. For example the user may use the cover remover to remove the needle cover and/or to enable the injector.

9 Stabilized Injector Dimensions

Figure 9:
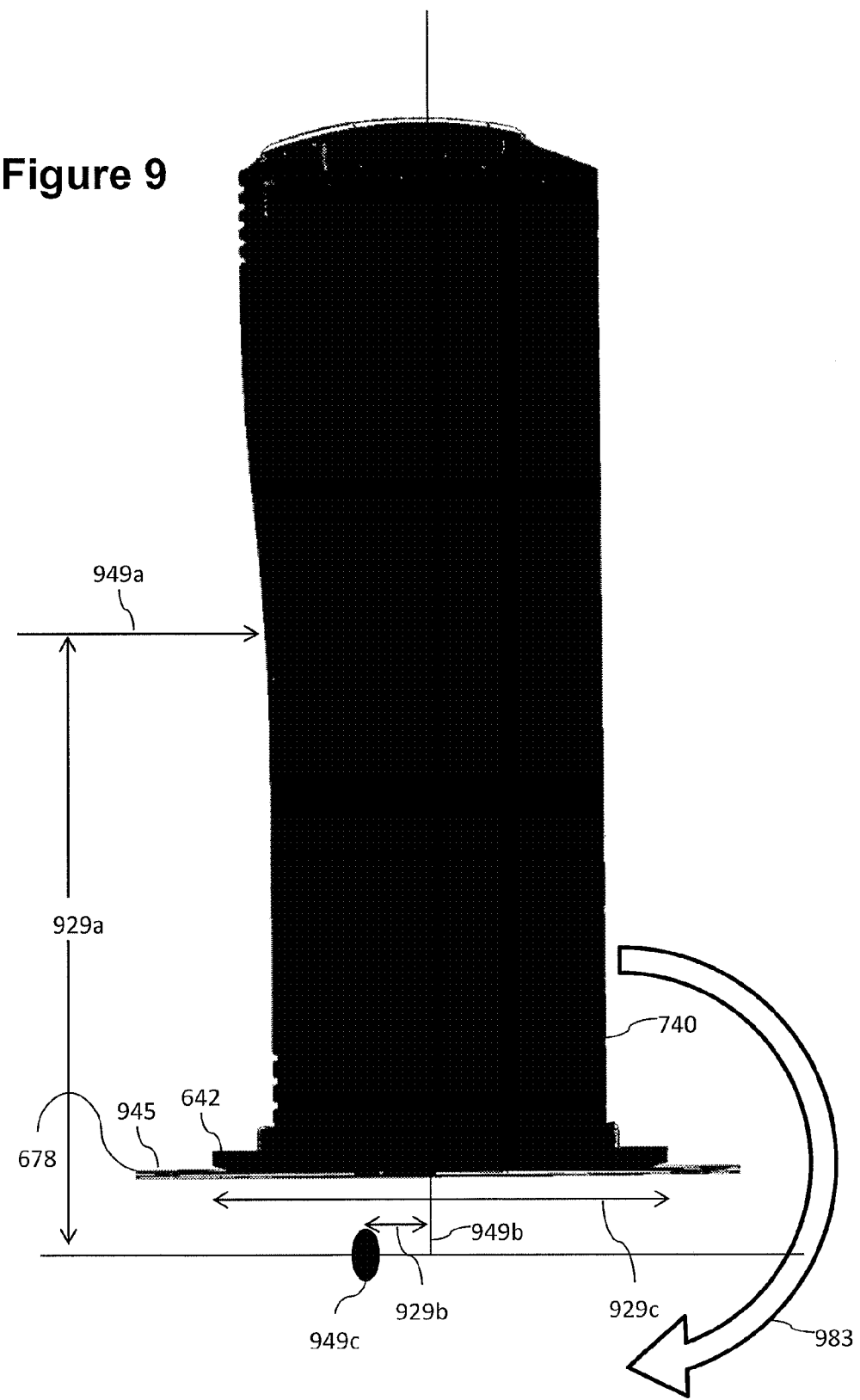
FIG. 9 illustrates an external view of a stabilized injector in accordance with an embodiment of the current invention.

FIG. 9 illustrates an external view of a stabilized injector drug delivery device in accordance with an embodiment of the current invention. In FIG. 9 exemplary dimensions are shown to help understand the relationship between the size and weight of the injector and the strength and geometry of the adhesive. For example, any, some and/or all of the features and/or dimensions described herein below may apply to any, some and/or all of the embodiments described herein above.

In some embodiments, the height of an autoinjector (perpendicular to the adhesive layer) may be greater than then width of the adhesive layer (for example the height may be greater than the greatest length between any two points on the adhesive layer). For example, the distance 929a from the longitudinal center of mass 949a of the injector and the adhesive surface 678 may range for example between 50±10 mm and/or the longitudinal center of mass may range for example between 60 and 80 mm from the adhesive. In some embodiments, the longitudinal center of mass may be greater than for example between 80 mm from the adhesive. The distance 929b between the lateral center of mass 949b of the injector and the center of adhesion 949c on the base of the apparatus (when the weighted center of force on the adhesive when the injector is twisted off the skin in the direction of the arrow 983 in FIG. 9) may range, for example between 12.5±4 mm. The width 929c of base 642 may range, for example, between 60±15 mm. There may optionally be a semi-stiff skirt 945 extending beyond the edge of base 642 for example between 0 to 2 mm and/or embodiments skirt 945 may extend for example between 4 to 10 mm beyond base 642. In some embodiments, the width of skirt 945 may vary at various points around base 645. (For example the skirt may be made of plastic, for example Polyethylene terephthalate (PET) and/or Polycarbonate and/or ABS. The thickness may range for example between 0.1 to 0.8 mm.). The thickness of adhesive layer 678 may range between 0.1 and 1 mm. An injector may weigh for example 50±20 g. Then the resting torque adhesive when the injector is adhered to a vertical object will be approximately 50 mm×50 g=2500 g×mm. The strength of adhesion necessary to hold the injector to the patient will be approximately 2500 g×mm/12.5 mm=200 g. In some embodiments, movements of the user may place a considerably stress on the injector than the static stress. For example an adhesive may be provided to give a total adhesive strength ranging between 500 to 1500 g.

In some embodiments, the adhesive will be less strong and/or maybe easier to remove. For example the strength of the adhesive may be less than 500 g (for example the user may have to hold the injector with his hand to prevent it from falling, especially when the user is moving). Alternatively or additionally the adhesive may not include semi-stiff skirt 945.

10 Microswitch Activator for an Autoinjector

FIGS. 10A-D is are cutaway illustrations of an exemplary embodiment of an autoinjector 1000 drug delivery device including a motor switch located in the main body of the injector in accordance with some embodiments of the current invention. Optionally the motor switch remains stationary with respect to the housing of the autoinjector, for example housing 640, and/or with respect to and/or a motor and/or a power source, for example batteries 1070. When an activator of the injector is triggered (for example by collapsing a shield 1041), movement of the activator may activate the switch. When the needle 660 is retracted and/or shielded (for example after injection), the switch is optionally returned to the inactivated state. Keeping a switch stationary with respect to a motor and/or power source may simplify assembly of the auto injector.

Figure 10A:
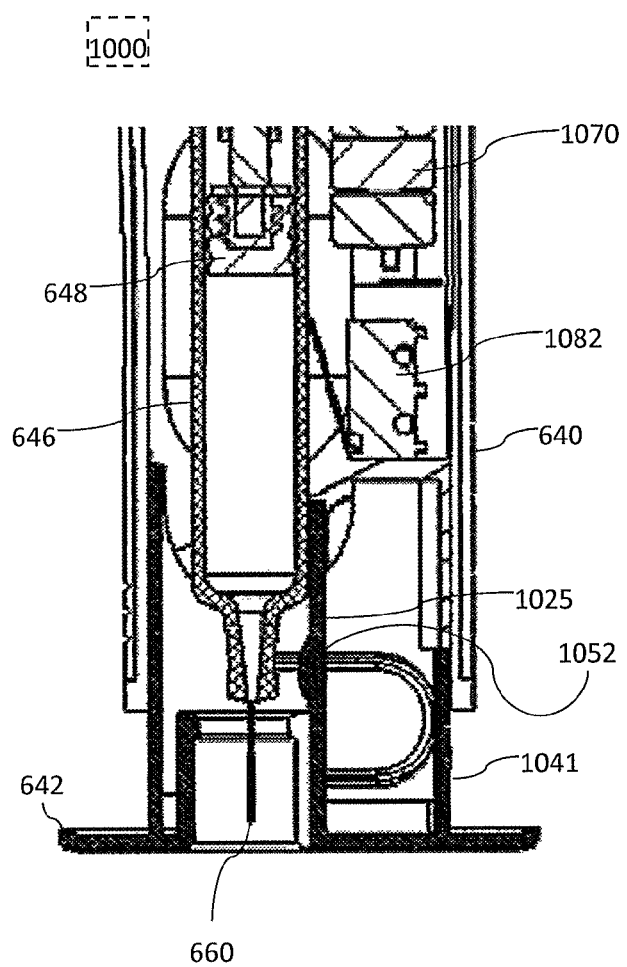
FIG. 10A-D are crossectional views illustrating a microswitch activator for an autoinjector in accordance with some embodiments of the current invention.

FIG. 10A illustrates injector 1000, prior to activation in accordance with an embodiment of the current invention. Optionally many structures are the same as other embodiments listed herein above or below, for example, injector 1000 may include the advancement and/or retraction mechanism of injector 600. Optionally, prior to activation, a syringe position sensor, switch 1082 senses that shield 1041 is in a deactivated position. When shield 1041 is in a deactivated position, switch 1082 optionally deactivates the motor of injector 1000.

Figure 10B:
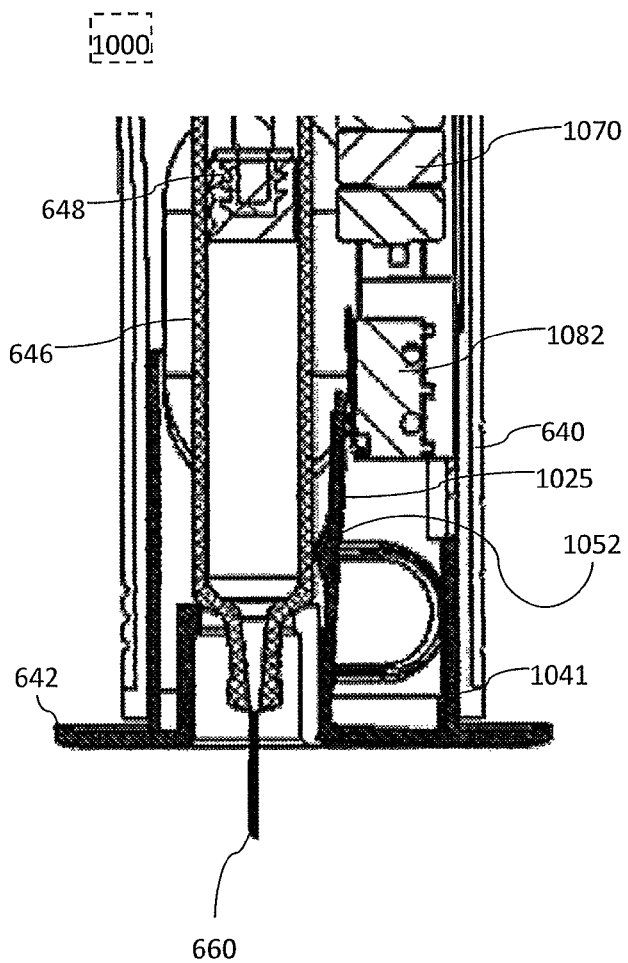

FIG. 10B illustrates injector 1000, immediately after activation in accordance with an embodiment of the current invention. In some embodiments, an injector may be activated by collapsing a needle shield 1041. Collapsing shield 1041 optionally exposes needle 660. Optionally the syringe position sensor (switch 1082) senses the new position of shield 1041. For example, shield 1041 pushes an element 1052 against a side of a syringe and/or pushes an extension 1025 of shield 1041 into switch 1082 and/or activates switch 1082 and/or activates a motor (for example similar to motor 676 of injector 600).

Figure 10C:
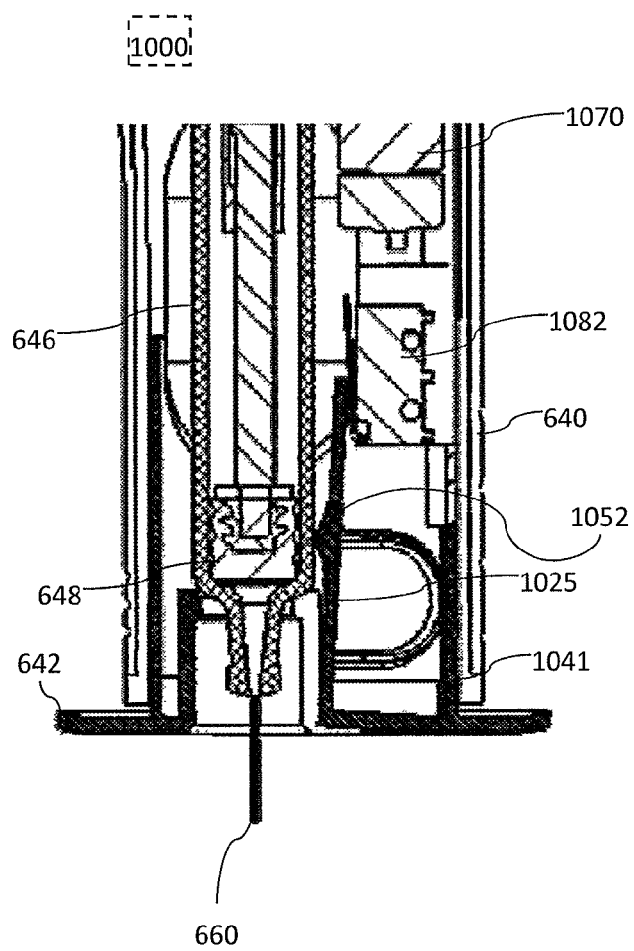

FIG. 10C illustrates injector 1000, immediately at the end of injection in accordance with an embodiment of the current invention. Optionally for as long as shield 1041 remains in a collapsed state and/or needle 660 remains in an extended state (protruding from the injector), extension 1025 continues to hold switch 1082 in an activated state and/or a motor continues to drive plunger 648. Optionally, when plunger 648 reaches the end of syringe 646 a retraction mechanism (for example retraction mechanism 758) retracts syringe 646 and/or needle 660 to a retracted state (as illustrated for example in FIG. 10D).

Figure 10D:
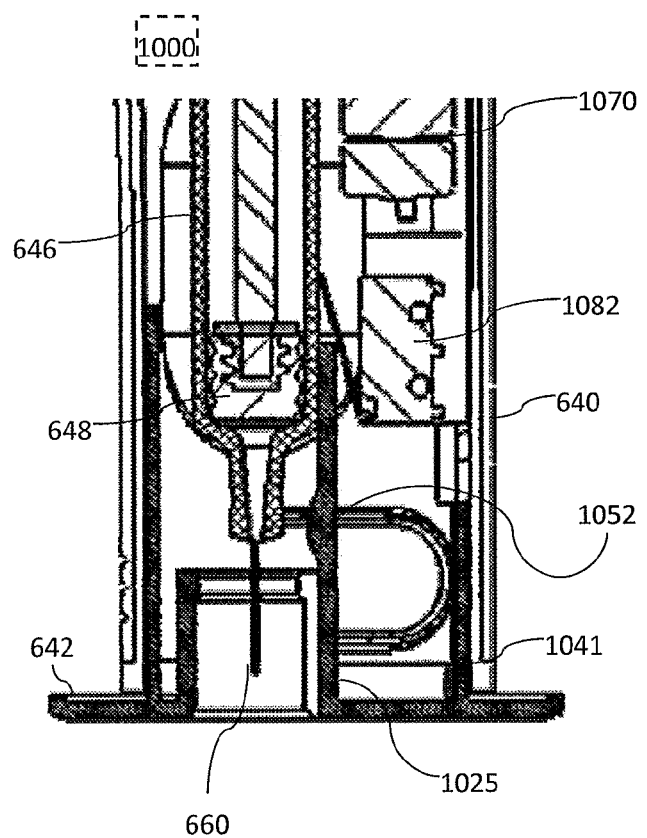

FIG. 10D illustrates injector 1000 in a retracted state in accordance with an embodiment of the current invention. Optionally, when needle 660 and/or syringe 646 is retracted, element 1052 is released and/or extension 1025 moves away from switch 1082 and/or switch 1082 moves into a deactivated state and/or the motor is switched off.

11 Method of Stabilizing an Autoinjector

Figure 11:
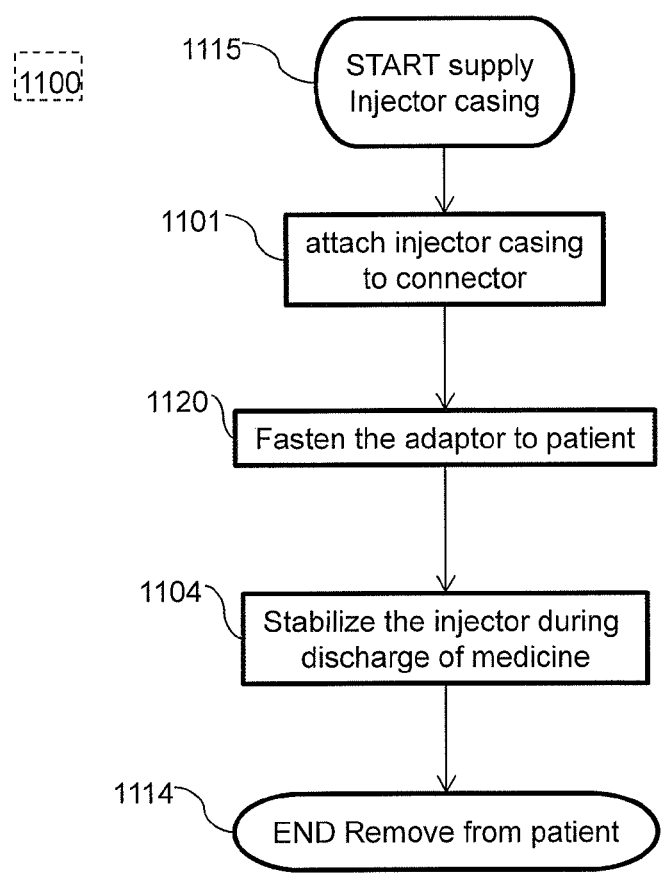
FIG. 11 is a flowchart illustration of a method of stabilizing an autoinjector in accordance with some embodiments of the current invention.

FIG. 11 is a flow chart illustration of a method 1100 of adapting an injector for extended use in accordance with an embodiment of the present invention. For example an injector may be attached to a stabilizing adaptor. Stabilization may extend use of the injector to longer injection time and/or higher viscosity medicines and/or colder conditions.

In some embodiments, an injector housing may be supplied 1115. Optionally the housing is attached 1101 to a connector. Optionally, the housing may be attached 1101 to the connector prior to assembly of autoinjector and/or prior to loading the autoinjector with medicine. For example, the autoinjector may be attached to the connector by a drug company and/or by a medical device supplier. Alternatively or additionally the injector housing may be supplied as part of an assembled autoinjector unattached to the connector. For example patient and/or a medical professional and/or a patient aid may attach 1101 the housing to the connector before use.

In some embodiments, a stabilizing adaptor may be fastened 1120 to a patient. Optionally, after attaching 1101 the injector to the adaptor, the entire assembly is fastened 1120 to the patient. For example, a patient and/or a medical professional and/or a patient aid may be supplied with a fully assembled injector and adaptor. For example the patient and/or the medical professional and/or the patient aid may fasten 1120 the assembled injector and adaptor to the patient and perform the injection. Alternatively or additionally, the adaptor may be fastened 1120 to the patient without the injector and then the injector may be attached 1101 to the adaptor while the adaptor is already fastened 1120 to the patient. For example, the adaptor may be fastened 1120 to the patient by a medical professional and/or patient aid and/or in a clinic and/or in a hospital. Later on the injector is optionally attached to the adaptor and/or enabled and/or activated, for example by the patient himself and/or a medical aid for example at home or elsewhere away from medical supervision.

In some embodiments, during discharge of the medicine, the autoinjector may be stabilized 1104 on the injection site of the patient by the adaptor.

In some embodiments, after injection ends, the injector and/or the adaptor may be removed 1114 from the patient. For example, the injector and the adapter may be removed 1114 together. Alternatively or additionally the injector may be disconnected from the adapter and removed from the patient while the adapter remains fastened to the patient, to be used for another injection and/or removed 1114 later.

12 States of an Autoinjector and Extending Adaptor

Figure 12:
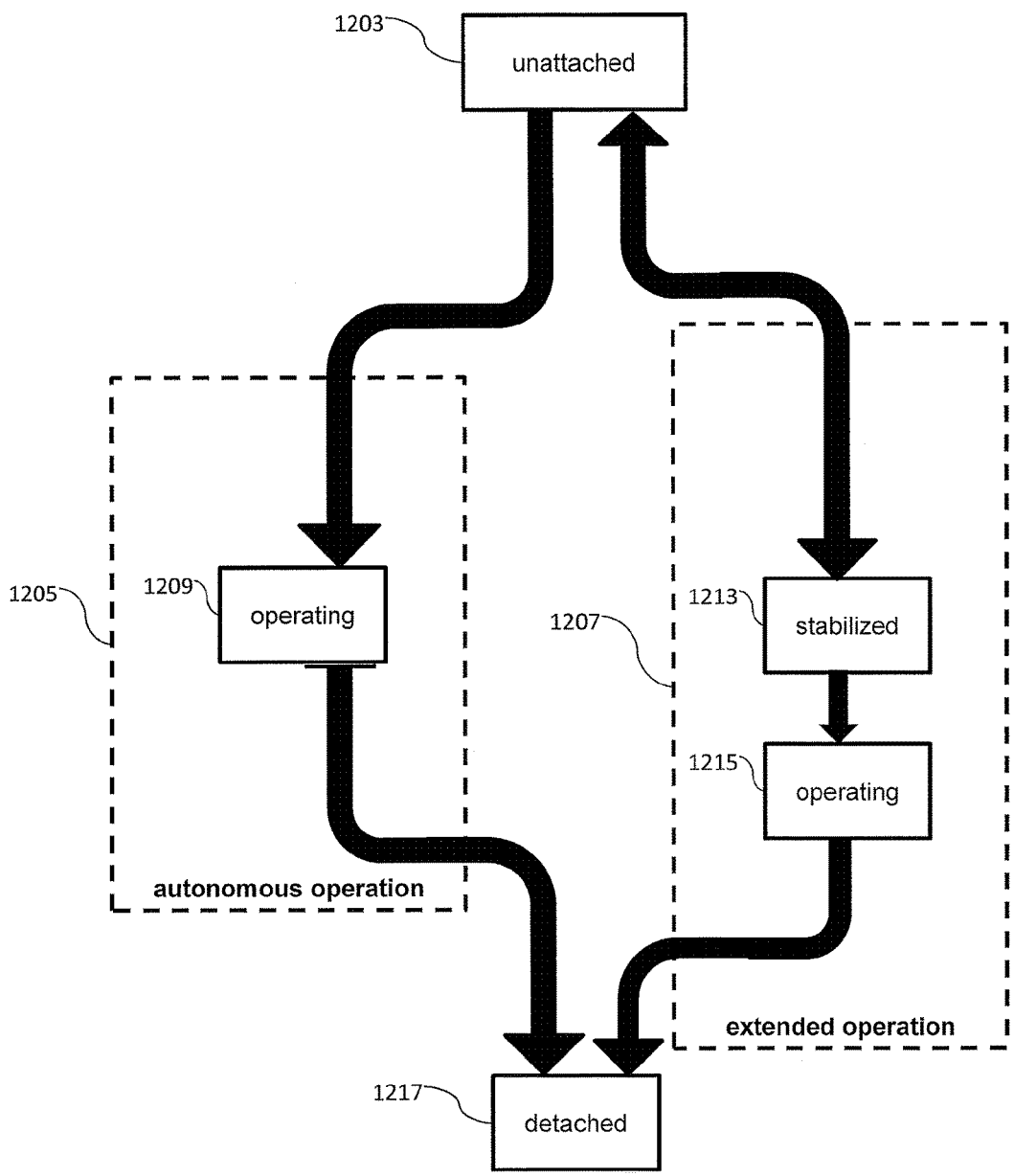
FIG. 12 is a state diagram of an autoinjector and extending adaptor in accordance with some embodiments of the current invention.

FIG. 12 is a state diagram of an autoinjector and extending adaptor in accordance with an embodiment of the current invention. An autoinjector may have two or more optional operating states. For example the injector may operate in an autonomous state 1205 and/or in an operationally extended state 1207. Operationally extended state 1207, optionally includes operation of the injector extended to longer times and/or more viscous medicines and/or larger injection volumes. In some embodiments, operational extended state 1207 may include extension of the length of the injector. Alternatively or additionally, operational extended state 1207 may not include extension of the length of the injector. Prior to use the injector may have an unattached 1203 state and/or after use the injector may have a detached 1217 state.

In some embodiments, an injector may operate 1209 in an autonomous state 1205. For example in the autonomous state the autoinjector may inject a medicine without an adaptor. Optionally in the autonomous state 1205 the injector may have a set of controls that are activated by a user in order. In the autonomous state 1205 the injector may inject a medicine in accordance with a prescribed protocol.

In some embodiments, the injector may operate 1215 in an extended state 1207. In extended state 1207, for example, an adaptor may be used to stabilize 1213 the injector on a patient. For example, the stabilized configuration may allow injection for longer periods of time and/or for a more dexterity limited patient. In the extended state 1207, operation 1215 is optionally activated by the same set of controls and/or in accordance with the same protocol as in operation 1209 in the autonomous state 1205. For example, for a higher viscosity medicament (for example a medicament at a lower temperature) using the same controls and protocol, the injector may require a longer time to discharge its payload. For example, extended operation 1215 may be very useful when an injector has been tested and/or approved for operation 1209 in the autonomous state 1205, but under some conditions (for example when the medicine is cold) the injector does not meet certain requirements. For example, the injector requires more than the maximum approved time to discharge its payload. Adding the adaptor optionally makes minimal changes in the user interface and/or operation protocol of the injector, while allowing extended operation 1215. Thus, for example with the adaptor may allow use of the injector in extended operation 1215 under extended conditions with reduced testing and/or approval while taking advantage of previous testing and/or regulatory approval of autonomous operation 1209 under more limited conditions.

13 Block Diagram of an Autoinjector and a Stabilizing Adaptor

Figure 13:
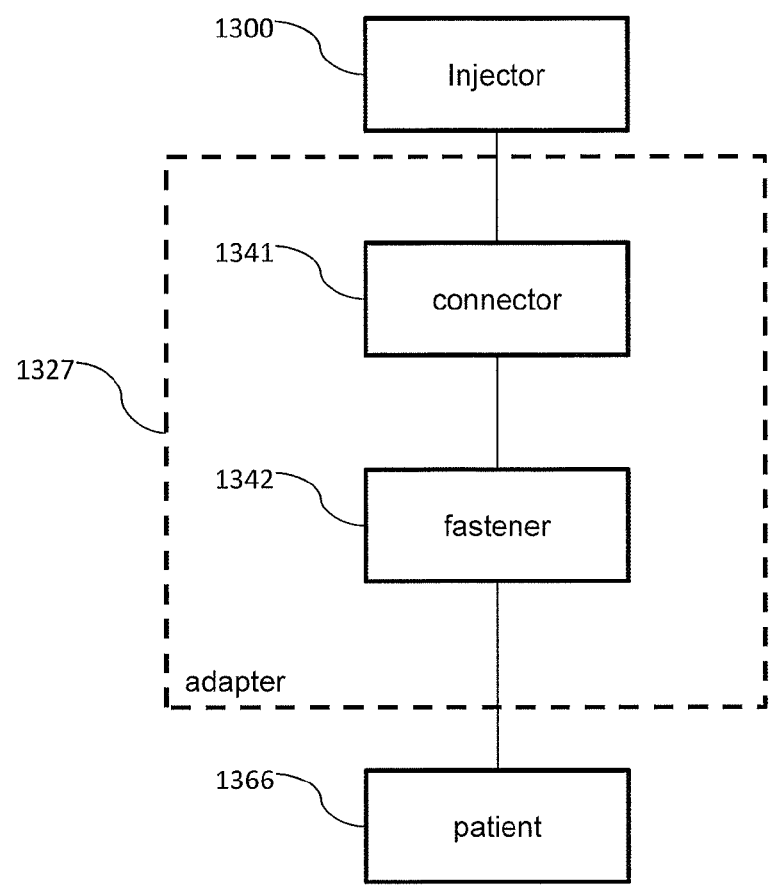
FIG. 13 is a block diagram of an autoinjector and a stabilizing adaptor in accordance with some embodiments of the current invention.

FIG. 13 is a block diagram of an autoinjector 1300 and adapter 1327 in accordance with an embodiment of the present invention. Optionally an adaptor 1327 may extend operation of injector 1300. For example, adaptor 1327 may stabilize injector 1300 on a patient allowing for longer injection times than for injector 1300 operating in an autonomous mode.

In some embodiments, adaptor 1327 may include a connector 1341 for attaching the adaptor to the injector and/or a fastener 1342 for fastening to a patient. For example, connector 1341 and fastener 1342 may be a single integrated part (for example molded out of a single piece of plastic). Alternatively or additionally, connector 1341 and fastener 1342 may be formed as two separate parts. Optionally, adapter 1327 including connector 1341 and fastener 1342 are first attached to injector 1300 and the complete assembly fastened to patient 1366 as a unit. Alternatively or additionally, adapter 1327 including connector 1341 and fastener 1342 may be fastened to the patient and injector 1300 stabilized as it is placed onto the patient. Alternatively or additionally, connector 1341 may be attached to the injector and fastener 1342 may be fastened to the patient and/or as injector 1300 is placed on the patient, connector 1341 is mated with fastener 1342 stabilizing the injector. In some embodiments there may be multiple fasteners 1342 and/or connectors 1341.

In some embodiments, connector 1341 may attach to an outer housing of injector 1300. For example, connector 1341 may be attached by a clamp and/or a friction fitting that grasps the walls of injector 1300. For example the injector 1300 may have a patient contact surface on a distal end thereof and connector 1341 may be attached to the side walls of the injector 1300. Alternatively, connector 1341 may attach to injector 1300 via an adhesive. In some embodiments, connector 1341 may be adjustable and/or adapted to attach any of a plurality to different injectors. In some embodiment, connector may be configured to attach to a specific injector. Alternatively or additionally other connection methods like magnetic force or Velcro are possible.

In some embodiments, connector 1341 may mate to fastener 1342 by a friction fitting. Alternatively or additionally connector 1341 may mate to fastener 1342 by a threaded fitting and/or a clamp and/or an interference element and/or a snap. The connection between fastener 1342 and connector 1341 may be reversible and/or may be permanent and/or irreversible (for example using a tooth and ratchet fitting). For example a ratchet and thread fittings may enable process of fixing and linkage. With a magnetic fitting linkage may occur alone. Adhesive, friction and/or Velcro® fittings may include passive actions that user should do properly. With thread, magnet, friction and/or Velcro it may be simple to disengage the device from the adaptor for example for re-use.

14 Adhesive and Ring for Stabilizing an Autoinjector

FIGS. 14A-F illustrate use of a drug delivery device, for example an injector 1400 and a stabilizing adapter 1427 in accordance with an embodiment of the current invention. In an exemplary embodiment, adapter 1427 includes an optional connector 1441 in the form of a ring. Optionally, the distal end of injector 1400 is inserted into a cavity 1411 of adaptor 1427. Optionally, connector 1441 is permanently fixed to a fastener 1442 including a base and an adhesive 1478 for adhering to skin in the vicinity of an injection site 1466 of a patient (for example see FIG. 14C). For example the adhesive may surround the injection site and/or may be in an area within 1 cm of the injection site and/or within 5 cm of the injection site. Connector 1441 is optionally configured to surround and/or limit movement of a distal surface of an outer housing 1440 of injector 1400.

In some embodiments, injector 1400 may be configured for operation in an autonomous mode and/or without adapter 1427 and/or without stabilization. For example, injector 1400 may include for example a pen injector and/or for example one of the many pen injectors known in the art. Control and/or operation protocols of the stabilized injector 1400 in the extended mode (for example with adaptor 1427) may be unchanged over operation in the autonomous mode.

FIG. 14 A is an exploded perspective view of injector 1400 and adapter 1427 in accordance with some embodiments of the current invention. In some embodiments, connector 1441 may limit lateral movement (in the x-y plane parallel to injection site 1466 of the patient) of the distal end of injector 1400. Additionally and/or alternatively, connector 1441 may limit rotational movement of injector 1400. For example, connector may closely surround injector 1400 along its length, preventing rotation around the x and/or y-axis. For example, connector 1441 may attach itself to the side walls of injector 1400 over a length ranging between 0.5 cm and 2.0 cm and/or 2.0 cm to 5.0 cm and/or longer. Optionally, friction between housing 1440 and connector 1441 may prevent rotation of injector 1400 around its main axis (the z-axis). Alternatively or additionally, connector 1441 may limit movement of injector 1400 perpendicular to the injection site of the patient. For example, friction between connector 1441 and housing 1440 may prevent movement of injector 1400 in the axial direction (along the z-axis).

In some embodiments, adaptor 1427 may be fastened to a patient before being attached to injector 1400. For example, a doctor may give a patient an injector 1400 including a medicine to be taken at a certain time after the patient is discharged from the hospital. A member of the hospital staff may fasten fastener 1442 and/or connector 1441 to the patient at a preferred injection location. When the time comes for the injection, the patient optionally inserts the distal end of injector 1400 into connector 1441 and activates injector 1400. Alternatively or additionally a member of the hospital staff may fasten fastener 1442 to the patient at a preferred injection location. When the time comes for the injection, the patient optionally mates connector 1441 to fastener 1442 and/or inserts the distal end of injector 1400 into connector 1441 and/or activates injector 1400. Alternatively or additionally, when the time comes for the injection, the patient may fasten fastener 1442 and connector 1441 to his injection site 1466 at a preferred injection location. The patient optionally then inserts the distal end of injector 1400 into connector 1441 and activates injector 1400. Optionally, connector 1441 may be configured to make it easy for a limited dexterity patient to position injector 1400. For example, the opening to connector 1441 may be beveled, for example the opening of connector 1441 may be beveled, for example like a funnel, to help direct the distal end of injector 1400 to the injection site.

In some embodiments, injector 1400 may be attached to connector 1441 before fastening to the patient. The patient optionally, fastens the entire assembly (injector 1400 and adapter 1427) together to the injection location and/or activates the injector.

In some embodiments cavity 1411 may be cylindrical. The cross section of cavity 1411 optionally has a shape to fit the cross section of the distal end (the end nearest to the patient) of the injector. For example, the cross section of the distal end of the injector and/or of cavity 1411 may be circular and/or elliptical and/or rectangular and/or may have rounded corners. Alternatively or additionally cavity 1411 may be conical and/or pyramidal, for example with a large opening. The large opening may make it easier to insert the injector. The surface of contact between injector 1400 and adaptor 1427 may include, for example, the surface of the inner walls of adapter 1427 which contact, for example, the outer surface of the distal end of injector 1427.

Figure 14A:
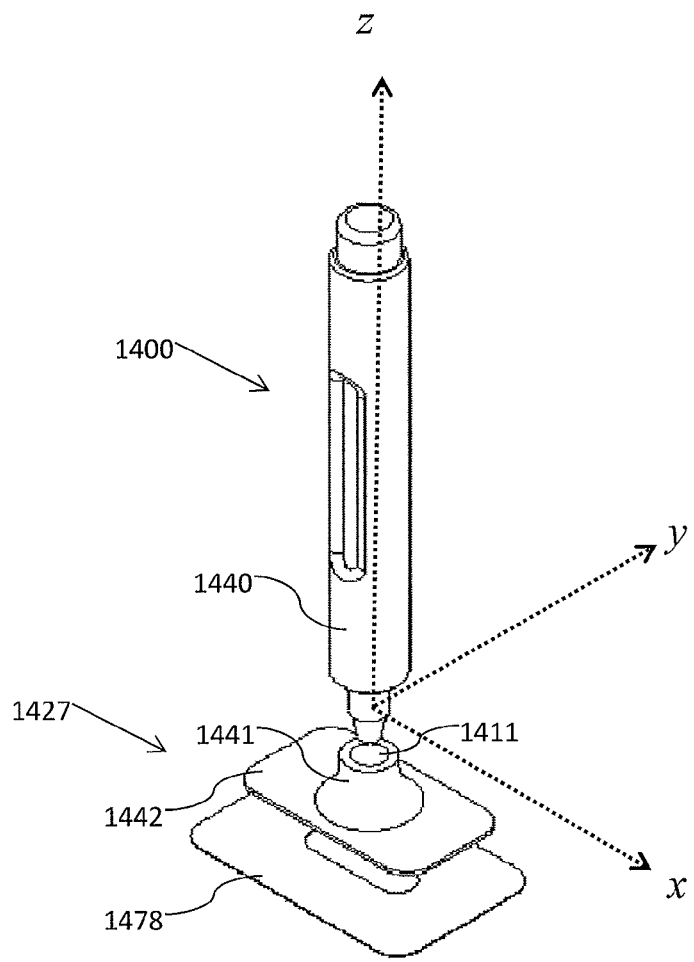
FIG. 14A-F is a perspective view and schematic cross sectional views of various states of an adhesive and ring stabilizing adaptor and autoinjector in accordance with some embodiments of the current invention.
Figure 14B:
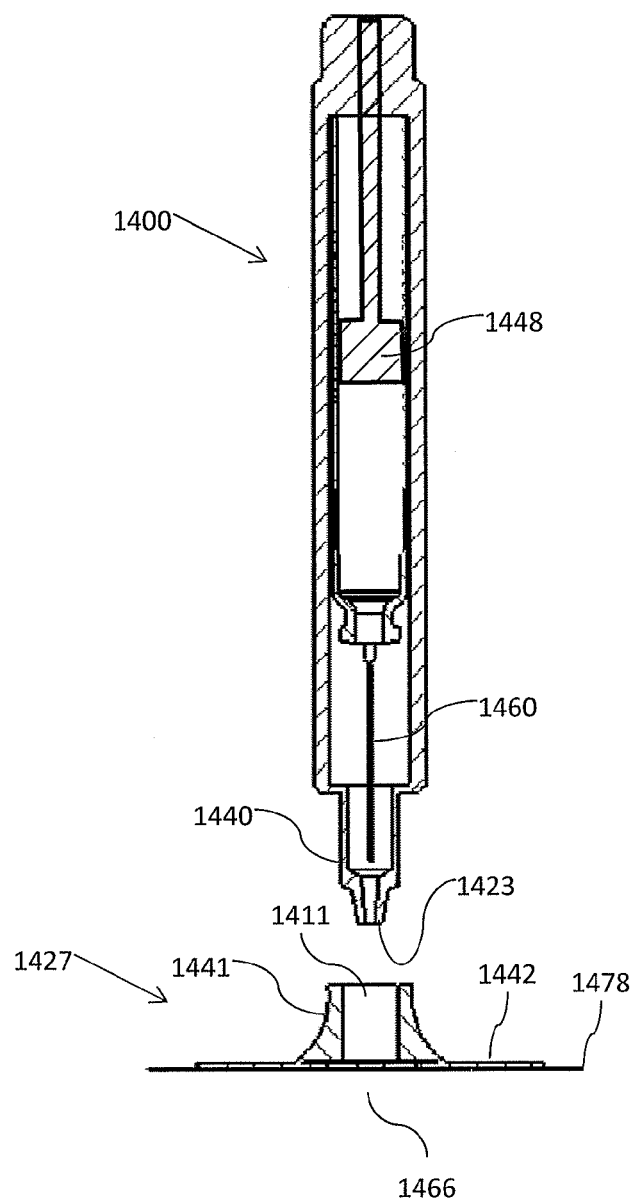

FIG. 14B is a crossectional view of injector 1400 and adapter 1427 prior to positioning on a patient and/or prior to injection in accordance with an embodiment of the current invention. A distal surface 1423 including a skin contact area is illustrated above an injection zone 1466 of the patient.

Figure 14C:
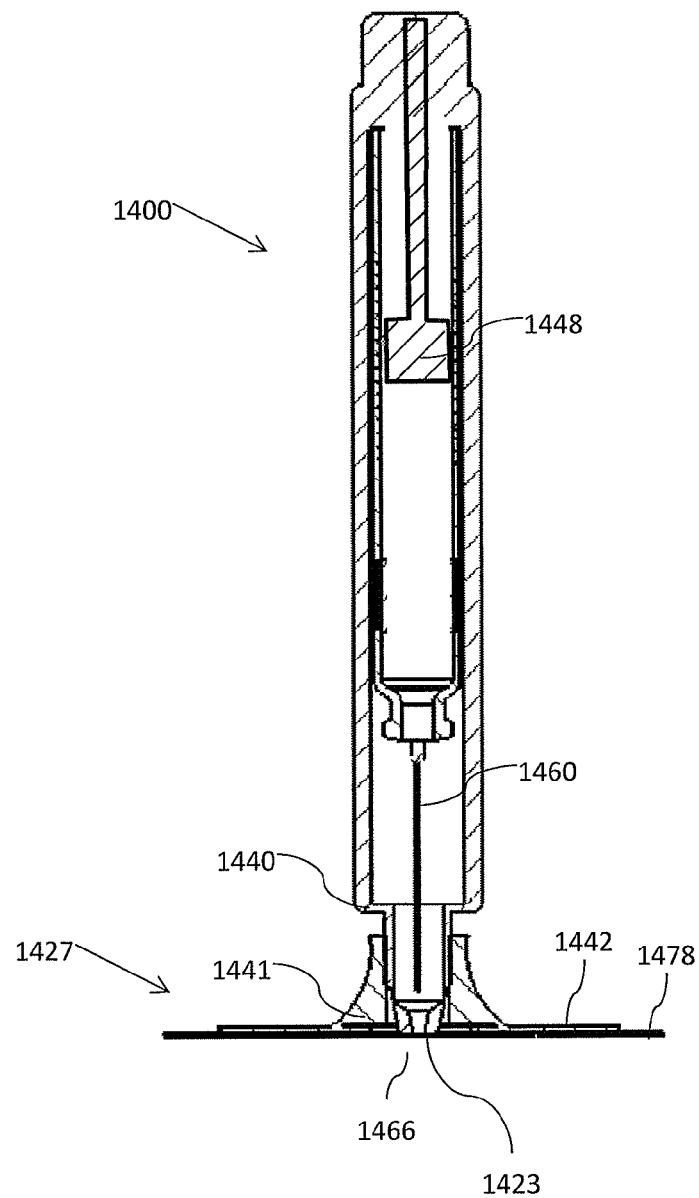

FIG. 14C is a crossectional view of injector 1400 and adapter 1427 positioned on a patient prior to injection in accordance with an embodiment of the current invention.

Optionally injector 1400 includes a needle 1460 and/or a plunger 1448. Optionally, injector 1400 includes a drive mechanism and/or a needle extension/retraction mechanism, for example, similar to embodiment 400 and/or injector 600 and/or 700 above. In some embodiments connector 1441 may attach to the side walls of injector 1400. For example connector 1441 may be attached to a length of the side walls of the injector.

Figure 14D:
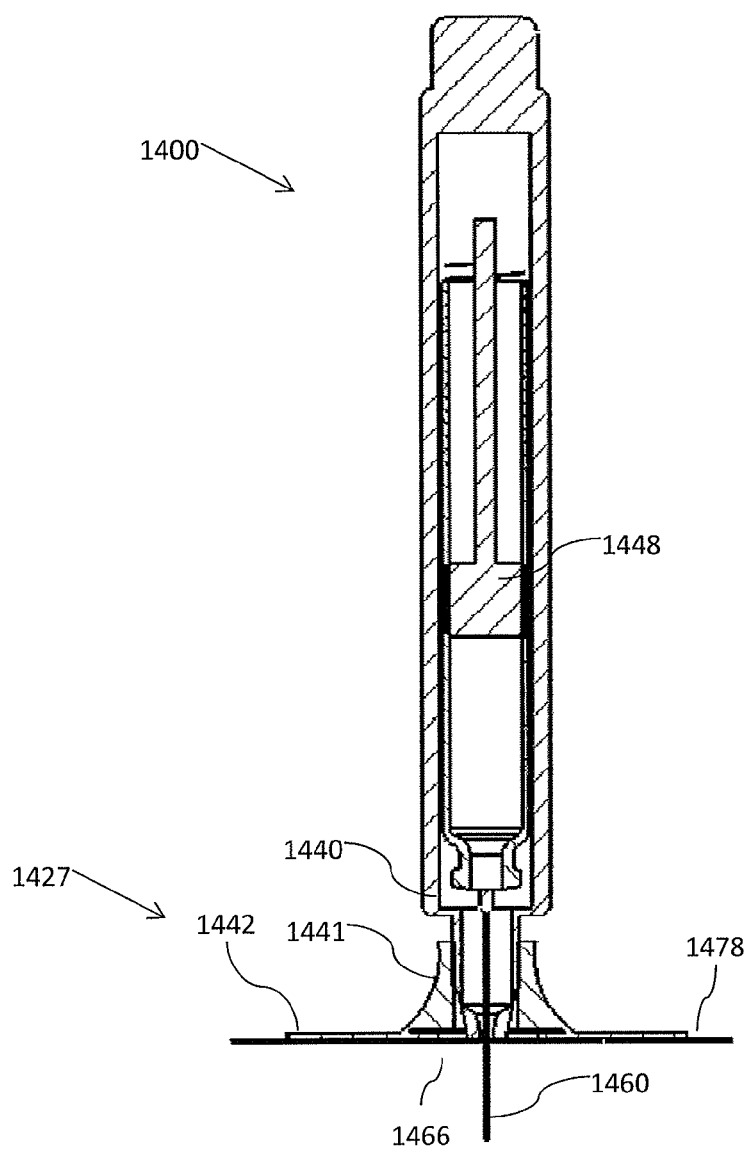

FIG. 14D is a crossectional view of injector 1400 and adapter 1427 positioned on a patient after activation and/or extension of needle 1460 into injection site 1466 and/or during injection as plunger moves downward discharging medicine into the patient in accordance with an embodiment of the current invention.

Figure 14E:
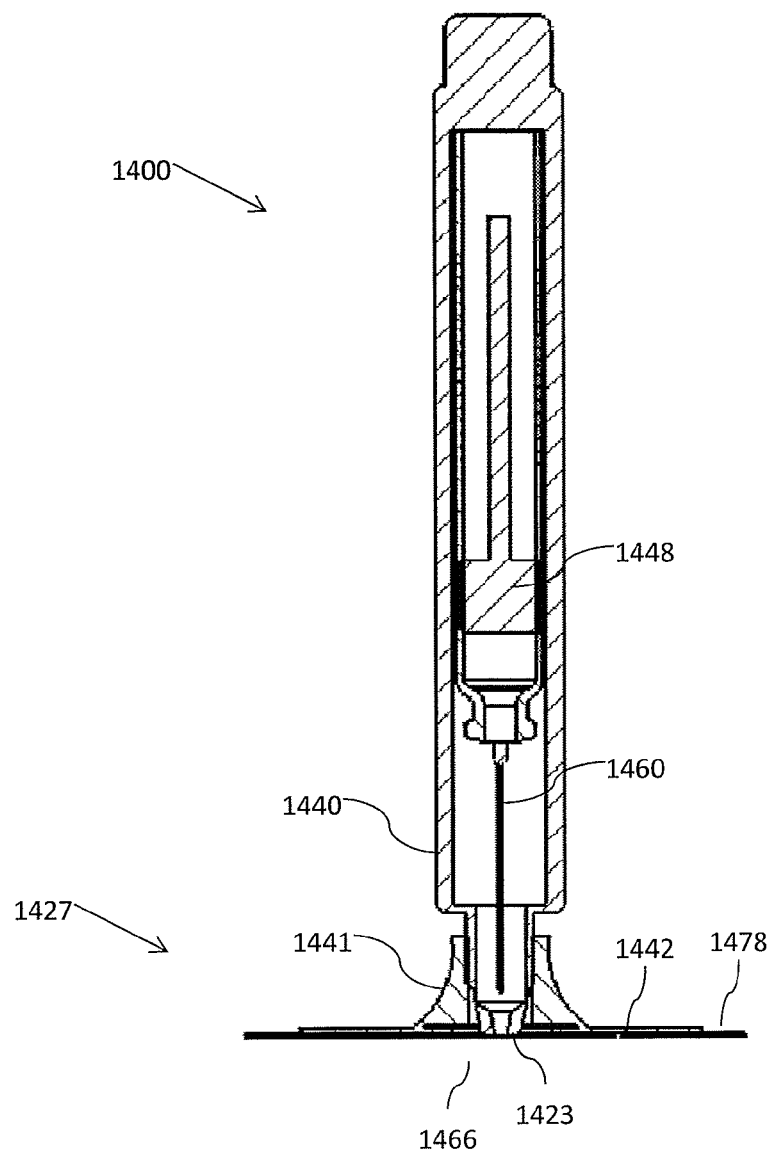

FIG. 14E is a crossectional view of injector 1400 and adapter 1427 positioned on a patient after injection in accordance with an embodiment of the current invention. Optionally, after injection, plunger 1448 has reached the end of its movement, discharging a full dose of the medicine and/or needle 1460 has retracted.

Figure 14F:
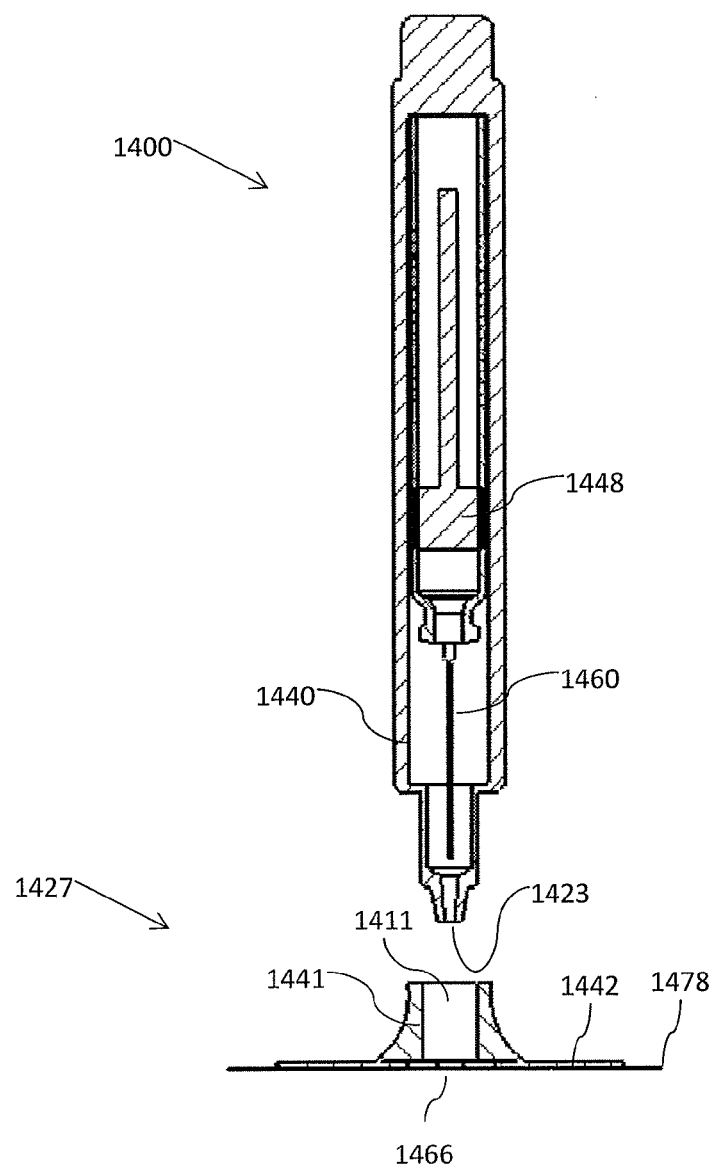

FIG. 14F illustrates removal of an injector from a stabilizing adapter and/or patient in accordance with an embodiment of the current invention. In the embodiment of FIG. 14F, injector 1400 is optionally removed from injection site 1466 while adapter 1427 optionally remains on injection site 1466. For example, adapter 1427 may be used to stabilize an injector in a subsequent injection. Alternatively or additionally adapter 1427 may be removed from injection site 1466 after removal of injector 1400. Optionally, injector 1400 and/or adaptor 1427 are disposed of and/or reused and/or recycled separately and/or together. Alternatively or additionally, injector 1400 and/or connector 1441 and/or fastener 1442 may be removed from injection site 1466 together. For example, injector 1400 may be rotated to pivot off fastener 1442, for example in a manner similar to that illustrated in FIG. 6D. For example, using injector 1400 to pivot off fastener 1442 may be easier for patients with limited small motor skills that trying to pull and/or pivot and/or peel off fastener 1442 on its own.

15 Friction Fitting for Stabilizing an Autoinjector

Figure 15:
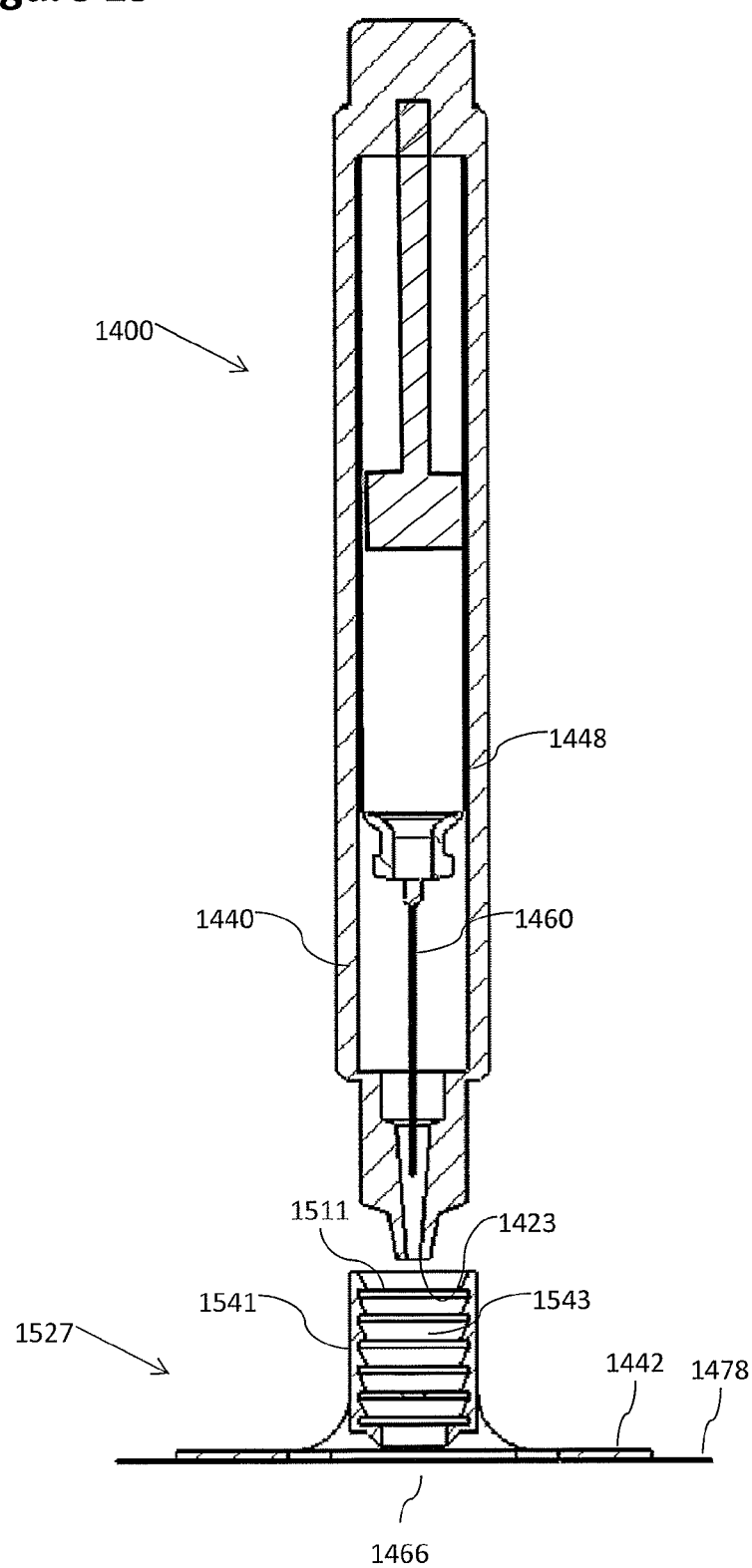
FIG. 15 is a schematic cross sectional illustration of a friction fitting for stabilizing an autoinjector in accordance with some embodiments of the current invention.

FIG. 15 is a cross sectional illustration of injector 1400 and a stabilizing adapter 1527 including a friction fitting 1543 prior to positioning on a patient and/or prior to injection in accordance with an embodiment of the current invention. For example friction fitting 1543 may include a friction coating on the surface of contact between adapter 1527 and injector 1400. For example friction fitting 1543 may be on the inner surface of a cavity 1511 in a connector 1541. For example the fitting may include slanted teeth that increase the friction in one direction. For example it may require less force to insert injector 1400 into adapter 1527 then to remove injector 1400 from adapter 1527. Operation of adapter 1527 may for example be as described with respect to adapter 1427.

16 Adjustable Angled Stabilizing Adaptor

Figure 16:
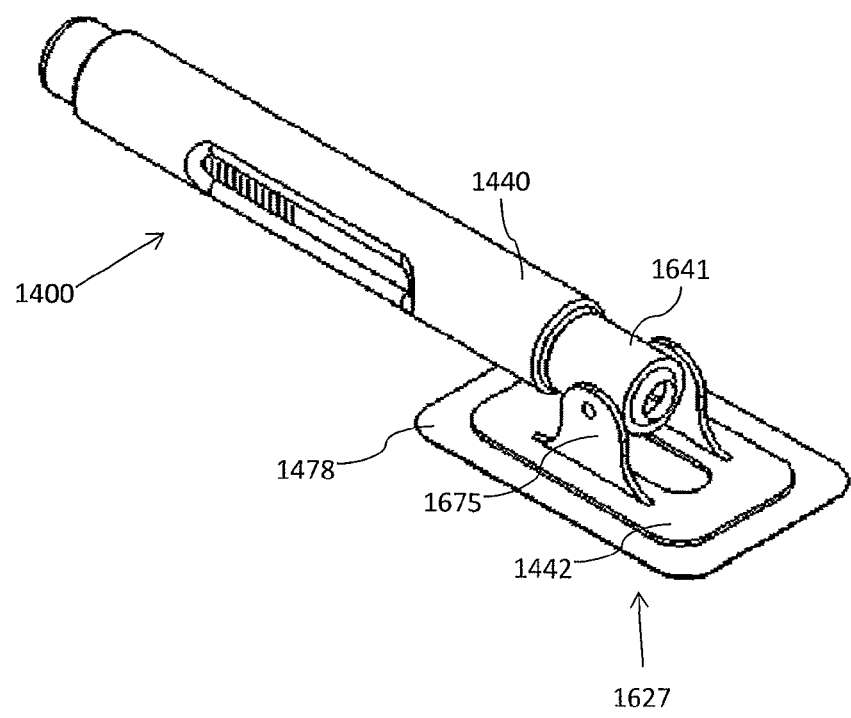
FIG. 16 is a perspective view of an adjustable angled stabilizing adaptor in accordance with some embodiments of the current invention.

FIG. 16 is a perspective view of injector 1400 and a stabilizing adapter 1627 having an adjustable angle between injection site and the injector in accordance with some embodiments of the current invention. For example the angle during operation of the injector between the skin surface at the injection site and the principle axis of the injector, the principle axis of the drug reservoir and/or the principle axis of the needle may be adjusted between 80 to 100 degrees and/or between 60 and 120 degrees and/or between 30 and 150 degrees.

In some embodiments, the connection between injector 1400 and/or adaptor 1627 and/or fastener 1442 may include a pivot 1675 and/or an axle (for example as illustrated on connector 1641). Optionally a lock may fix the angle of injection. For example a lock may include a ratchet and teeth and/or a clamp.

In some embodiments an angle of the injection may be set prior to distribution of the injector and/or adaptor to a patient. For example, the angle may be set by a staff member at a hospital and/or clinic and/or by a pharmacist. Alternatively or additionally, the angle of the injection may be set by the patient and/or a medical aid.

17 Stabilizing Adapter with Strap Fastener

Figure 17:
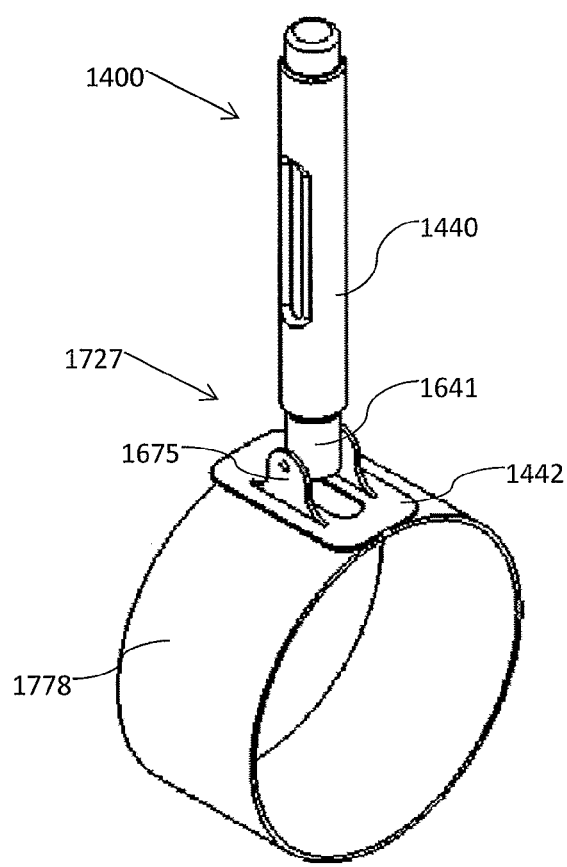
FIG. 17 is a perspective view of a stabilizing adaptor and autoinjector with a strap fastener in accordance with some embodiments of the current invention.

FIG. 17 is a perspective view of injector 1400 and a stabilizing adapter 1727 having a strap 1778 for fastening to a patient in accordance with some embodiments of the current invention.

18 Stabilizing Adaptor with a Separate Coupling

Figure 18:
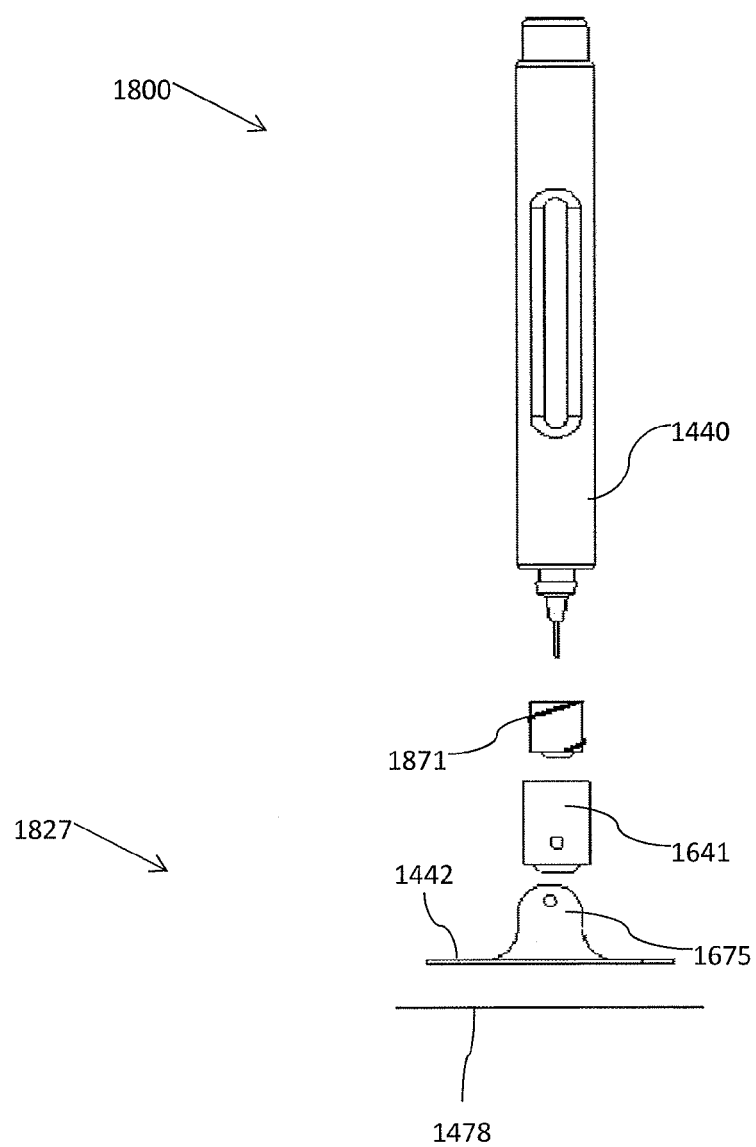
FIG. 18 is an illustration of a stabilizing adaptor with threaded connector in accordance with some embodiments of the current invention.

FIG. 18 illustrates an exploded view of an autoinjector drug delivery device and a stabilizing adaptor 1827 having a separate coupler in accordance with an embodiment of the current invention. A separate coupler may be used to connect different models of autoinjectors to one model adaptor. For example, one model coupler 1871 may attach to injector 1800 and mate to connector 1641 and/or fastener 1442. An alternative coupler may connect an alternative model injector to connector 1641 and/or fastener 1442. Optionally, coupler 1871 mates with connector 1641 by means of a threaded connection. For example, connector 1641 may be reversibly mated to coupler 1871 and/or injector 1400. Alternatively or additionally, connector 1641 may mate to coupler 1871 with another connection, for example an irreversible connection and/or a friction contact and/or a tooth, and/or an interference element and/or an adhesive.

19 Stabilizing Adapter with Injector Clamp

FIGS. 19A,B illustrate a stabilizing adaptor for an injector in accordance with an embodiment of the present invention. Optionally, adaptor 1927 includes a coupler 1971 having a clamp 1969 that clamps to the side walls of an injector. For example, clamp 1969 may be adjustable to hold onto injector 1400 and/or a different model injector. For example, claim may hold onto injector 1400 at a distance ranging between 1 to 10 cm from the distal end of the injector (and/or the skin contact area on the distal end of the injector). Optionally coupler 1971 may be fastened to the patient along with connector 1441 and/or fastener 1442. Once adapter 1927 is fastened to a patient, injector 1400 may for example be clamped into place and activated. In some embodiments, fastener 1442 may be fastened to the patent at a distance from injection zone 1466. For example fastener 1442 may be fastened to the patent at a distance ranging from 0.1 to 3.0 cm on one side of injection zone 1466. Alternatively or additionally, injector 1400 may be help to coupler 1971 by another kind of fitting (for example a friction fitting and/or a threaded fitting etc.)

20 Stabilizing Adapter with Separate Coupler

FIGS. 20A,B illustrate a stabilizing adapter with a mating coupler in accordance with some embodiments of the present invention. Coupler 2071 of may for example be separated from connector 1441 and/or fastener 1442. For example, injector 1400 may be attached to coupler 2071 while coupler 2071 is disconnected from connector 1441. Fastener 1442 is optionally attached independently to the patient in the vicinity of injection site 1466. For example, in the embodiment of FIGS. 20A,B fastener 1442 may be fastened to the patient by a medical staff member while the patient is in a clinic and/or by the patient and/or a medical aid before injection. Coupler 2071 may optionally be mated to connector while injector 1400 is attached to coupler 2071.

21. Adaptor with Multiple Fasteners and/or Couplers

Figure 21:
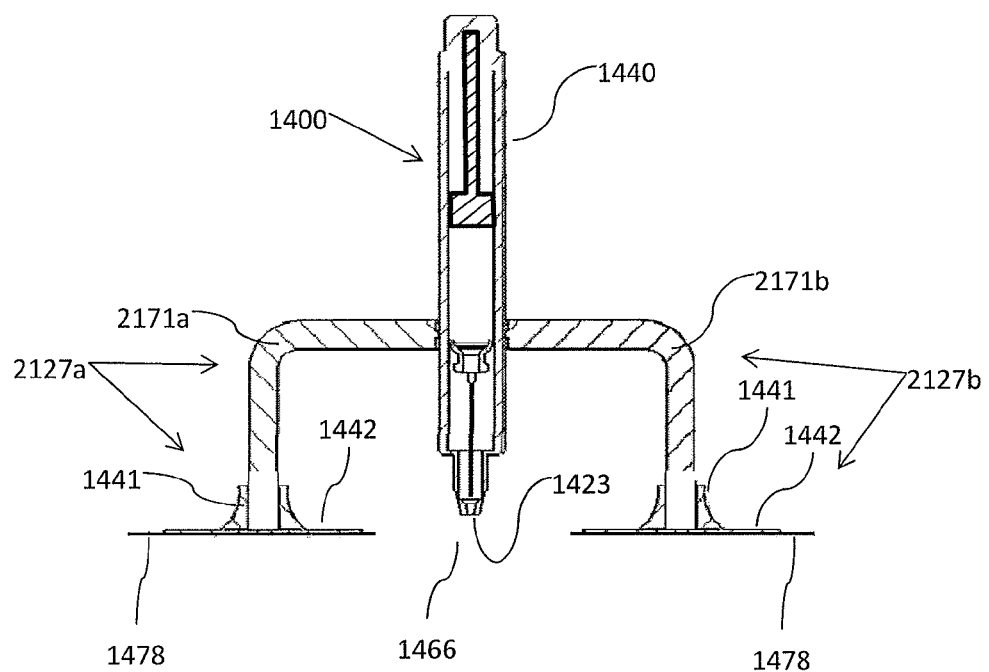
FIG. 21 is a schematic cross sectional of a multipronged adapter and autoinjector in accordance with an embodiment of the current invention.

FIG. 21 illustrates a multipart adapter for stabilizing an autoinjector in accordance with an embodiment of the current invention. For example, multiple adaptors 2127a,b may be distributed in an area around injection site 1466. Each adaptor 2127a,b may stabilize injector 1400 from one or another side. Skin between adaptors 2127a and 2127b, may be stretched, for example making it easier to locate injection zone 1466 for a patient having flabby skin. In some embodiments multiple adaptors 2127a,b may first be attached to the patient and then injector 1400 may be attached to adapters 2127a,b (for example as in the embodiment of FIG. 19 for a single coupler). Alternatively or additionally, first injector may be attached to couplers 2171a,b and then couplers 2171a,b may be mated to couplers 1441, for example similar to the embodiment of FIG. 20 for a single coupler.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In some embodiments, the adhesive may include a semi stiff skirt. The skirt may make the injector more stable. Alternatively or additionally, the adhesive may be connected to a stiff base (for example the base of the injector) without a semi-stiff skirt. For example, an embodiment without a semi stiff skirt may be easier to remove after the end of injection.

22 Method of Manufacture of an Compound Device

Figure 22:
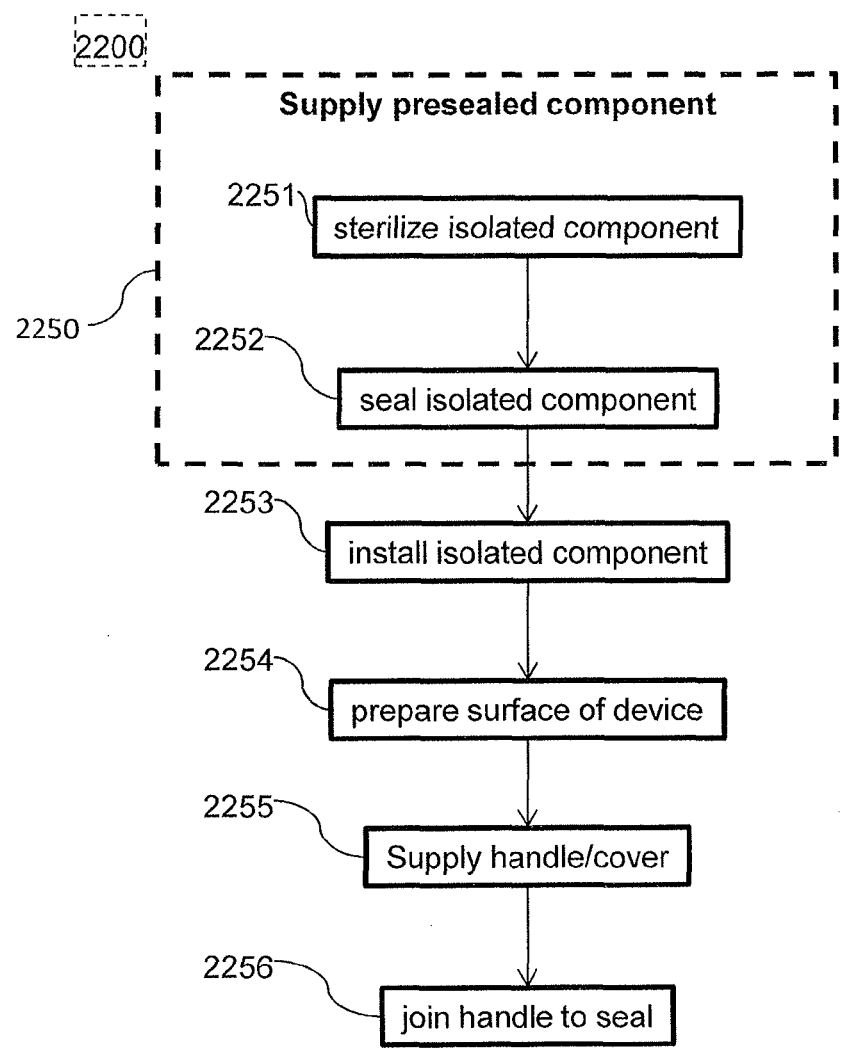
FIG. 22 is a flowchart illustrating a method of manufacture of a compound device in accordance with an embodiment of the present invention.

FIG. 22 is a flow chart illustration of a method of manufacture of a compound device in accordance with an embodiment of the present invention. In some embodiments, a protected component may be installed into a device in a sealed state. The device may optionally include an active surface and/or a handle and/or a surface cover and/or an activation mechanism. Optionally, the handle and/or the surface cover and/or the activation mechanism may be joined to a seal of the protected component, for example by a coupler. Optionally, the coupler may synchronize unsealing of the protected component and activation of the active surface. For example the method of manufacture illustrated in embodiment 2200 of FIG. 22 may optionally be used in manufacturing one, some and/or any of the embodiments of an injector illustrated in the embodiments illustrated herein above and/or below. In some embodiments, a sterile adhesive may be sealed and/or covered by a protective packaging for example a cover. The adhesive may for example be attached to a surface in a sterile and/or protected state. Optionally the coupler may be connected to the protective packaging and/or cover of the adhesive and/or may synchronize opening of the packaging with another act.

In some embodiments an isolated component may be supplied 2250 in a presealed state. For example, the presealed component may include a fluid path of a preloaded syringe. Optionally the syringe and/or fluid path may be sterilized 2251 and/or preloaded with for example medicine and/or sealed 2252 in an aseptic room.

In some embodiments, a protected component may be installed 2253 into a device in a sealed state. For example, in some embodiments, a preloaded syringe with a sealed sterile fluid path may optionally be installed 2253 into an autoinjector.

In some embodiments, the device may optionally include an active surface with an activation mechanism. The active surface may be prepared 2254. For example an autoinjector may include an active surface including an adhesive for attaching to a patient. Preparing 2254 the surface may include for example applying the adhesive to the surface.

In some embodiments, the active surface may be supplied 2255 with an activation mechanism and/or protective cover. For example, in some embodiments, an adhesive surface may be covered by an adhesive cover and/or enabled by removing the adhesive cover.

In some embodiments, the surface cover and/or activation mechanism and/or handle may be joined 2256 to the seal of the protected component, for example by a coupler. Optionally, the coupler may synchronize unsealing of the protected component and activation of the active surface. For example removing the surface cover and/or activating the surface may trigger unsealing of the protected component. Alternatively or additionally, unsealing of the protected component may trigger removal of the surface cover and/or activating of the active surface.

23 Safety Cover

FIGS. 23A-D illustrate a system 2300 designed to remove a needle cover 2391 in accordance with an embodiment of the current invention. In some embodiments a needle may be installed into an autoinjector while covered with a needle cover. A safety cover may be installed to the injector and/or attached to the needle cover. Removal of the safety cover may also bring about removal of the needle cover.

Figure 23A:
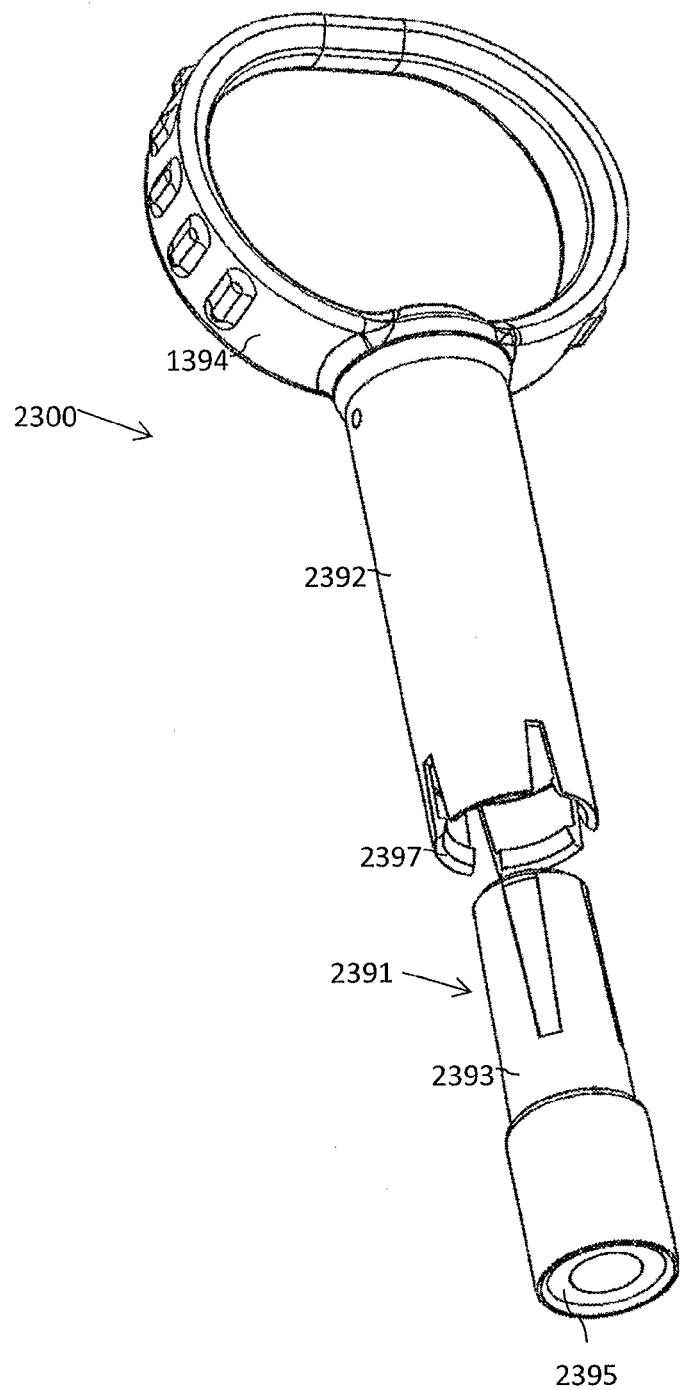
FIGS. 23A-D illustrate a needle cover and an injector safety cover including a needle cover remover in accordance with an embodiment of the present invention.
Figure 23B:
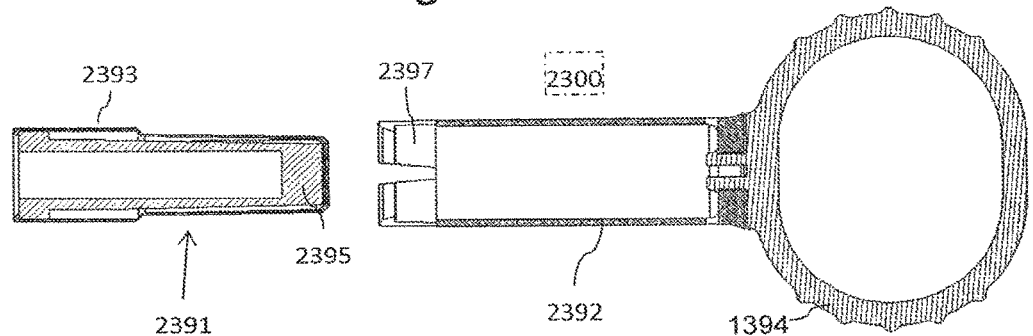
Figure 23C:
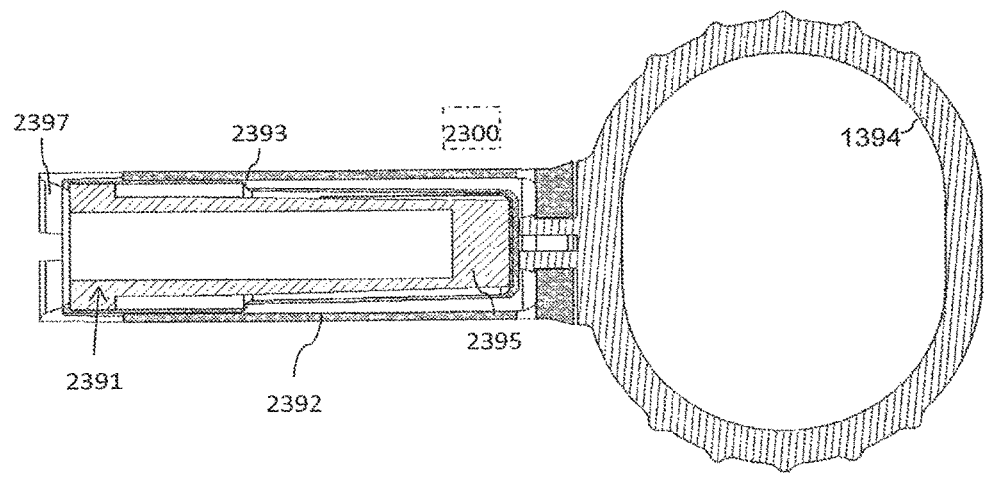

FIG. 23A is a perspective view of system 2300 and associated needle cover 2391. Optionally, needle cover 2391 includes a rigid outer shell 2393 and a sterile rubber core 2395. When needle cover 2391 is installed over a sterilized needle, rubber core 2395 may protect the sterility of the needle and/or shell 2393 may protect the needle from causing a stick hazard. Alternatively or additionally, a needle may be covered with a single cover (for example either rubber or rigid) that may preserve sterility and/or prevent a stick hazard.

For example, a prefilled syringe may be installed into an autoinjector (for example injector 1400) with a needle already covered with needle cover 2391. Before shipping the injector, system 2300 may be installed onto the injector. A needle cover remover, for example a needle protector 2392 is optionally pushed over shell 2393 of the needle cover. Needle protector 2392 may optionally have the form of a sleeve and/or a clamp that is inserted through an aperture in base 1442. Optionally, needle protector 2392 is inserted into the injector housing and/or is attached to needle cover 2391 after assembly of the injector. Protector 2392 may include clasps (for example clasps 2397) which engage shell 2393. When protector 2392 is removed from the injector, clasps 2397 may pull off needle cover 2391.

Figure 23D:
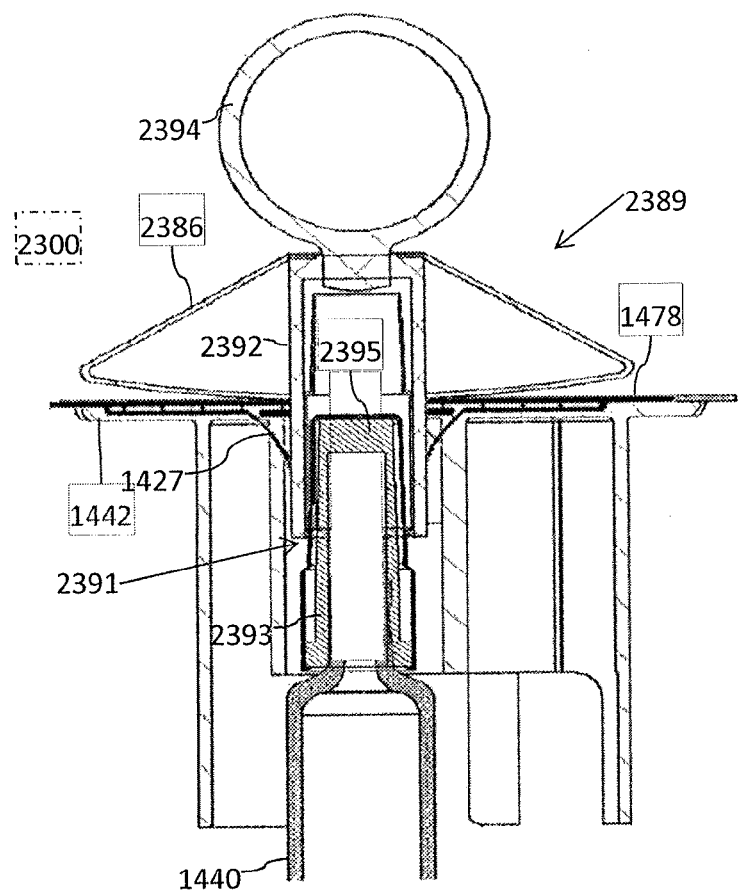

FIG. 23D illustrate installation of needle protector 2392 and adhesive cover for example adhesive protector 2389 in accordance with exemplary system 2300 of the present invention. The safety cover may include for example a handle 2394 and/or a needle protector 2392 and/or an adhesive protector 2389 for covering an adhesive 1478. For example, handle 2394 may be attached to extenders 2386 for attaching to adhesive protector 2389 and/or for peeling adhesive protector 2389 from adhesive 1478 when handle 2394 and/or a needle protector 2392 and/or the needle cover (for example shell 2393 and or rubber core 2395) are pulled off.

In some embodiments, a stabilizer (for example adaptor 1427) may be attached to an autoinjector pen (for example Rita pen injector planned for production by Unilife corporation 150 South Warner Road, King of Prussia, Pa. 19406 USA and/or Metoject/Metex pen injector available from Medac GmbH Scion House Stirling University Innovation Park Stirling FK9 4NF England). Optionally, protector 2392 and/or handle 2394 are installed through the open front end of the injector (for example in place of the front cap of the injector). The injector can then be used in a supported and/or stabilized mode without no and/or minimal changes in the manufacture and/or operation of the device. For example, the user pulls off handle 2394 and/or protector 2392. Optionally, protector 2392 pulls off sterile needle cover 2391 that may for example have been mounted on the syringe during preloading of medicine in a clean room. The injector and/or stabilizer is optionally then placed on the skin and/or used exactly as the unstabilized original injector.

24 Modular Drug Delivery Device

FIGS. 24A-G illustrate a modular preloaded stabilized drug delivery device, for example an autoinjector 2400 in accordance with an embodiment of the current invention. Optionally, a drug distributor may load injector 2400 with a drug using standard components and procedures. Optionally, injector 2400 may be loaded with a standard form syringe and/or assembled by simple assembly not requiring special tools, skilled workers and/or long assembly time. For example, the drug delivery device may be delivered to a medicine distributor with a small number of separate assemblies. For example, the drug delivery device may be delivered to the medicine distributor with two separate preassembled assemblies, a distal assembly 2498 and a proximal assembly 2499. The medicine distributor may optionally supply the medicine in a standard sealed preloaded syringe with a needle cover protecting the sterility of a needle at the distal end and/or a stopper sealing the syringe barrel at the proximal end. Finally assembly of the drug delivery device optionally includes inserting the syringe into a channel in distal assembly 2498 and then assembling the drug delivery device for example by placing proximal assembly 2499 over the proximal end of distal assembly 2498 and/or snapping the assemblies together.

Figure 24A:
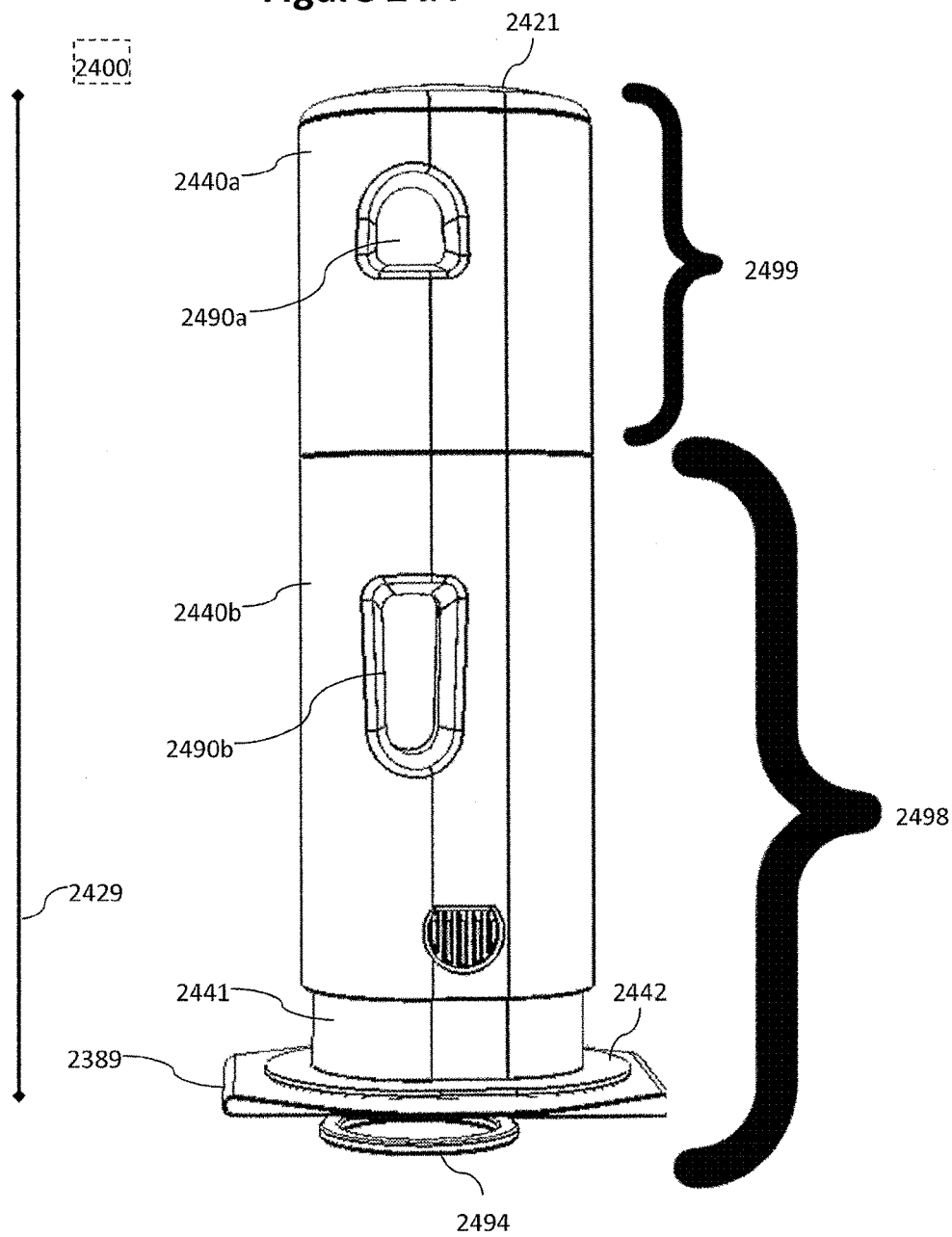
FIGS. 24A-G illustrate a modular stabilized injector in accordance with an embodiment of the present invention.

FIG. 24A illustrates an exterior view of exemplary injector 2400 in accordance with an embodiment of the current invention. Optionally proximal assembly 2499 is packed into a proximal housing 2440a and/or distal assembly 2498 is packed into a distal housing 2440b. Optionally, a needle shield 2441 is slidably attached to the distal end of distal housing 2440b. Needle shield 2441 optionally includes a skin contact surface, for example an adhesive base 2442. The adhesive of base 2442 may be protected for example by a adhesive protector 2389. An optional pull tab handle 2494. Handle 2494 serves for example for enabling injector 2400 and/or for peeling adhesive protector 2389 and/or for removing a needle cover. A proximal cover 2421 optionally closes the proximal end of proximal housing 2440a. Windows 2490a and/or 2490b are optionally supplied for monitoring needle retraction and/or medicine discharge respectively. The height 2429 of injector 2400 may range between half the length of the long axis of base 2442 to the length of long axis 2442 and/or between the length of the long axis of base 2442 to twice the length of long axis 2442 and/or greater than twice the length of the long axis of base 2442. The large height of the injector may give leverage for pivoting base 2442 off a skin of a patient. An adhesive strength of said base may be adjusted to pivot off a skin of the patient without ripping the skin, for example when the injector is pivoted around an edge of base 2442. Optionally, the adhesive strength may be non-uniform. For example adhesive strength may be less far from a pivoting axis and more near the pivoting axis.

Figure 24B:
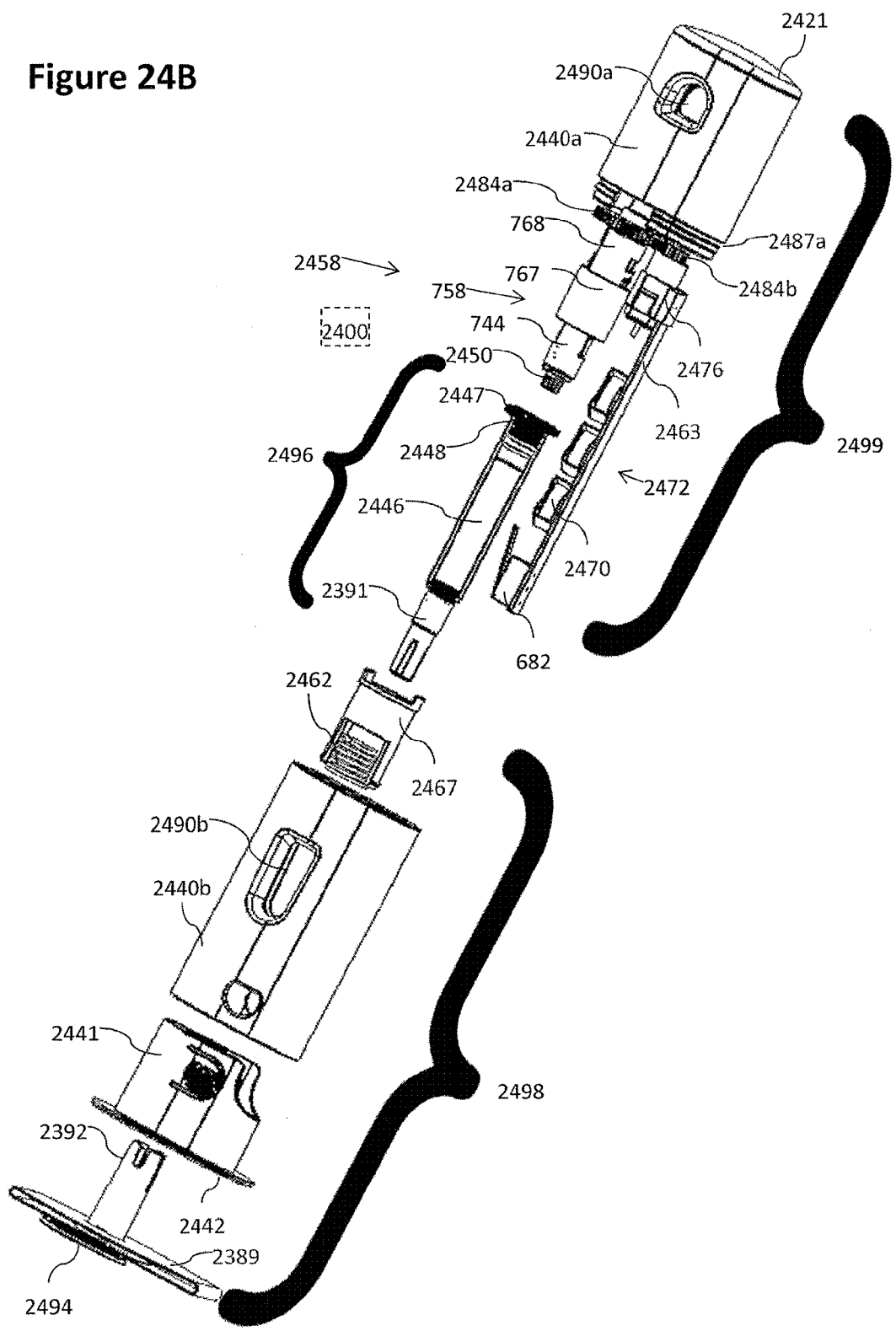

FIG. 24B is an exploded view of the system of injector 2400 in accordance with and embodiment of the current invention. Injector 2400 may for example include three modular assemblies: lower distal assembly 2498, upper proximal assembly 2499 and/or a preloaded syringe 2496.

In some embodiments, proximal assembly 2499 may include a drive system. For example, proximal assembly 2499 includes a power module 2472, a transmission 2458 including a rotary screw driver for a plunger and/or a retraction mechanism (for example as illustrated in FIGS. 7A-B and 7I-K).

In some embodiments, distal assembly 2498 may include a patient interface and/or a syringe fitting.

In some embodiments, transmission 2458 of proximal assembly 2499 optionally includes a needle retraction mechanism 758 and/or a telescoping assembly including a plunger adaptor 2450 for driving a plunger 2448 for discharging a drug and or a coupling element 2484a (for example a gear) for connecting to a motor (for example motor 2476).

In some embodiments, power module 2472 may include a modular component. For example the entire power module 2472 may be installed as a whole into injector 2400. For example power module 2472 may be tested as a unit (for example testing a motor 2476 and/or a battery 2470). Optionally the power module 2472 may be supported by a base for example a PCB board 2463. For example the power module 2472 may include a syringe position sensor, for example a switch 682 and/or a power source for example one or more batteries 2470 and/or a motor 2476. For example, power module 2472 may include a coupling element 2484b. For example coupling element 2484b may transfer power from power module 2472 to coupling element 2484a and/or transmission 2458. For example, coupling element 2484b may include a gear.

In some embodiments, the patient interface of distal assembly 2498 includes an adhesive base 2442 for stabilizing the drug delivery device on the skin of the patient and/or handle 2494 and/or needle shield 2441. For example, handle 2494 may be used for enabling the drug delivery device and/or for removing a needle protector 2392 and/or for removing a needle cover 2391 and/or for peeling off an adhesive protector 2389. For example, once injector 2400 is enabled, needle shield 2441 may collapse when pressed against the skin of the patient thereby activating injector 2400 and/or exposing a needle.

Figure 24C:
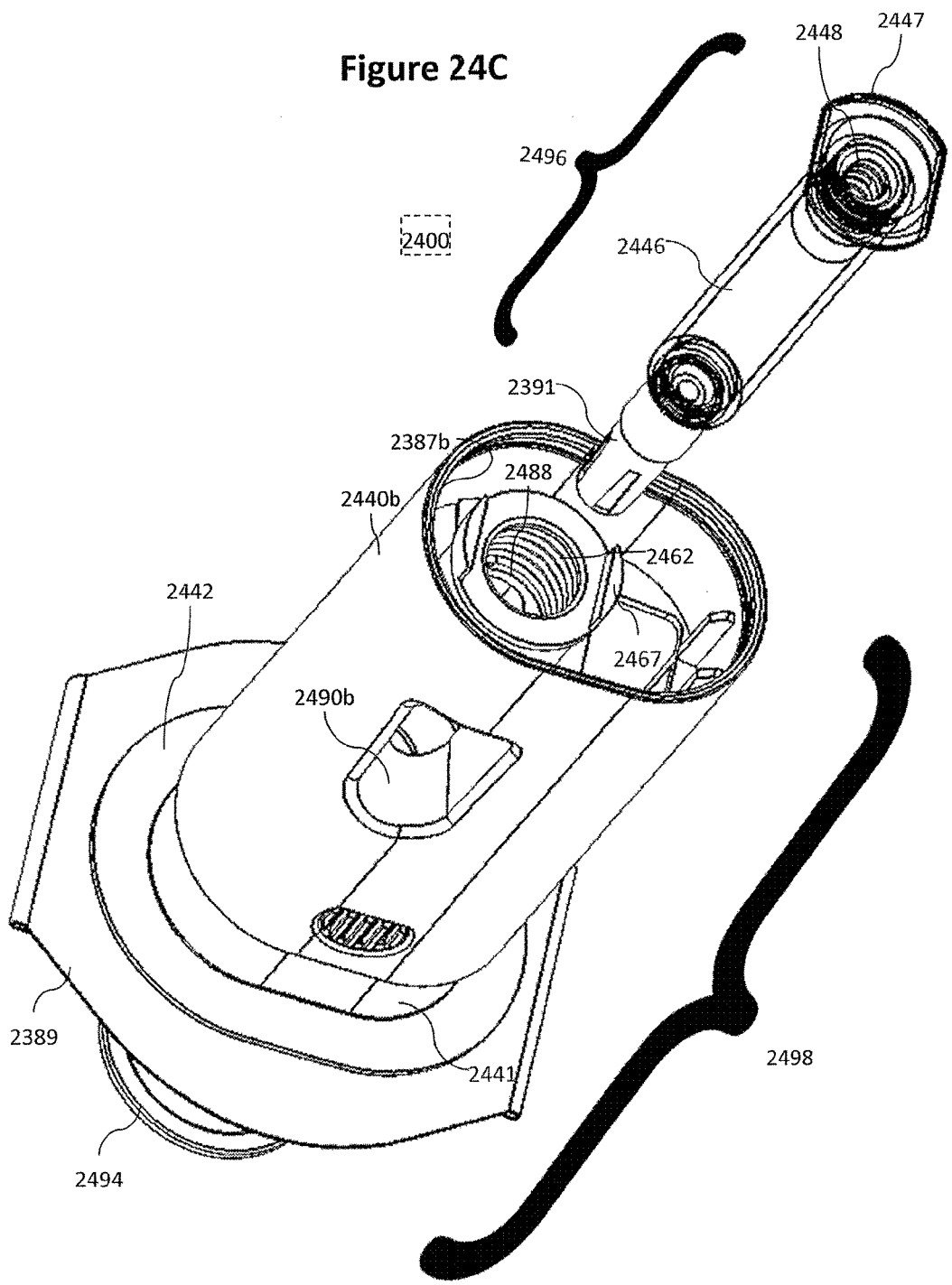

In some embodiments, the syringe fitting of distal assembly 2498 may include a channel 2488 fitting the syringe (for example as illustrated in FIG. 24C) and/or a syringe retainer 2467 and/or a biasing element (for example a return spring 2462) for retracting the needle.

In some embodiments, preloaded syringe 2496 may include a barrel 2446 filled with a aseptic and/or sterile drug. Barrel 2446 is optionally in fluid communication and/or rigidly attached to a hollow needle on the distal end of barrel 2446. Some and/or all of the needle may be covered and/or protected and/or kept sterile by needle cover 2391. An open proximal end of barrel 2446 is optionally sealed by a plunger 2448.

Figure 24D:
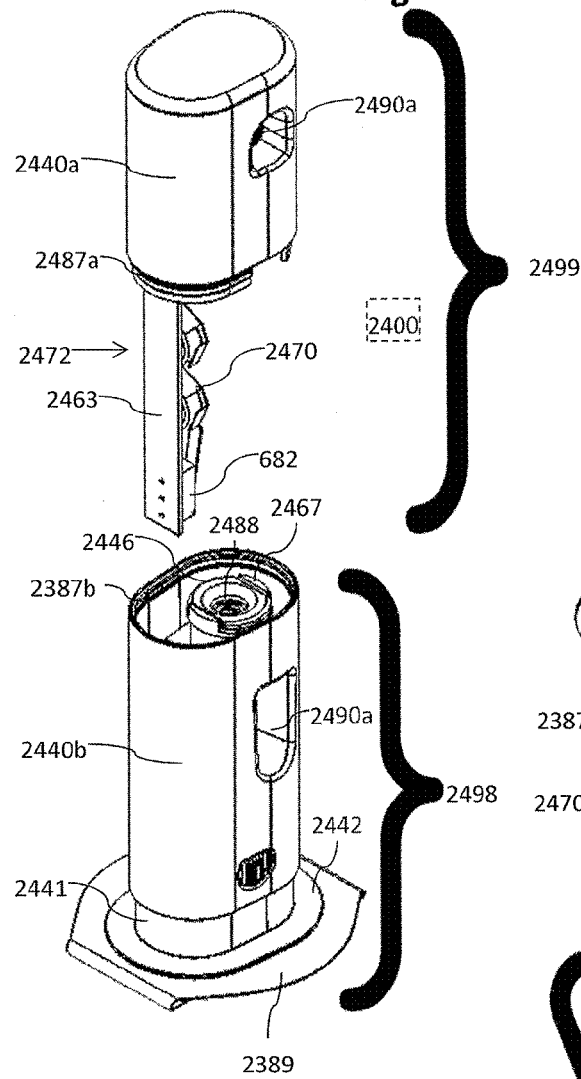
Figure 24E:
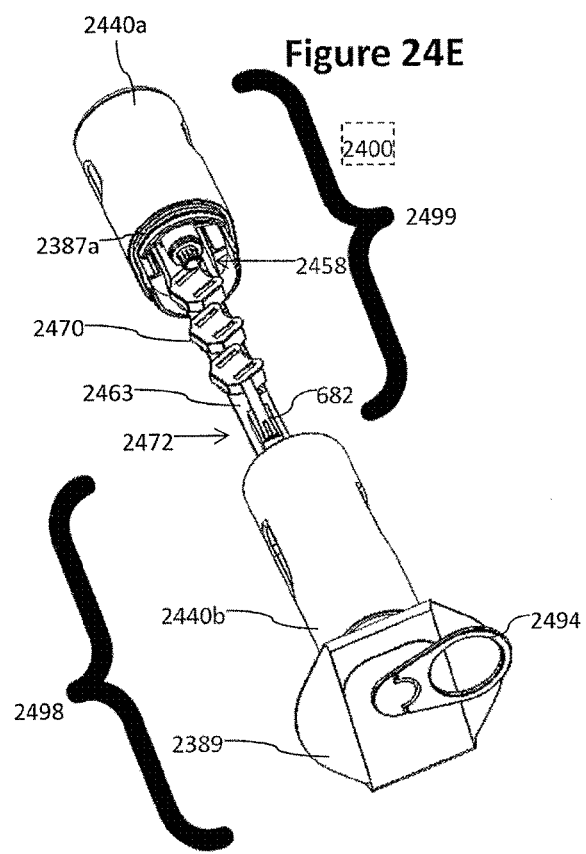

FIGS. 24C-E illustrate final assembly of a modular stabilized drug delivery device in accordance with an embodiment of the current invention. Optionally, proximal assembly 2499 and distal assembly 2498 are each supplied to a drug distributor, in an assembled state. For example, as illustrated in FIG. 24C, a drug distributor (for example a drug company and/or a hospital and/or a pharmacist inserts a preloaded syringe 2496 into channel 2488 in distal assembly 2498. When syringe 2496 is inserted into channel 2488 optionally needle cover 2391 is snapped into needle protector 2392 and/or a flange 2447 on syringe 2496 fits into and/or is snapped into retainer 2467.

In some embodiments, after inserting syringe 2496 into distal assembly 2498, the distributor then joins distal assembly 2498 to proximal assembly 2499 for example as illustrated in FIGS. 24D and/or 24E. For example the distributor joins distal assembly 2498 to proximal assembly 2499 in an axial motion. For example switch 682 slides into position inside of distal assembly 2498 and/or adaptor 2450 is joined to plunger 2448 and/or a snap fitting 2487a on proximal housing 2440a connects to a snap fitting 2487b on distal housing 2440b for example as illustrated in FIG. 24A.

In some embodiments, the assembled injector 2400 may be distributed to a patient. The patient may optionally pull handle 2494 distally away from injector 2400 thereby peeling adhesive protector 2389 from base 2442 and/or pulling needle protector 2492 and/or needle cover 2391 out a needle aperture in base 2442 and/or enabling injector 2400. Optionally the patient places adhesive base 2442 of the enabled injector 2400 against his skin and pushes distally on proximal cover 2421 collapsing needle shield 2441 and or activating injector 2400. For example, a needle may inserted through the needle aperture in base 2442 into the skin of the patient and/or switch 682 may be triggered activating motor 2476 and/or rotating couplings 2484a,b and/or extending a telescoping transmission 2458 and/or pushing plunger 2448 into barrel 2446 and/or discharging a medicine out the needle into the patient. Optionally, when plunger 2448 is blocked (for example when it reaches the end of barrel 2446 and/or due to a malfunction) the torque and/or linear force unlocks retraction mechanism 758. When retraction mechanism 758 is unlocked return spring optionally pushes syringe 2496 into the retracted position and/or releases switch 682 stopping motor 2476 and/or drug delivery. The patient optionally sees through window 2490b whether the entire dose has been discharged and/or through window 2490a whether the needle has been retracted (for example inner sleeve may be colored red and be visible in window 2490a before retraction and/or outer sleeve 767 may be colored green and/or may become visible in window 2490a after retraction). Once the needle has retracted, the patient optionally pivots injector 2400 off his skin (for example by twisting and/or inclining injector 2400).

In some embodiments, the form of the injector is designed to aid removal. For example the adhesive zone may have a short axis and/or a long axis. The injector is optionally tipped around a pivoting axis parallel to the long axis, such that the short axis is the lever for pulling the adhesive off the skin. Alternatively or additionally, the adhesive may have a reduced flexible skirt at the location from which it is to be removed from the skin.

Figure 24F:
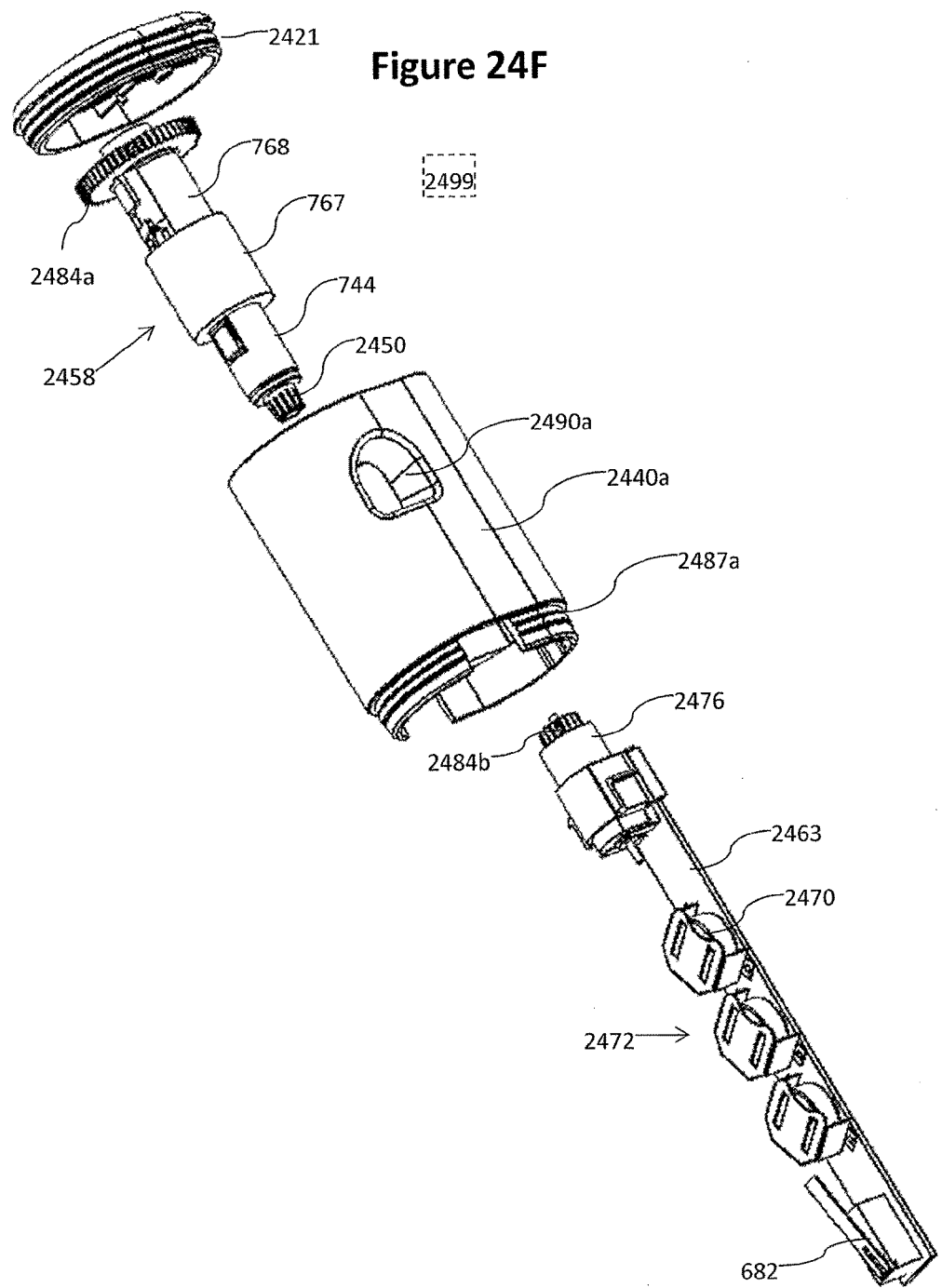
Figure 24G:
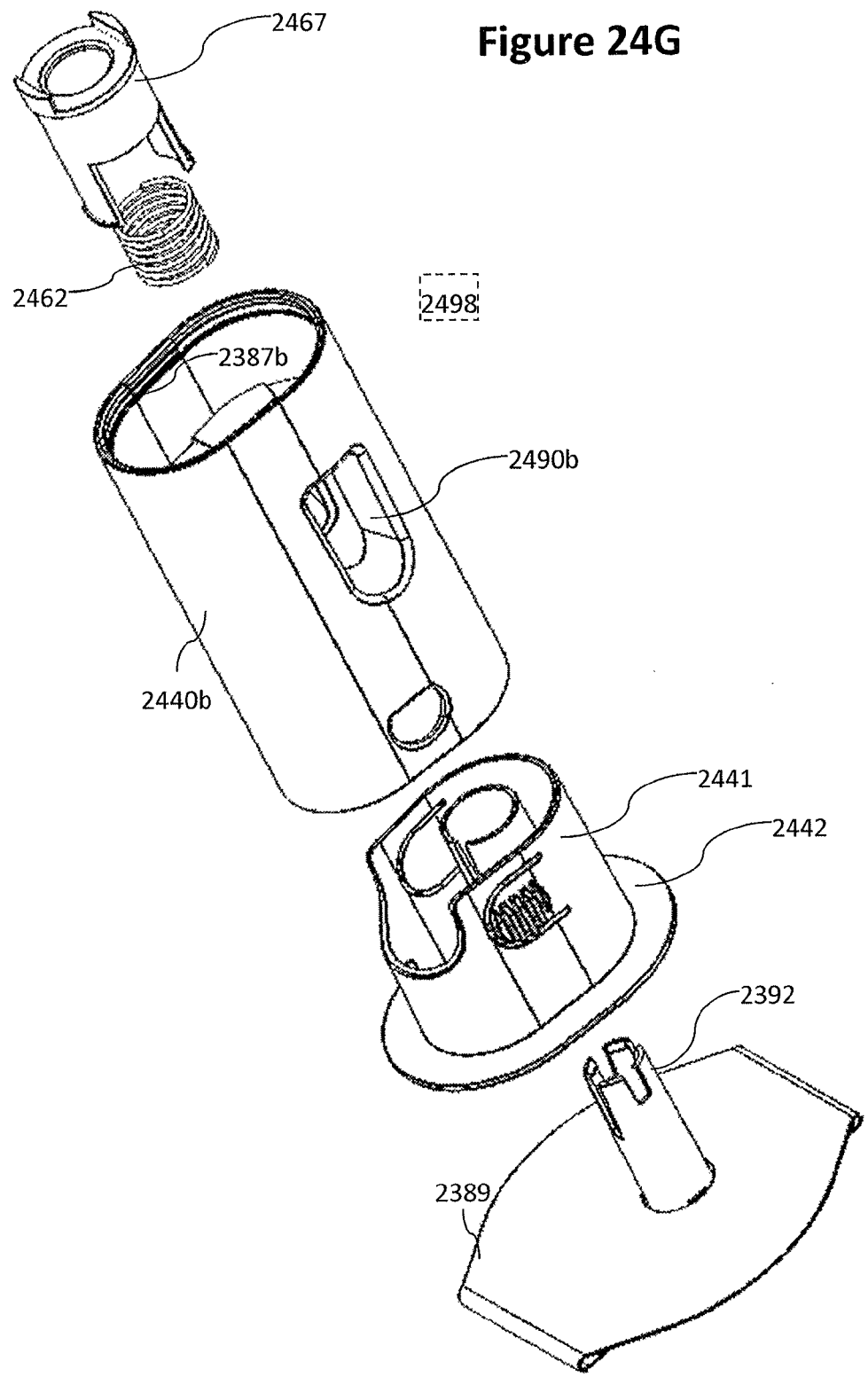

FIG. 24F illustrates assembly of proximal assembly 2499 in accordance with an embodiment of the current invention. For example, the assembled transmission 2558 module may be inserted into the proximal end of housing 2440a and/or the assembled power module 2472 may be inserted into the distal end of housing 2440a until coupling 2484a in engaged to coupling 2484b. Optionally proximal cover 2421 is placed over the proximal end of housing 2440a.

FIG. 24F illustrates assembly of distal assembly 2498 in accordance with an embodiment of the current invention. For example, needle shield 2441 is partially inserted into the distal end of housing 2440b. Optionally needle protector 2392 is inserted into the distal end of channel 2488 and/or retainer 2467 and/or spring 2462 are inserted into the proximal end of channel 2488. Optionally adhesive protector 2389 is placed over the distal side of adhesive base 2442. Optionally, adhesive protector 2389 is connected to handle 2494 by extenders (for example portions 785b,c as illustrated in FIG. 7C-H)

25 Modular Injector

Figure 25:
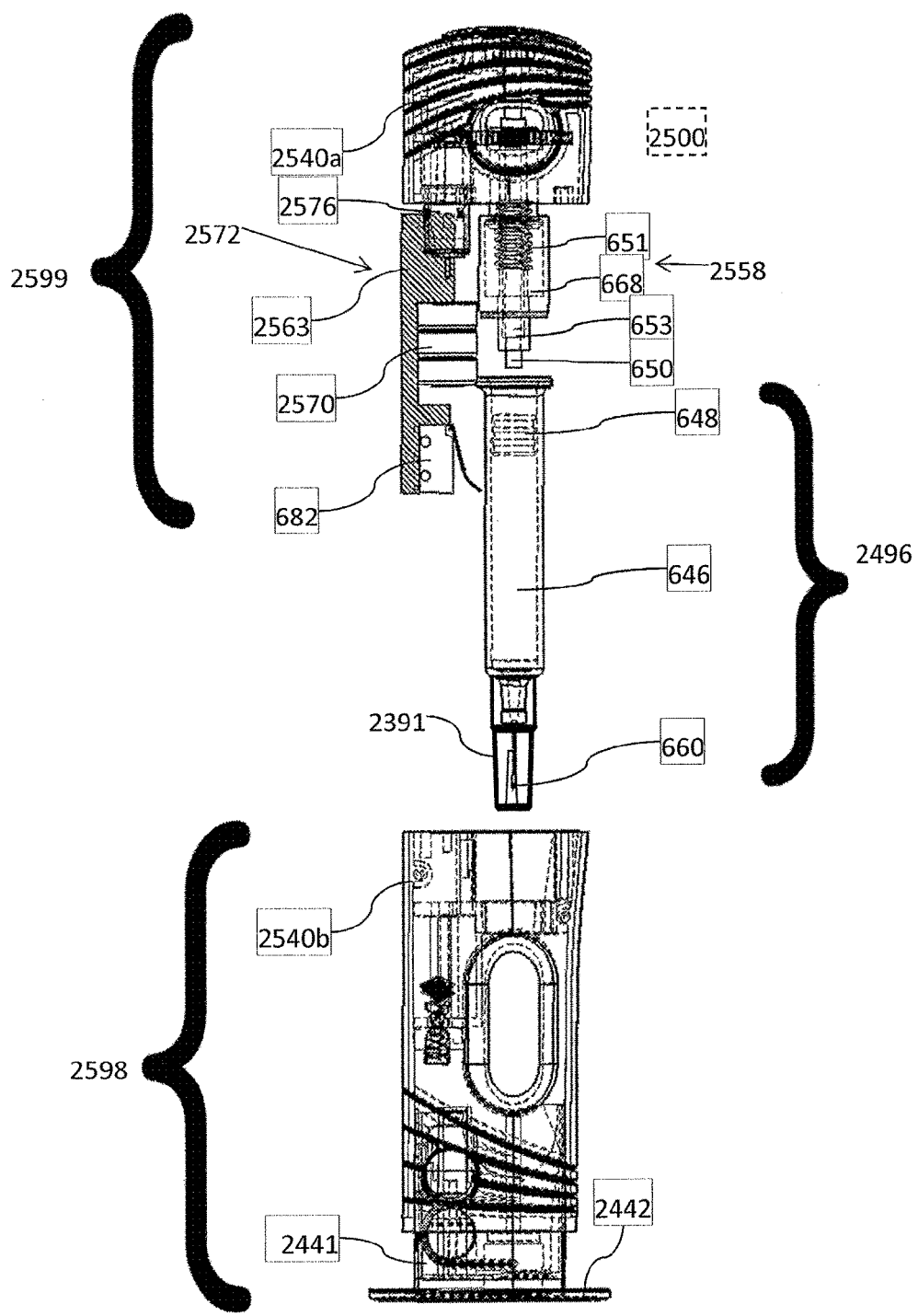
FIG. 25 illustrates a modular stabilized injector in accordance with an embodiment of the present invention.

FIG. 25 illustrates an alternative modular preloaded stabilized drug delivery device 2500 in accordance with an embodiment of the current invention. Device 2500 is optionally designed for simple final assembly by a drug distributor. For example a prefilled syringe 2496 is inserted into a channel in a distal assembly 2598 and/or a proximal assembly 2599 is snapped onto distal assembly 2598 via an axial motion. Device 2500 includes a transmission 2558 with a rotary needle retraction mechanism (for example as illustrated in FIGS. 6A-F). Power module 2572 includes a motor 2576 and/or batteries 2570 and/or a switch 682 rigidly mounted on a base 2563. Base 2563 may be made for example of molded plastic. Optionally distal assembly is assembled into a distal housing 2540b. Optionally proximal assembly is assembled into a proximal housing 2540a. Distal assembly 2598 may optionally not include a biasing element for needle return.

26 Method of Manufacture of a Stabilized Injector

Figure 26:
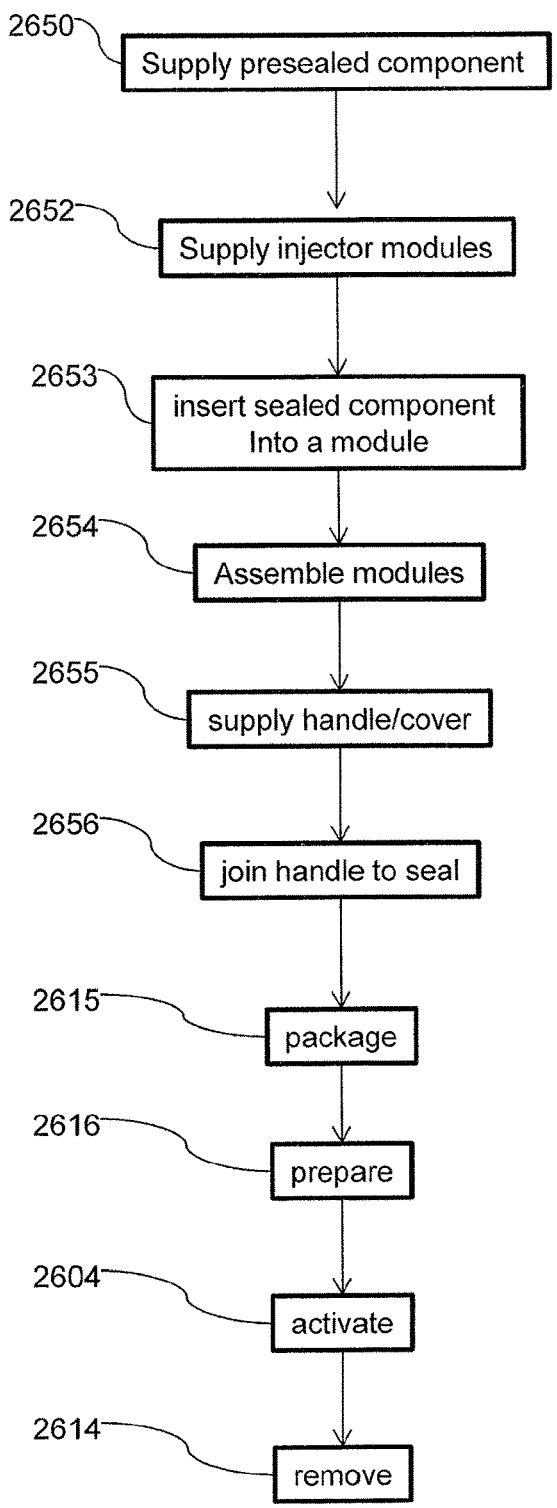
FIG. 26 is a flow chart illustrating a method of manufacture of a modular preloaded stabilized drug delivery device in accordance with an embodiment of the current invention.

FIG. 26 illustrates a method of manufacture of a modular preloaded stabilized drug delivery device in accordance with an embodiment of the current invention.

In some embodiments, a presealed and/or preloaded component is optionally supplied 2650. For example, a preloaded component may include a preloaded syringe with a sealed and/or covered sterile needle.

In some embodiments, preassembled modules of the injector are optionally supplied 2652. For example the preassembled modules may be designed for easy assembly.

In some embodiments, the presealed component may be inserted 2653 into one or more of the modules. During insertion 2653, a part of the presealed component may be connected to an enabling mechanism of the injector. For example, inserting a preloaded syringe into a channel of an injector may cause a needle protector to snap onto a sterile needle cover such that when the needle protector and/or an adhesive protector is removed from the device, the needle cover is also removed.

In some embodiments, the preassembled modules and/or the presealed component may be assembled 2654 together. For example the modular components may include a quick connection (for example a snap and/or a friction fit and/or a interference element) for simple assembly.

In some embodiments, the drug delivery device may include a stabilizer. A cover and/or activation mechanism and/or handle is optionally supplied 2655 for the stabilizer. For example, the stabilizer may include an adhesive surface which is activated by peeling off a surface cover. For example, a handle may be supplied 2655 for peeling the cover. Alternatively or additionally an adaptor may include the stabilizer and/or the adhesive cover and/or a safety cap. Optionally, various components of the activator and/or cover may be connected for synchronized removal and/or activation.

In some embodiments, the activation mechanism and/or surface cover of the adapter may be joined 2656 to the presealed component. For example, a coupler may connect between the handle and the seal of the presealed component and/or a safety cap. For example the coupler may be fit through an aperture (for example a needle aperture) in the adhesive surface to connect between the handle and the needle cover. For example an extender may connect the handle to the adhesive cover, for example for peeling the adhesive cover.

In some embodiments the entire assembled system including the presealed component and the preassembled modules may be packaged 2615 for shipping and/or sent to a dealer (for example a hospital and/or a pharmacist) and/or a patient. Optionally the injector may be shipped in a packed state. For example, components may be packaged in a folded and/or stacked manner, for example saving space and/or packaging materials.

In some embodiments, the injector may be prepared 2616 by the dealer and/or the patient. For example, the injector may be removed from packaging and/or unfolded and/or assembled. Preparing an injector may include enabling the injector. For example, enabling may include removing an adhesive protector and/or a needle protector and/or a sterility protector (for example a needle cover).

In some embodiments, the injector may be activated 2604. Activation 2604 may include fastening the injector to the patient and/or inserting a needle and/or activating a switch, for example a button.

After use the injector may be removed 2614 from the patient. For example the injector may include a needle protection system that guards the needle to avoid a sharp point hazard. In some embodiments, the injector or part thereof may be disposed of in domestic waste.

27 Method of Stabilizing a Pen Injector

Figure 27:
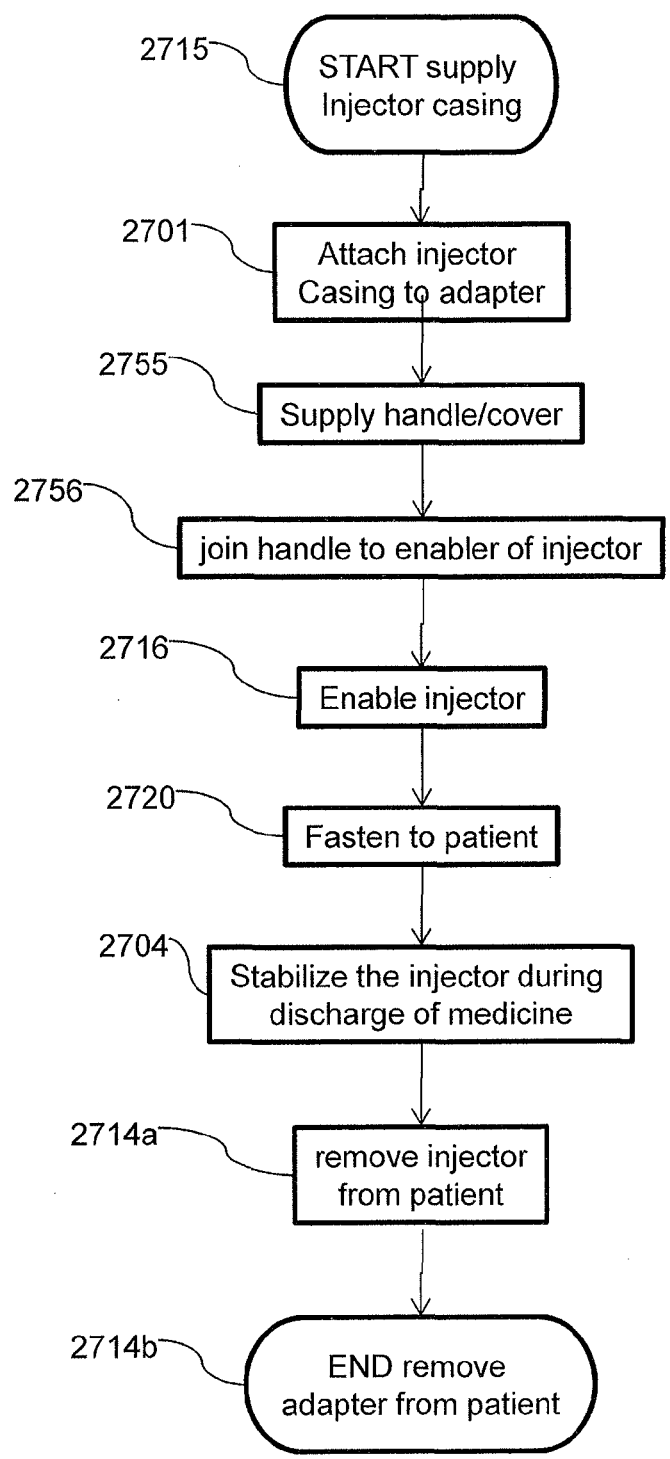
FIG. 27 is a flow chart illustrating a method of retrofitting a pen injector in accordance with an embodiment of the current invention.

FIG. 27 illustrates a method of stabilizing a pen injector in accordance with an embodiment of the current invention. For example the method may be used to retrofit an existing pen injector.

In some embodiments a pen injector may be supplied 2715. For example the pen injector may be capable of use in an autonomous mode (without stabilization).

In some embodiments a stabilizer (for example a stabilizing adapter) may be attached 2701 to the housing of the injector. For example the stabilizer may include a relatively large skin contact surface and/or an adhesive surface to hold the injector onto an injection site during injection. Optionally, the injector may be supplied to a patient with the stabilizing adaptor already attached. For example the stabilizer may be attached to the injector by a drug supplier and/or a drug distributor and/or a retailer and/or a dealer (for example a pharmacist and/or a health worker). Alternatively or additionally the patient may attach the adaptor to the injector before enabling the injector and/or before uncovering the adhesive and/or before fastening the adaptor to his skin and/or before activating the injector).

In some embodiments, the stabilizer may be adapted to allow the injector to function according to its autonomous mode for example:

1. In some embodiments an injector may have a sleeve that extends out of the distal end of the injector at the end of injection. A stabilizing adapter may optionally include a large needle aperture. For example the needle aperture may be large enough to allow the sleeve to protrude through the needle aperture after injection. Alternatively or additionally, the adapter may be designed so that the injector is axially releasably connected to the adapter. For example after injection, the injector is removed by an axial movement from the adapter while the adapter remains on the skin of the patient. Removing the injector from the adapter may allow the sleeve to extend while removing the injector. After removing the injector, then the adapter is optionally removed from the patient. For example, the injector may be connected to the adaptor with a friction fitting and/or a reversible snap and/or interference snap fit and/or with an adhesive and/or with a breakable joint that allows the injector to be removed axially from the adapter. Alternatively or additionally, the adapter may be designed so that at the end of injection, an attachment between the injector and the adaptor is released automatically and/or by a manual action.

2. In some embodiments an injector may have a skin contact sensor. An adapter may be designed with a hole that allows the skin contact sensor to protrude from the adapter. Alternatively or additionally, the injector may be supplied to a patient with the injector partially inserted. The patient may adhere the adapter to his skin and then push the injector distally against the adapter. Pressure of the distal end of the injector due to the pressure by the patient may serve to activate the injector as if it were held against the patient's skin.

3. In some embodiments an injector may have a retractable needle. Optionally the adapter may have a large and/or a small needle aperture allowing insertion and/or retraction of the needle.

In some embodiments a cover and/or activation mechanism and/or handle may be supplied 2755 for the stabilizing adaptor. For example, the stabilizing adapter may include an adhesive surface which is activated by peeling off a surface cover. For example, a handle may be supplied 2755 for peeling the cover. Alternatively or additionally adaptor may include a safety cap. Optionally, various components of the activator and/or cover may be connected for synchronized removal and/or activation.

In some embodiments, the activation mechanism and/or surface cover of the adapter may be joined 2756 to an enabling mechanism of the injector. For example, a coupler may connect between the handle and the seal of a protected component and/or a safety cap. For example the coupler may be fit through an aperture (for example a needle aperture) in the adapter to connect between the handle and an enabling mechanism of the injector.

In some embodiments, before use the stabilized injector system may be enabled 2716. For example, enabling the injector may include manipulating the handle of the adapter to activate the adapter and/or enable the injector.

In some embodiments the combined injector adaptor system may be fastened 2720 to a patient before injection. The injector may inject a drug while stabilized 2704 by and/or attached to the stabilizing adaptor.

In some embodiments, the injector may be removed 2714*a* from the patient after the drug has been discharged and/or in the case of a malfunction. Removal 2714*a* may be adapted to the injector design and/or status. For example, for an injector which retracts the needle at the end of injection, the injector and stabilizer may be peeled and/or pivoted off the patient together, for example by twisting and/or inclining the injector adaptor system. Alternatively or additionally, the injector may for example be removed 2714*a* from the adapter and the patient simultaneously by an axial movement. For example in removing 2714*a* the injector by axial movement may be useful where the needle does not retract (for example for injector that does not have a retraction mechanism and/or in the case of a malfunction when the needle failed to retract). Optionally, the adaptor and injector may sometimes be removed 2714*a,b* by inclining the injector and/or pivoting the adaptor. Alternatively or additionally the adaptor may have a safety release that allows the injector to be removed 2714*a* from the adaptor when desired and/or under specified circumstances. Alternatively or additionally the injector may be attached to the adaptor in a way that allows axial removal 2714*a* of the injector from the adaptor using a force that is less than the expected axial force necessary to remove the adhesive from the skin. For example, the injector may be removed from the adapter by a linear force ranging between 0.1 to 0.2 N and/or between 0.2 to 0.4 N and/or between 0.4 to 0.8 N and/or between 0.8 to 1.6 N and/or between 1.6 to 3.2 N. Alternatively or additionally, the geometry of the adapter may allow pealing the adapter off the patient while pulling the needle more or less axially from the skin (for example, the needle aperture of the adaptor may be located closer to an edge that is lifted from the skin and further from an edge that is used as a fulcrum for pivoting the injector).

In some embodiments, after injection, the adapter and/or the adhesive may be removed 2714*b* from the skin of the patient. For example removal 2714*b* of the adaptor may be after removal 2714*a* of the injector and/or simultaneous to removal 2714*a* of the injector and/or prior to removal 2714*a* of the injector.

28 Removing a Stabilized Pen Injector

Figure 28A:
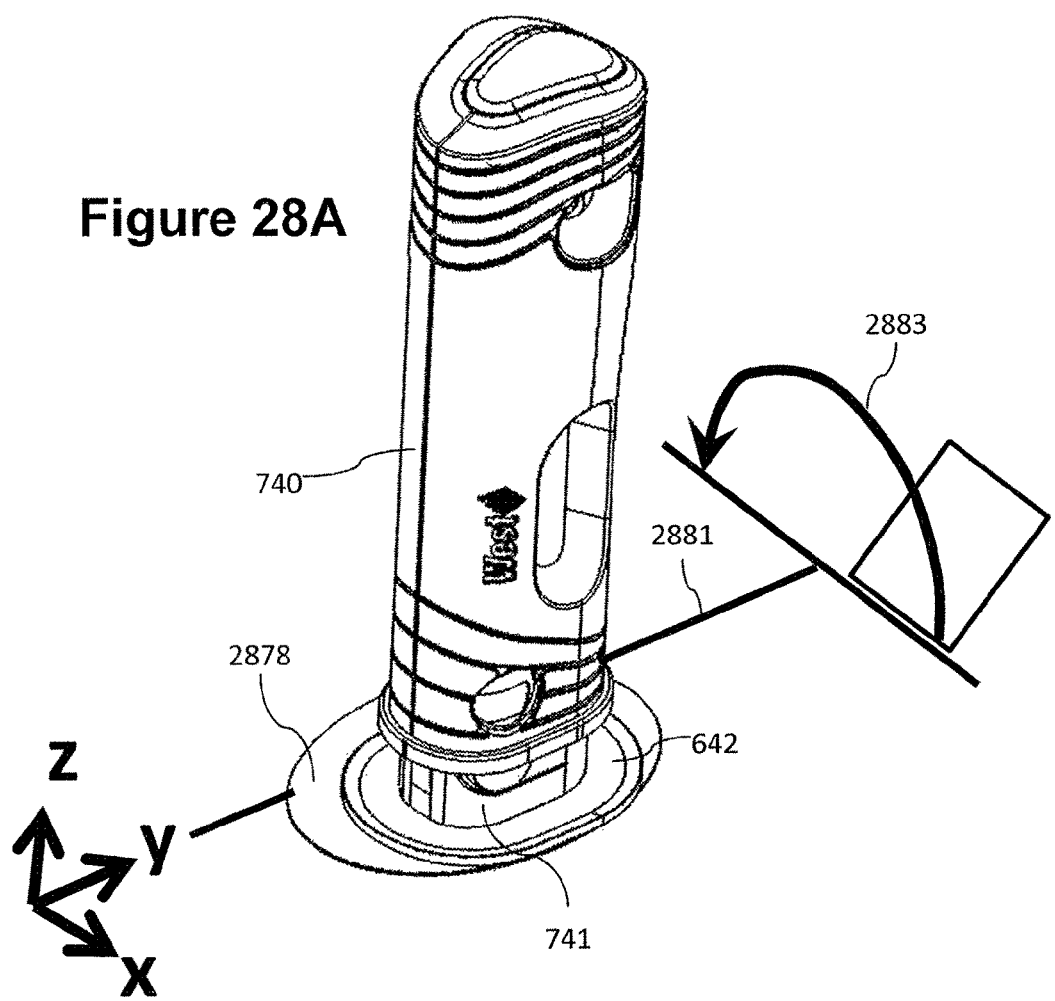
FIGS. 28A-C illustrate removing a stabilized pen injector in accordance with an embodiment of the current invention.
Figure 28B:
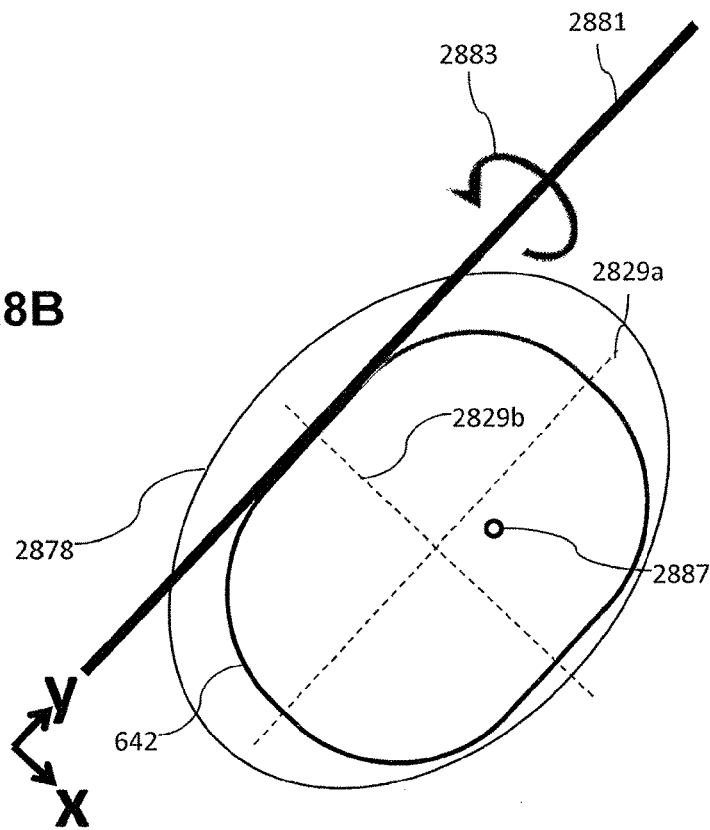
Figure 28C:
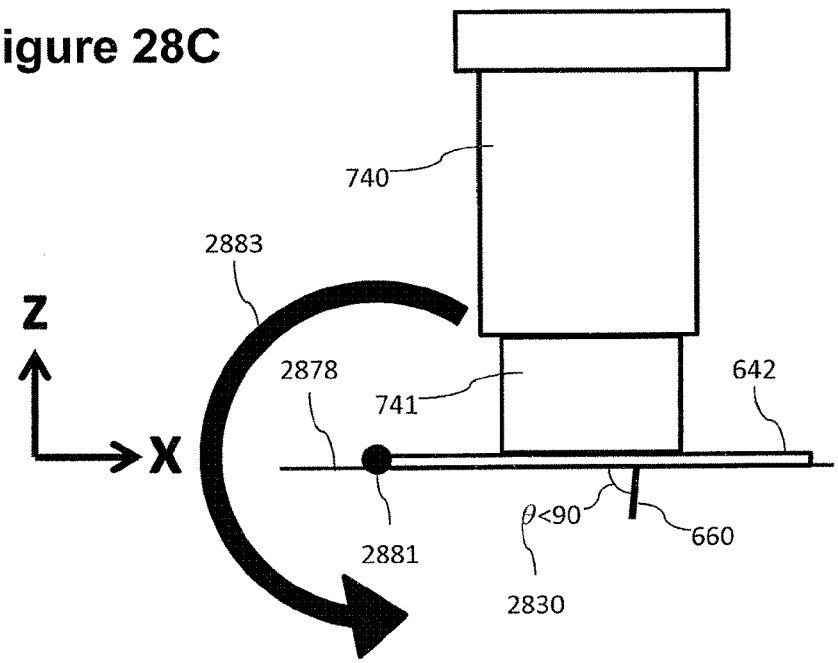

FIGS. 28A-C illustrate removing a stabilized pen injector in accordance with an embodiment of the current invention. Optionally, the injector is removed by pivoting off the skin. Optionally, an adhesive base 642 of the injector has a non-symmetric shape for example including a long axis 2829*a* and/or a short axis 2829*b*. Pivoting may be for example around an axis 2881 of pivoting that is approximately perpendicular to the short axis 2829*b* of base 642 and/or approximately parallel to the long axis 2829*a* of the base 642. An adhesive skirt 2878 may extend past the edge of the base on at least one side. The adhesive skirt may extend further along an edge close to axis 2881 of pivoting than along an edge opposite axis 2881 of rotation. A needle aperture 2887 may be distanced from the axis 2881 of pivoting.

In some embodiments, axis 2881 of pivoting may be along an edge of base 642. For example, base 642 may include a linear edge at the location intended for axis 2881 of pivoting. An exemplary direction of pivoting is illustrated by arrow 2883. Optionally, adhesive skirt 2878 may extend further from the edge of base near the axis 2881 of pivoting than from the edges far from and/or opposite axis 2881 of pivoting. For example, skirt 2878 may extend between 1 to 2 mm and/or between 2 to 3 mm and/or between 3 to 4 mm and/or between 4 to 10 mm from an edge of base 642 near axis 2881 of pivoting. For example, skirt 2878 may extend between 0 to 1 mm and/or between 2 to 3 mm and/or between 3 to 4 mm from an edge of base 642 far from and/or opposite axis 2881 of pivoting.

In some embodiments, a needle location and/or a needle aperture (for example an location and/or an aperture 2887 from which a needle 660 extends from the injector into the skin of the patient [for example see FIG. 28C]) may be located to reduce a torque on needle 660 when pivoting the injector from the skin of the patient. For example the needle aperture 2887 and/or needle location may be located opposite and/or distanced from axis 2878 of pivoting. For example, the needle location and/or aperture 2887 may be located closer to the side of base 642 opposite the axis 2881 of pivoting than to the side of base 642 near axis 2881 of pivoting. For example the position of needle location and/or aperture 2887 may range between 51 to 60% of the distance along a line from axis 2881 of pivoting to an opposite edge of adhesive base 642 and/or between 60 to 70% of the distance along a line from axis 2881 of pivoting to an opposite edge of adhesive base 642 and/or between 70 to 90% of the distance along a line from axis 2881 of pivoting to an opposite edge of adhesive base 642 and/or between 90 to 100% of the distance along a line from axis 2881 of pivoting to an opposite edge of adhesive base 642. For example, the needle location and/or aperture 2887 may be located at a distance ranging between 5 mm to 15 mm from axis 2881 of pivoting and/or between 15 mm to 30 mm from axis 2881 of pivoting and/or between 30 mm to 60 mm from axis 2881 of pivoting and/or more than 60 mm from axis 2881 of pivoting. For example, the needle location and/or aperture 2887 may be located at a distance ranging between 0 mm to 5 mm from the side of base 642 opposite axis 2881 of pivoting and/or between 5 mm to 15 mm the side of base 642 opposite axis 2881 of pivoting and/or between 15 mm to 60 mm from the side of base 642 opposite axis 2881 of pivoting. Alternatively or additionally, needle 660 may be oriented to reduce torque during pivoting of the injector. For example, needle 660 may be pointed inward with respect to axis 2881 of pivoting. For example the needle 660 may be pointed inward with respect axis 2881 of pivoting at an angle 2830 to base 642 ranging for example between 99.9 and 99 degrees and/or between 99 and 98 degrees and/or between 98 and 95 degrees and/or between 95 and 90 degrees.

29 Stabilizer with Large Needle Aperture

Figure 29A:
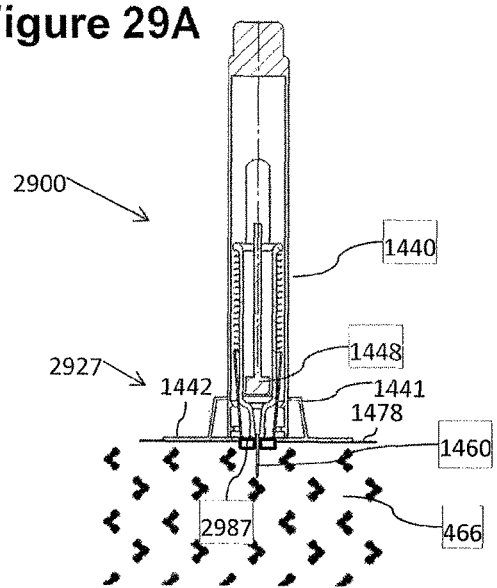
FIGS. 29A-B illustrate a stabilizing adaptor having a large needle aperture in accordance with an embodiment of the current invention
Figure 29B:
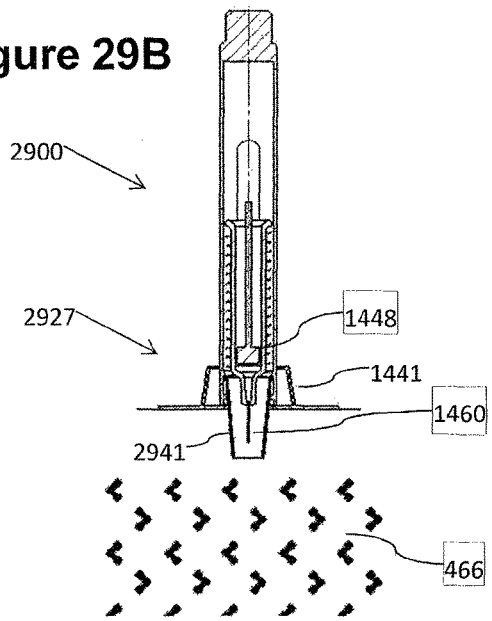

FIGS. 29A-B illustrate a stabilizing adaptor 2927 having a large needle aperture 2987 in accordance with an embodiment of the current invention. Optionally stabilizing adaptor 2927 may be in the form of an open ring (optionally the ring may have an arbitrary cross section [circular and/or non-circular]) with an adhesive base 642 surrounding the cavity of the ring. Alternatively, needle aperture 2987 may be smaller than the cavity of adapter 2827.

In some embodiments, stabilizing adapter 2927 with large needle aperture 2987 may be used with an injector 2900 having a protruding component. Aperture 2987 may be large enough for the protruding component to protrude through the aperture. For example, injector 2900 includes a needle shield 2941 that pops out to surround and/or protect needle 1460. For example, shield 2941 may extend out of housing 1440 of injector 2900 and/or through needle aperture 2987 of adapter 2927 before injection of medicine. For example, shield 2941 collapse into of housing 1440 of injector 2900 and/or through needle aperture 2987 of adapter 2927 when injector 2900 is activated exposing needle 1460 (for example as illustrated with respect to injector 600 in FIGS. 6A,B). Alternatively or additionally, shield 2941 may extend out of housing 1440 of injector 2900 and/or through needle aperture 2987 of adapter after injection of medicine, for example for protecting needle 1460 after injection (for example when injector 2900 and/or adapter 2927 are removed from skin 466 of the patient.

In some embodiments a width of the needle aperture along its smallest axis may range between 1 mm and 2 mm and/or between 2 mm and 4 mm and/or between 4 mm and 8 mm and/or between 8 mm and 16 mm. Alternatively or additionally the width of the needle aperture along its smallest axis may range between 10% and 20% a width of the injector along its smallest axis and/or between 20 and 40% and/or between 40% mm and 80% and/or between 80 and 100% the width of the injector along its smallest axis.

30 Stabilizer Axially Reversible Attachment to an Injector

Figure 30A:
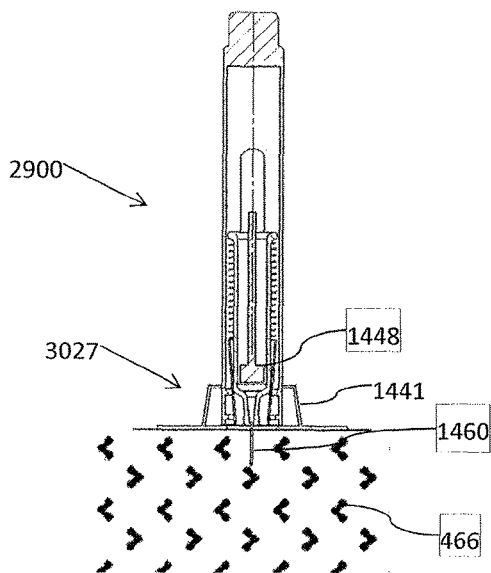
FIGS. 30A-B illustrate a stabilizing adaptor which allows an injector to be removed from the adapter axially in accordance with an embodiment of the current invention.
Figure 30B:
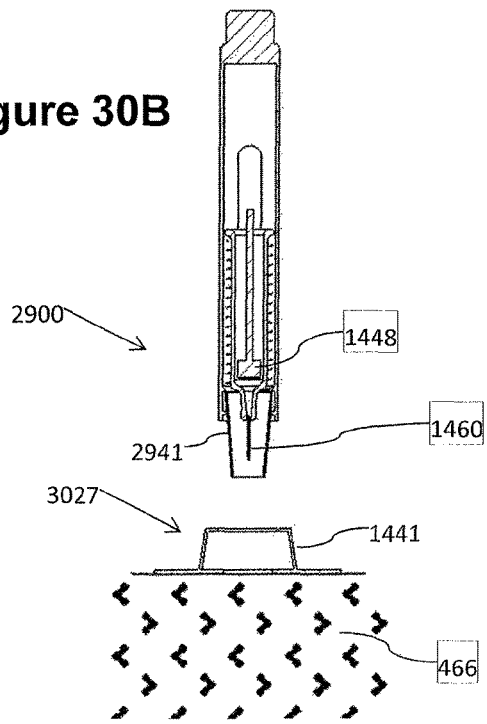

FIGS. 30A-B illustrate a stabilizing adaptor 3027 which allows an injector 2900 to be removed from the adapter axially in accordance with an embodiment of the current invention. Optionally stabilizing adaptor 3027 may be in the form of an open ring (optionally the ring may have an arbitrary cross section [circular and/or non-circular]) with an adhesive base 642 surrounding the cavity of the ring. Alternatively, needle aperture 2987 may be smaller than the cavity of adapter 2827.

In some embodiments, stabilizing adapter 3027 may be used with an injector 2900 having a protruding component. For example shield 2941 may extend out of housing 1440 of injector 2900 after injection of medicine protecting needle 1460 after injection (for example when adapter 3027 is removed from adapter 3027 and/or skin 466 of the patient).

31 Distributing a Stabilized Injector

Figure 31:
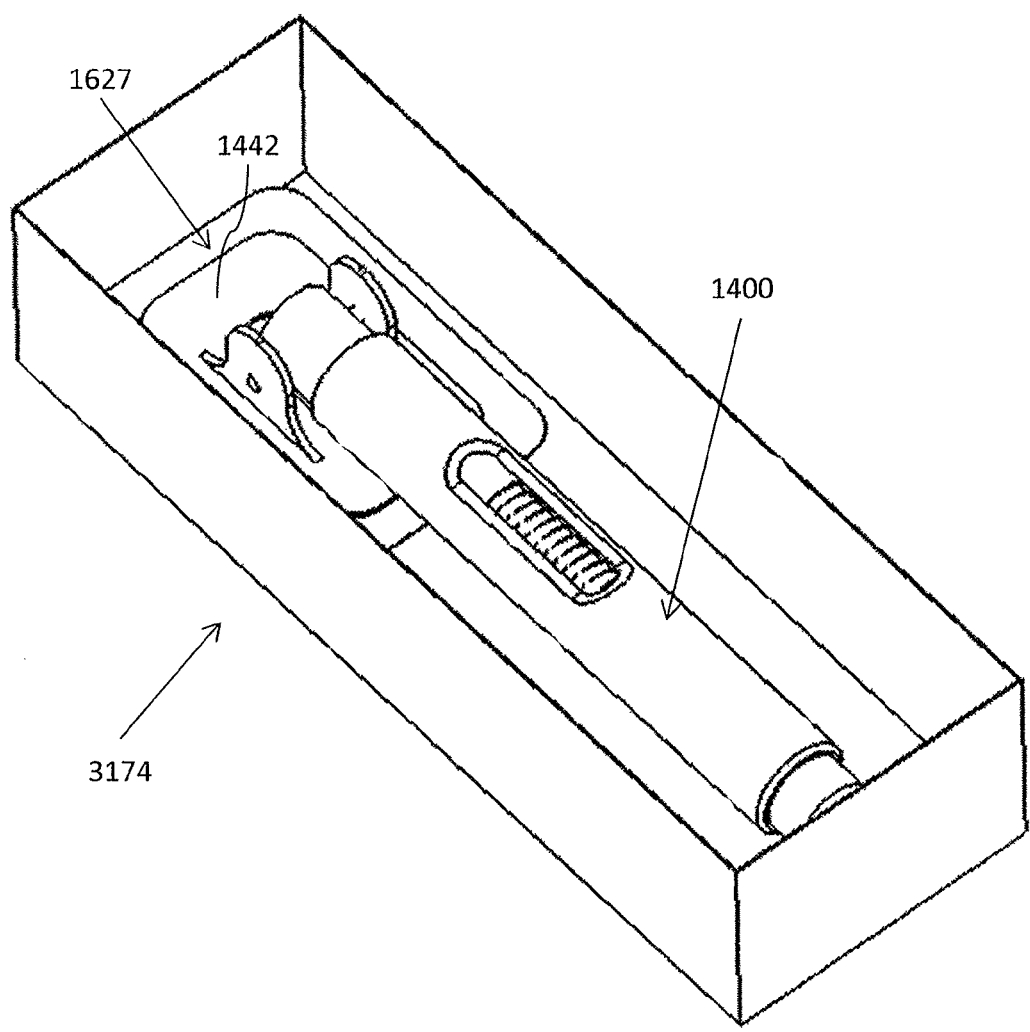
FIG. 31 illustrates pen injector 1400 retrofit with stabilizing adaptor 1627 packaged for distribution in accordance with an embodiment of the current invention.

FIG. 31 illustrates pen injector 1400 retrofit with stabilizing adaptor 1627 packaged for distribution in accordance with an embodiment of the current invention. Optionally, stabilizing adaptor 1627 has a packed configuration (where injector 1400 is, for example, oriented parallel at 0 degrees to the base 1442 of adaptor 1627) that takes up less space when packed in a packaging (for example a box 3174) than in the active configuration (where injector 1400 is, for example, oriented at between 60 to 120 degrees to the base 1442 of adaptor 1627). Optionally, adapter 1627 may automatically revert to the active configuration (for example by a biasing element e.g. a spring) when removed from packaging 3174.

It is expected that during the life of a patent maturing from this application many relevant technologies will be developed and the scope of the terms are intended to include all such new technologies a priori.

As used herein the term "about" refers to ±5%. As used herein the term "approximately" when used in reference to an angle refers to ±10 degrees.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A stabilized autoinjector assembly comprising:
   an autoinjector comprising:
      a syringe including a drug container,
      a hollow needle connected to a distal end of the drug container and in fluid communication with an interior of the drug container, and
      a plunger sealing a proximal opening of the drug container;
   a stabilizer comprising:
      an adhesive base having a long axis and a short axis, a first edge and an opposing second edge, and a needle aperture, the first and second edges extending parallel to the long axis, the adhesive base having an aspect ratio of the long axis to the short axis of at least 1.5 to 1, and
      a flexible adhesive skirt extending beyond at least the first edge of the adhesive base, the flexible adhesive skirt extending in a direction of the short axis of the adhesive base further from the first edge of the adhesive base than from the second edge of the adhesive base; and
      a pivoting axis extending parallel to the long axis of the base, wherein an adhesive strength the adhesive base is small enough such that when the stabilized autoinjector assembly is pivoted around the pivoting axis, the stabilized autoinjector assembly is pivoted off a skin of a patient without ripping the skin.

2. The stabilized autoinjector assembly of claim 1, wherein the pivoting axis is near the first edge and far from the second edge.

3. The stabilized autoinjector assembly of claim 1, wherein the pivoting axis is along the first edge of the adhesive base.

4. The stabilized autoinjector assembly of claim 1, wherein the first and second edges are substantially perpendicular to the short axis.

5. The stabilized autoinjector assembly of claim 1, wherein the needle aperture in the adhesive base is offset from the first edge toward the second edge.

6. The stabilized autoinjector assembly of claim 1, wherein the hollow needle is oriented toward the first edge of the adhesive base at an angle between 85 and 99 degrees.

7. The stabilized autoinjector assembly of claim 1, wherein a height of the autoinjector is equal to at least a length of the short axis of the adhesive base.

8. The stabilized autoinjector assembly of claim 1, wherein the hollow needle has a principle longitudinal axis that is substantially parallel to an axis of the drug container.

9. The stabilized autoinjector assembly of claim 1, further comprises:
   a needle cover for the hollow needle of the autoinjector, and
   a handle connected to the needle cover such that a linear movement of the handle pulls the needle cover through the needle aperture of the base.

10. The stabilized autoinjector assembly of claim 9, further comprising:
    an adhesive cover for the adhesive base connected to the handle by an extender, wherein the linear movement of the handle causes the adhesive cover to be peeled from the adhesive base.

11. The stabilized autoinjector assembly of claim 9, wherein the adhesive base is located distal to all of the needle cover.

12. The stabilized autoinjector assembly of claim 1, further comprising a needle protection sheath configured to protrude distally from the autoinjector and surround the hollow needle.

13. The stabilized autoinjector assembly of claim 12, wherein the needle aperture is large enough for the needle protection sheath to extend through the needle aperture.

14. The stabilized autoinjector assembly of claim 1, further comprising:
    a fastener configured to attach the adhesive base of the stabilizer to the skin of the patient; and
    a connector configured to be axially reversible attached to a housing of the autoinjector and to reversibly hold the housing in a fixed orientation relative to the fastener.

15. A method of injecting a substance into a patient using a stabilized autoinjector assembly, the method comprising:
    (i) obtaining a stabilized autoinjector assembly comprising:
       an autoinjector including a syringe and a needle; and
       a stabilizer including:
          an adhesive base having a long axis and a short axis, a first edge and an opposing second edge, and a needle aperture, the first and second edges extending parallel to the long axis, the adhesive base having an aspect ratio of the long axis to the short axis of at least 1.5 to 1, and
          a flexible adhesive skirt extending beyond at least the first edge of the adhesive base, the flexible adhesive skirt extending in a direction of the short axis of the adhesive base further from the first edge of the adhesive base than from the second edge of the adhesive base, and a pivoting axis extending parallel to the long axis of the base;

(ii) fastening the adhesive base of the stabilized autoinjector assembly to a skin of the patient;

(iii) moving the syringe axially with respect to the adhesive base to insert the needle through the needle aperture of the adhesive base into the patient;

(iv) discharging the substance from the syringe through the needle into the patient while the stabilized autoinjector assembly remains fastened to the patient; and (v) pivoting the stabilized autoinjector assembly about the pivoting axis along the skin to unfasten the adhesive base from the patient, wherein an adhesive strength the adhesive base is small enough such that when the stabilized autoinjector assembly is pivoted around the pivoting axis, the stabilized autoinjector assembly is pivoted off the skin of the patient without ripping the skin.

16. The method of claim 15, wherein the pivoting axis is near the first edge and far from the second edge.

17. The method of claim 15, wherein the pivoting axis is along the first edge of the adhesive base.

18. The method of claim 15, wherein the first and second edges are substantially perpendicular to the short axis.

19. The method of claim 15, wherein the needle aperture in the adhesive base is offset from the first edge toward the second edge.

20. The method of claim 15, wherein when the stabilized autoinjector assembly is pivoted about the pivoting axis, the needle is oriented toward the first edge of the adhesive base at an angle between 85 and 99 degrees.

* * * * *